(12) United States Patent
Kara et al.

(10) Patent No.: US 10,703,815 B2
(45) Date of Patent: Jul. 7, 2020

(54) LIGANDS THAT POTENTIATE THE BIOACTIVITY OF GONADOTROPINS

(71) Applicant: Repropharm, Nouzilly (FR)

(72) Inventors: Elodie Kara, Veigne (FR); Jeremye Decourtye, Tours (FR); Sophie Casteret, Valleres (FR); Marie-Christine Maurel, Tours (FR)

(73) Assignee: IGYXOS, Nouzilly (FR)

( * ) Notice: Subject to any disclaimer, the term of this patent is extended or adjusted under 35 U.S.C. 154(b) by 41 days.

(21) Appl. No.: 15/510,492

(22) PCT Filed: Sep. 10, 2015

(86) PCT No.: PCT/FR2015/052413
§ 371 (c)(1),
(2) Date: Mar. 10, 2017

(87) PCT Pub. No.: WO2016/038308
PCT Pub. Date: Mar. 17, 2016

(65) Prior Publication Data
US 2017/0190773 A1 Jul. 6, 2017

(30) Foreign Application Priority Data

Sep. 10, 2014 (FR) .................... 14 58469

(51) Int. Cl.
*C07K 16/26* (2006.01)
*A61K 39/00* (2006.01)

(52) U.S. Cl.
CPC ........ *C07K 16/26* (2013.01); *A61K 2039/505* (2013.01); *C07K 2317/14* (2013.01); *C07K 2317/33* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/624* (2013.01); *C07K 2317/626* (2013.01); *C07K 2317/70* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 2002/0102613 A1 | 8/2002 | Hoogenboom |
| 2013/0243795 A1* | 9/2013 | Chen .................. C07K 16/2878 424/173.1 |
| 2017/0190774 A1 | 7/2017 | Kara et al. |

FOREIGN PATENT DOCUMENTS

| EP | 1518863 A1 | 3/2005 |
| WO | 9405690 A | 3/1994 |
| WO | 9712038 | 4/1997 |
| WO | 2007030930 A1 | 3/2007 |
| WO | 2012066519 A1 | 5/2013 |
| WO | WO 2013/138586 * | 9/2013 ........... A61K 39/395 |

OTHER PUBLICATIONS

Bhattacharya et al., PLoS One, 2017; 12(3): e0171355. https://doi.org/10.1371/journal.pone.0171355; 22 pages total. (Year: 2017).*
Johnson & Everitt, in Essential Reproduction, Fifth Edition, 2000; Blackwell Science Ltd., Chapter 15, "Fertility", pp. 265-271. (Year: 2000).*
Fertil Steril. 2004; 81: 1441-6, from the Practice Committee of the American Society for Reproductive Medicine; doi:10.1016/j.fertnstert. 2004. 01.019 (Year: 2004).*
Bernauer et al. "A new protein-protein docking scoring function based on interface residue properties" Bioinformatics; 2007; vol. 23(5); pp. 555-562.
Bernauer et al. "A Voronoi tessellation-based method for discriminating crystallographis and biological protein protein interactions"; Structural Bioinformatics; 2008; vol. 24(5); pp. 652-658.
Bourquard et al. "A Collaborative Filtering Approach for Protein-Protein Docking Scoring Functions" PLoS One; 2011; 6(4); e18541.
Bourquard et al. Unraveling the molecular architecture of a G protein-coupled receptor/B-arrestin/Erk module complex; Scientific Reports; 2015; 5:10760.
Brochet et al "IMGT/V-QUEST: the highly customized and integrated system for IG and TR standardized V-J and V-D-J sequence analysis" Nucl. Acids Res. 2008; vol. 36; W503-W508.
Chopineau et al. "Topography of equine chorionic gonadotropin epitopes relative to the luteinizing hormone and follicle-stimulating hormone receptor interaction sites" Mol. Cell. Endocrinol; 1993; 92(2); 229-239.
Corpet "Multiple sequence alignment with hierarchical clustering" Nucl. Acids Res.; 1988; 16(22); 10881-10890.
Fan et al. "Structure of human follicle-stimulating hormone in complex with its receptor" Nature; 2005; 433; 269-277.
Giudicelli et al INGT/GENE-DB: a comprehensive database for human and mouse immunoglobulin and T cell receptor genes: Nucleic Acids Research; 2005; vol. 33; D256-D261.
Giudicelli et al. "IMGT/V-QUEST: IMGT Standarized Analysis of the Immunoglobulin (IG) and T Cell Receptor (TR) Nucleotide Sequences" Cold Spring Harb Protoc.; 2011; 2011(6) 695-715.
Glencross et al. "Monoclonal antibody enhancement of OSH-induced uterine growth in snell dwarf mice" Journal of Endocrinology, Society for Endocrinology, BG, vol. 136, No. 3, Mar. 1, 1993, pp. R5-R7, XP009145848.
Internatioanl Preliminary Report on Patentability; Application No. PCT/FR2015/052413; International Filing Date Sep. 9, 2015, dated Jan. 2, 2017, 7 pages; English Translation.

(Continued)

*Primary Examiner* — Christina M Borgeest
(74) *Attorney, Agent, or Firm* — Cantor Colburn LLP

(57) ABSTRACT

The invention relates to antibodies directed against follicle-stimulating hormone (FSH) and capable of potentiating the bioactivity of gonadotropins.

49 Claims, 21 Drawing Sheets
Specification includes a Sequence Listing.

(56) References Cited

OTHER PUBLICATIONS

International Preliminary Report on Patentability; Application No. PCT/FR2015/052413; International Filing Date Sep. 9, 2015, dated Jan. 2, 2017, 7 pages;Non-English Translation.
International Search Report; International Application No. PCT/FR2015/052413; International Filing Date Sep. 10, 2015; dated Nov. 12 2015, 3 pages; English Translation.
International Search Report;International Application No. PCT/FR2015/052413; International Filing Date Sep. 10, 2015; dated Nov. 12, 2015, 5 pages; Non-English Translation.
Li et al. "An improved calcium chloride method preparation and transformation of competent cells" African Journal of Biotechnology; 2010; vol. 9(50); pp. 2549-2554.
Miller K F et al. "Immunoaffinity chromatography of bovine FSH using monoclonal antibodies" Database Medline (Online), US National Library of Medicine, Bethesda, MD, US; Nov. 1987, XP002751132, Database accession No. NLM3125301.
Reverchon et al. Chemerin inhibits IGF-I-induced progesterone and estradiol secretion in human granulosa cells; Human Reproduction; 2012; 27(6); pp. 1790-1800.
Scobey et al. "Multiple ratios of FSH and LH bioactivity using highly purified, human-derived FSH (Bravelle) and highly purified hMG (MENOPUR) are unaltered by mixing together in the same syringe" Reproductive Biology and Endocrinology; 2005; 3; 61.
Steelman et al. "Assay of the Follucle Stimulating Hormone based on the Augmentation with Human Chorionic Gonadotropin" Endocrinology; 1953; 53; 604-616.
Ulloa-Aguirre et al. "Novel pathways in gonadotropin recertor signaling and biased agonism" Reviews in Endocrine and Metabolic Disorders, Kluwer Academic Publishers, BO, vol. 12, No. 4, 28 Apr. 2011, pp. 259-274, XP019972343.
Ward et al. "Binding activities of a repertoire of single immunoglobulin variable domains secreted from *Escherichia coil*" Nature; 1989; 341; 544-546.
Wehbi et al. Selective Modulation of Follicle-Stimulating Hormone Signaling Pathways with Enhancing Equine Chorionic Gonadotropin/ANtibody Immune Complexes; Endocrinology; 2010; 151(6); 2788-2799.
Written Opinion of the International Searching Authority; Application No. PCT/FR2015/052413; International Filing Date Sep. 9, 2015, dated Mar. 17, 2016, 5 pages;Non-English Translation.

* cited by examiner

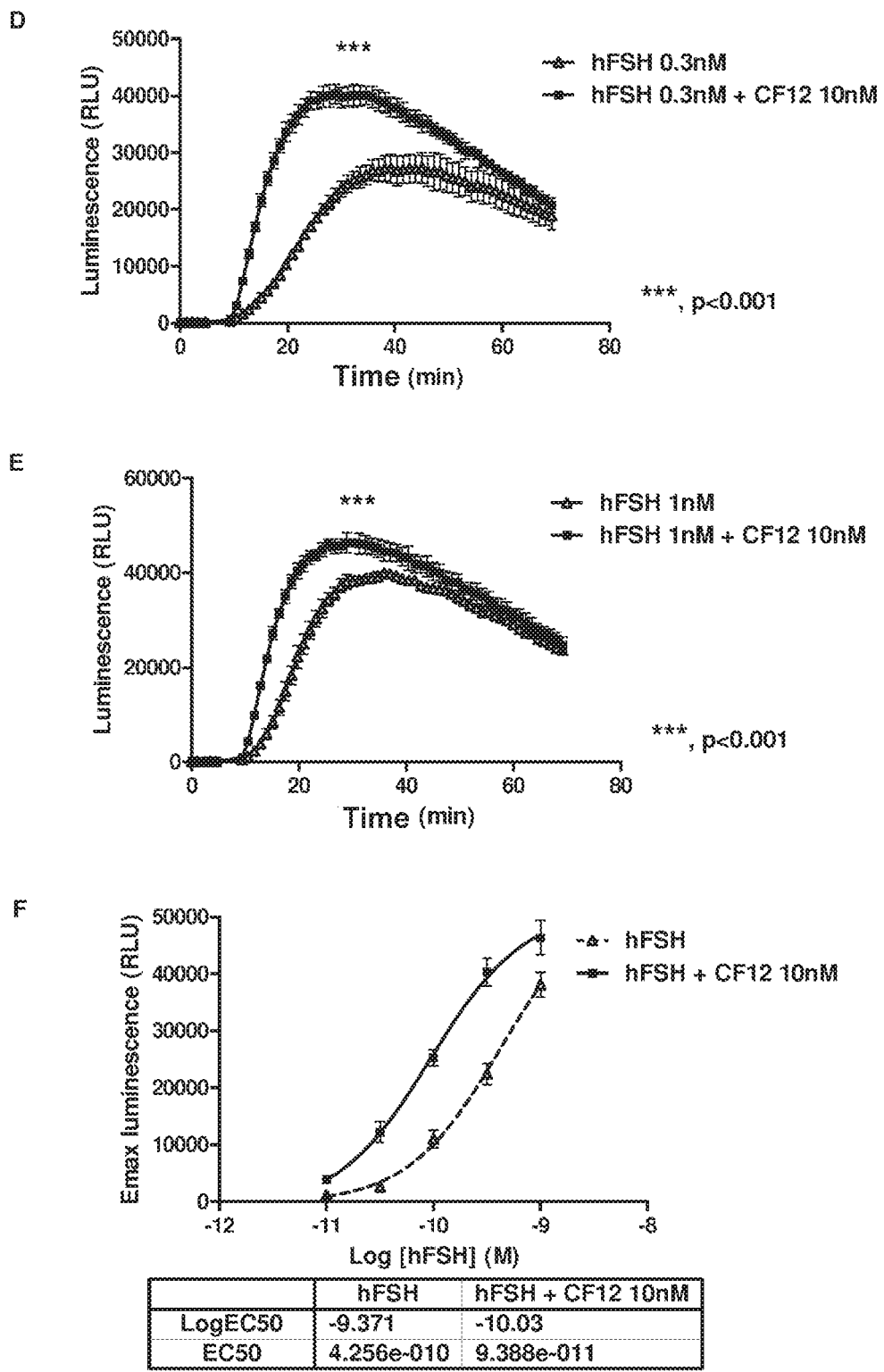
FIGURE 3 (end)

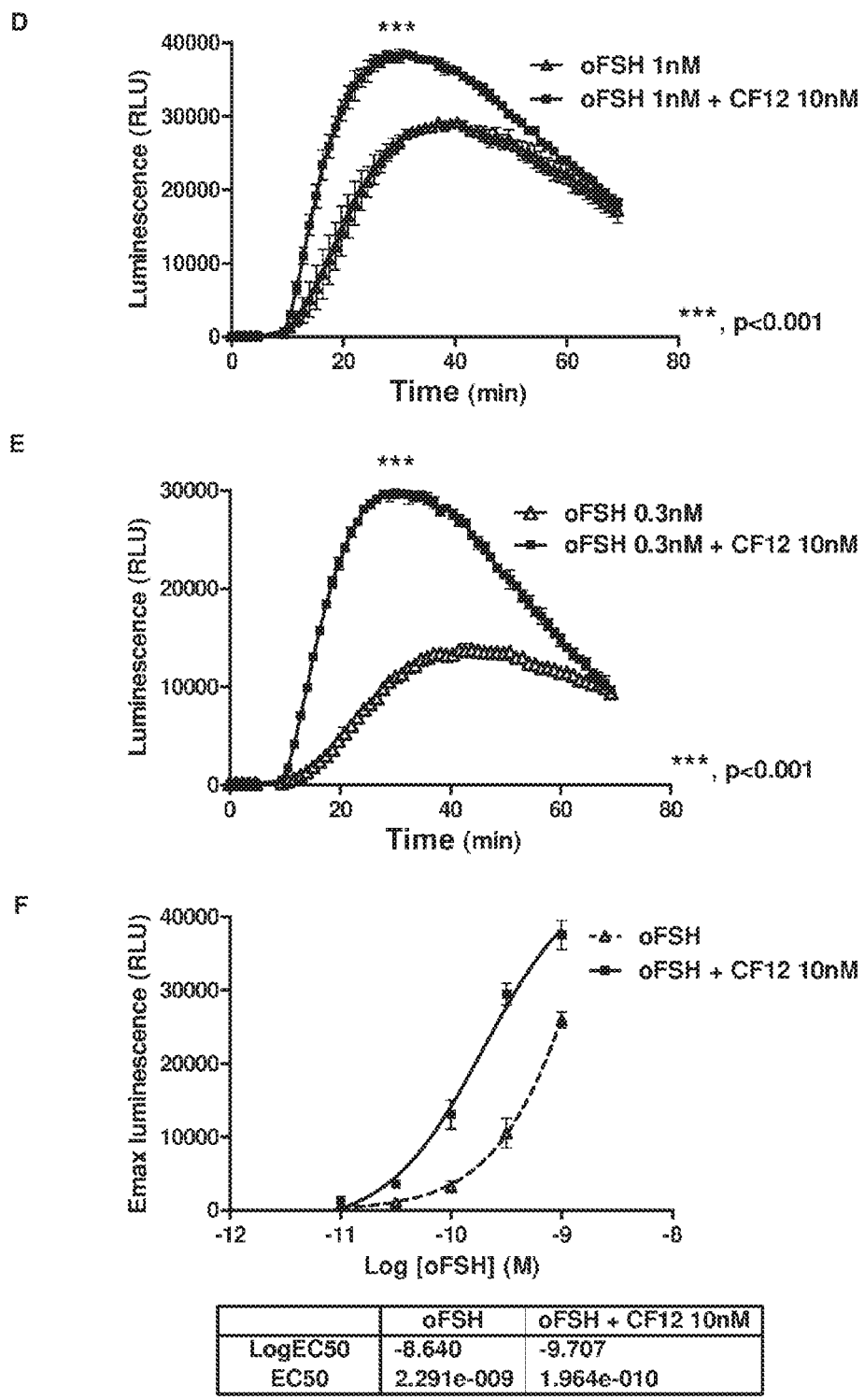
FIGURE 5 (end)

D
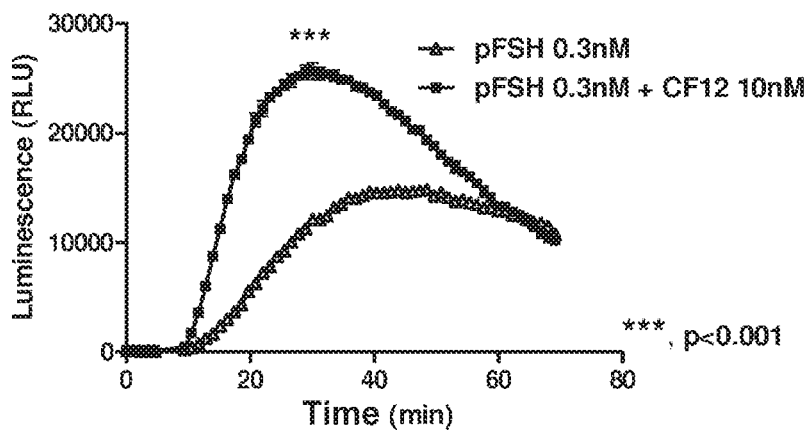
E
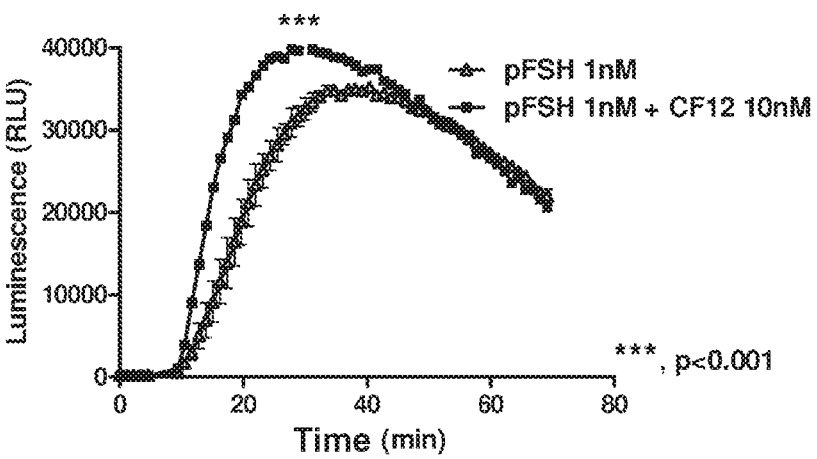
F
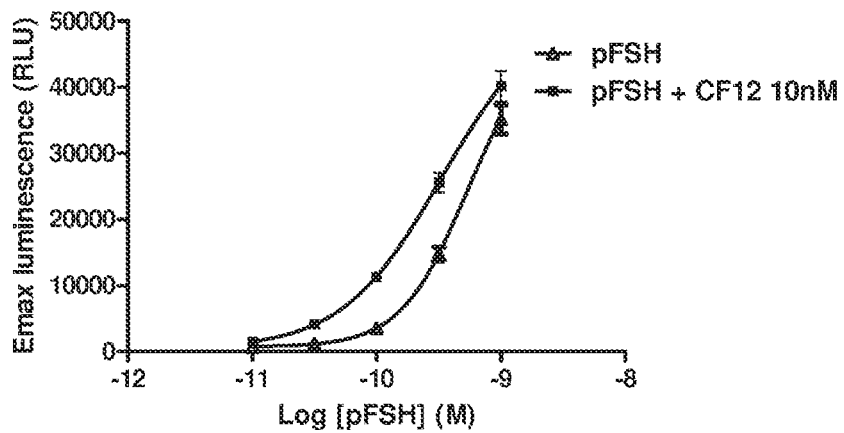
FIGURE 6 (end)

A
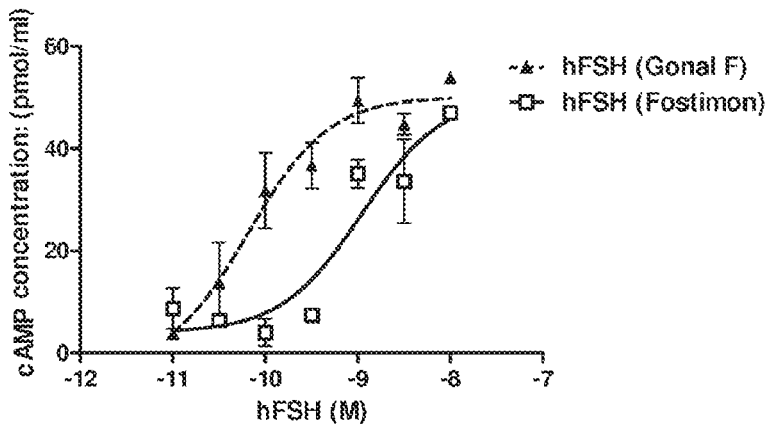
B
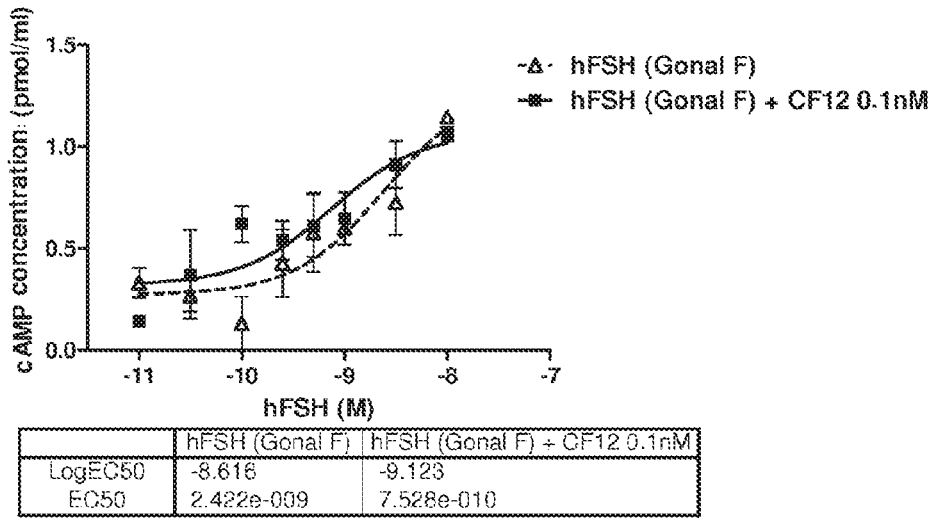
C
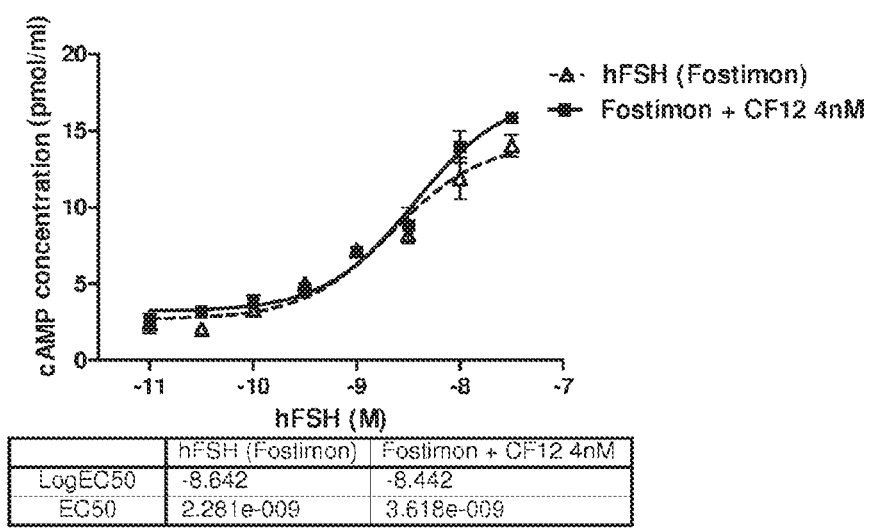
FIGURE 7

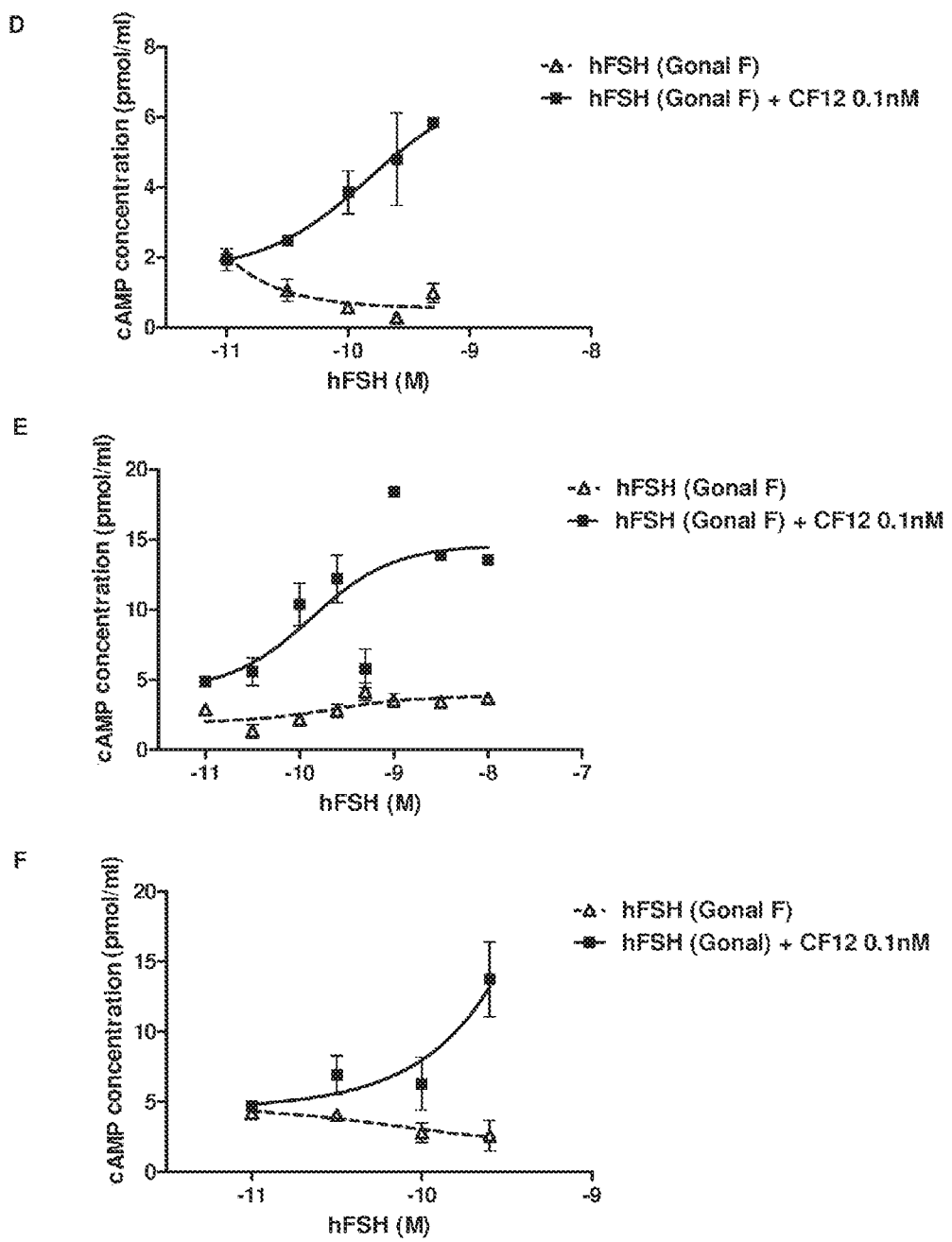
FIGURE 8 (end)

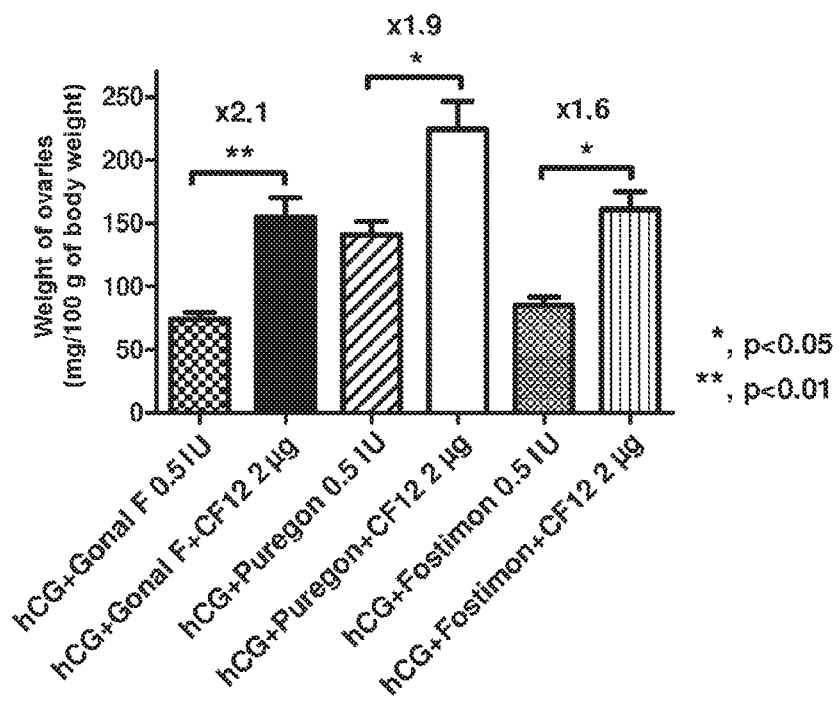
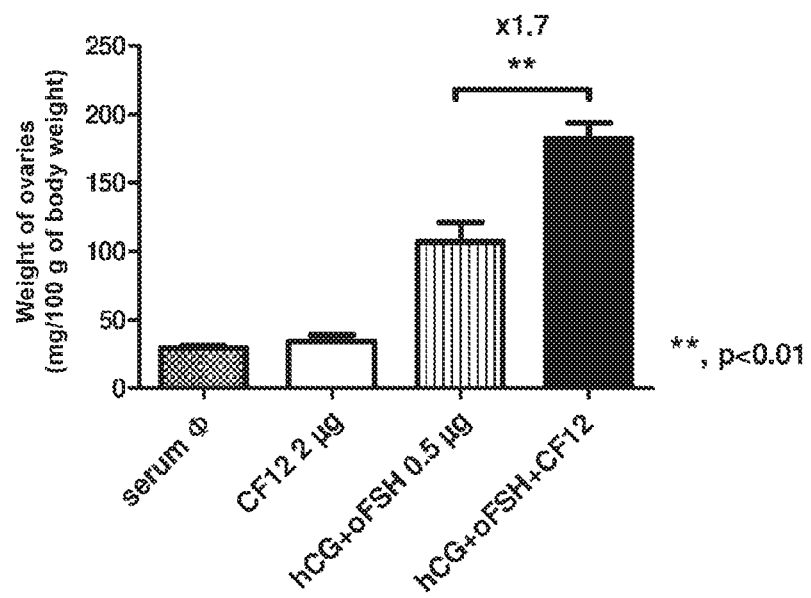
FIGURE 9

Epitope regions of the CF12 antibody on the alpha-subunits of human, ovine and porcine FSH and LH and human CG

```
                        1              10        20          30          40
hFSH  (SEQ ID NO: 33)  APD----V QDCP E CTLQ ENPLFSQPGAPILQC M GCC F S R AYPTPLR
hCG   (SEQ ID NO: 33)  APD----V QDCP E CTLQ ENPFFSQPGAPILQC M GCC F S R AYPTPLR
hLH   (SEQ ID NO: 33)  APD----V QDCP E CTLQ ENPFFSQPGAPILQC M GCC F S R AYPTPLR
oLH   (SEQ ID NO: 34)  FPDGEFTM QGCP E CKLK ENKYFSKPDAPIYQC M GCC F S R AYPTPAR
pLH   (SEQ ID NO: 35)  FPDGEFTM QGCP E CKLK ENKYFSKLGAPIYQC M GCC F S R AYPTPAR
oFSH  (SEQ ID NO: 34)  FPDGEFTM QGCP E CKLK ENKYFSKPDAPIYQC M GCC F S R AYPTPAR
pFSH  (SEQ ID NO: 35)  FPDGEFTM QGCP E CKLK ENKYFSKLGAPIYQC M GCC F S R AYPTPAR 50             60             70             80         90
hFSH  SKKTMLVQKNVTS E STCCVAKSYNRVTVMGGFKVENHT A CHCSTCYYHKS
hCG   SKKTMLVQKNVTS E STCCVAKSYNRVTVMGGFKVENHT A CHCSTCYYHKS
hLH   SKKTMLVQKNVTS E STCCVAKSYNRVTVMGGFKVENHT A CHCSTCYYHKS
oLH   SKKTMLVPKNITS E ATCCVAKAFTKATVMGNVRVENHT E CHCSTCYYHKS
pLH   SKKTMLVPKNITS E ATCCVAKAFTKATVMGNARVENHT E CHCSTCYYHKS
oFSH  SKKTMLVPKNITS E ATCCVAKAFTKATVMGNVRVENHT E CHCSTCYYHKS
pFSH  SKKTMLVPKNITS E ATCCVAKAFTKATVMGNARVENHT E CHCSTCYYHKS
```

Epitope regions of the CF12 antibody on the beta-subunits of human, ovine and porcine FSH and LH and human CG

```
                          1         10           20            30           40
hFSH  (SEQ ID NO: 36)  -----  -NS CEL TNIT IAIEKEECRFCISINTTWC AGY C Y TRDLVYKDPA
hCG   (SEQ ID NO: 37)  SKEPL  RPR CRP INAT LAVEKEGCPVCITVNTTIC AGY C P TMTRVLQGVL
hLH   (SEQ ID NO: 38)  SREPL  RPW CHP INAI LAVEKEGCPVCITVNTTIC AGY C P TMMRVLQAVL
oLH   (SEQ ID NO: 39)  SRGPL  RPL CQP INAT LAAEKEACPVCITFTTSIC AGY C L SMKRVLPVIL
pLH   (SEQ ID NO: 40)  SRGPL  RPL CRP INAT LAAENEACPVCITFTTSIC AGY C P SMVRVLPAAL
oFSH  (SEQ ID NO: 41)  ------ --S CEL TNIT ITVEKEECSFCISINTTWC AGY C Y TRDLVYKDPA
pFSH  (SEQ ID NO: 42)  ------ ---  CEL TNIT ITVEKEECNFCISINTTWC AGY C Y TRDLVYKDPA 50            60           70           80           90         100
hFSH  RPKIQKTCTFKELVYETVRVPGCAHHADSLYTYPVATQCHCGKCDSDSTDCTVRGL GPS YCSFG EM
hCG   PALPQVVCNYRDVRFESIRLPGCPRGVNPVVSYAVALSCQCALCRRSTTDCGGPKD HPL TCDDP RF
hLH   PPLPQVVCTYRDVRFESIRLPGCPRGVDPVVSFPVALSCRCGPCRRSTSDCGGPKD HPL TCDHP QL
oLH   PPMPQRVCTYHELRFASVRLPGCPPGVDPMVSFPVALSCHCGPCRLSSTDCGGPRT QPL ACDHP PL
pLH   PPVPQPVCTYRELSFASIRLPGCPPGVDPTVSFPVALSCHCGPCRLSSSDCGGPRA QPL ACDRP LL
oFSH  RPNIQKACTFKELVYETVKVPGCAHHADSLYTYPVATECHCGKCDRDSTDCTVRGL GPS YCSFS DI
pFSH  RPNIQKTCTFKELVYETVKVPGCAHHADSLYTYPVATECHCGKCDSDSTDCTVRGL GPS YCSFS EM
                                                                    <----------->
                                                                     seat belt 110
hFSH  KE---------------
hCG   QDSSSSKAPPPSLPSPS
hLH   SGLLFL-----------
oLH   PDILFL-----------
pLH   PGLLFL-----------
oFSH  RE---------------
pFSH  KE---------------
```

Epitope regions of the CF12 antibody on the human FSH receptor (N-Terminal region)

```
                          1        10           20           30           40
hFSHR (SEQ ID NO: 49)  CHHRIC HCSN RVFLCQESKVTEIPSDLPRNAIELRFVLTKLRVIQKGAF...
```

LIGANDS THAT POTENTIATE THE BIOACTIVITY OF GONADOTROPINS

CROSS REFERENCE TO RELATED APPLICATIONS

This is a U.S. national stage of application No. PCT/FR2015/052413, filed on Sep. 10, 2015. Priority under 35 U.S.C. § 119(a) and 35 U.S.C. § 365(b) is claimed from French Application No. 1458469 filed on Sep. 10, 2014, the disclosure of which is also incorporated herein by reference in its entirety.

TECHNICAL FIELD

The present invention relates to antibodies directed against follicle-stimulating hormone (FSH) and capable of potentiating the bioactivity of gonadotropins.

The present invention has its applications mainly in human and veterinary medicine, for inducing ovulation in a female mammal.

In the description below, the references between ([ ]) refer to the list of references presented at the end of the text.

BACKGROUND

Gonadotropins (or gonadotrophins) are complex glycoprotein hormones which play a central role in the regulation of reproduction in vertebrates by acting on the functions of the gonads (ovaries and testicles). Two of these hormones are secreted in all vertebrates: luteinizing hormone (LH) and follicle-stimulating hormone (FSH). In two groups of mammals, members of the horse family and primates, there is also a chorionic gonadotropin (CG) secreted by the placenta: human chorionic gonadotropin (hCG) and equine chorionic gonadotropin (eCG) which both act via LH receptors.

Luteinizing hormone (LH) is produced by the gonadotropic cells of the anterior lobe of the pituitary gland under stimulation from GnRH, itself produced by the hypothalamus. LH stimulates testosterone production in males, whereas it is involved in modifications of the ovarian cycle in females where it is responsible for terminal follicular growth and for ovulation and then for conversion of the ruptured ovulatory follicle into the corpus luteum. During the luteal phase of the menstrual cycle, LH stimulates progesterone secretion by the corpus luteum, essential for the early development and implantation of the embryo. LH consists of an α-subunit common to all the glycoprotein hormones of one and the same species (such as FSH, CG and thyroid-stimulating hormone, TSH), and of a β-subunit responsible for the specificity of activity of the hormone; activity which exists only if the two subunits are noncovalently linked in the form of a dimer.

Follicle-stimulating hormone (or FSH) is produced by the anterior pituitary gland under stimulation from GnRH produced by the hypothalamus. In males, it stimulates the Sertoli cells essential for spermatogenesis. In females, it is responsible for the recruitment of immature primordial follicles, for their growth and for their differentiation into pre-ovulatory follicles by stimulating the FSH receptors of the granulosa cells. FSH consists of two subunits, α and β, and has a structure similar to that of LH. Only the dimer is capable of stimulating FSH receptors.

In females, the LH and FSH levels are cyclical: very low during the period of sexual rest or outside the ovulatory period, with a secretion peak in the preovulatory period.

Gonadotropins are used in veterinary and human medicine, to induce ovulation in female mammals. Although effective, these treatments present a health risk because of the use of hormones extracted from biological fluids (blood, urine) or from tissues (pituitary glands), particularly in the veterinary field. This is the case with equine chorionic gonadotropin (eCG) extracted from gravid mare blood, and with a porcine LH and FSH extracted from pig pituitary glands. In the veterinary field, an hCG extracted from urine from pregnant women, Chorulon® (MSD laboratory) is also used.

In the human clinical field, and particularly the field of Assisted Reproductive Technology (or ART), hormones extracted from urine from menopausal women, such as Fostimon® (Laboratoire Genévrier) which is a purified FSH, and Menopur® (Ferring Pharmaceuticals laboratory), which is an hMG (human menopausal gonadotropin), a mixture of FSH and LH and the chorionic gonadotropin Endo5000, which is a purified hCG (Schering-Plough laboratory), are used. Use is also made of recombinant human FSHs, such as Gonal-F® (Merck Serono laboratory) and Puregon® (Merck Schering-Plough laboratory); and recombinant hCG and LH such as Ovidrel® and Luveris® (Merck Serono laboratory).

In addition, repeated use of these hormones usually causes an immune reaction which neutralizes the effect of the hormones, thus resulting in a decrease in therapeutic efficacy. However, it has also been demonstrated in some cases that the immune reaction can produce antibodies capable of potentiating the activity of the hormone when it is co-administered (patent EP 1 518 863) [1]. Since then, three anti-LH monoclonal antibodies capable of potentiating its action, and also that of FSH for two of them, have also been demonstrated (international application WO 2012/066519) [2].

SUMMARY

The inventors have now obtained monoclonal antibodies produced against the β-subunit of FSH, which are capable of potentiating its action and also that of LH and of hCG.

These monoclonal antibodies are called CF12.

The hybridoma which produces the CF12 antibody was deposited, in accordance with the Treaty of Budapest, on Oct. 3, 2013 with the CNCM (Collection Nationale de Culture de Microorganismes [French National Collection of Microorganism Cultures], Institut Pasteur, 25 rue du Docteur Roux, 75724 Paris Cedex 15, France), under number CNCM I-4803.

The nucleotide sequences of the heavy and light chain variable regions of the CF12 antibody have been determined, and the corresponding peptide sequences have been deduced. They are presented in table 1 below.

TABLE 1

| CF12 monoclonal antibody | |
| --- | --- |
| Heavy chain (VH) | |
| Nucleotide sequence (SEQ ID NO: 1) | CAGGGTCAGATGCAGCAGTCTGGAGCTGAG<br>CTGGTGAAGCCTGGGGCTTCAGTGAAGCTG<br>TCCTGCAAGACTTCTGGCTTCACCTTCAGC<br>AGTAGCTATATAAGTTGGTTGAAGCAAAAG<br>CCTGGACAGAGTCTTGAGTGGATTGCATGG<br>ATTTATGCTGGAACTGGTGGTACTAGCTAT<br>AATCAGAAGTTCACAGGCAAGGCCCAACTG<br>ACTGTAGACACATCCTCCAGCACAGCCTAC |

TABLE 1-continued

CF12 monoclonal antibody

|  |  |
|---|---|
|  | ATGCAATTCAGCAGCCTGACAACTGAGGAC<br>TCTGCCATCTATTACTGTGCAAGACACGGG<br>TCCTACTTTGACTACTGGGGCCAAGGCACC<br>ACTCTCACAGTCTCCTCA |
| Peptide<br>sequence<br>(SEQ ID NO: 2) | QGQMQQSGAELVKPGASVKLSCKTSGFTFS<br>SSYISWLKQKPGQSLEWIAWIYAGIGGISY<br>NQKFIGKAQLTVDTSSSTAYMQFSSLITED<br>SAIYYCARHGSYFDYWGQGTTLTVSS |

Light chain (VL)

| Nucleotide<br>sequence<br>(SEQ ID NO: 3) | GACATTGTGCTGACCCAATCTCCAGCTTCT<br>TTGGCTGTGTCTCTAGGGCAGAGGGCCACC<br>ATCTCCTGCAAGGCCAGCCAAAGTGTTGAT<br>TATGATGGTGATAGTTATATGAACTGGTAC<br>CAACAGAAACCAGGACAGCCACCCAAACTC<br>CTCATCTATGCTGCATCCAATCTAGAATCT<br>GGGATCCCAGCCAGGTTTAGTGGCAGTGGG<br>TCTGGGACAGACTTCACCCTCAACATCCAT<br>CCTGTGGAGGAGGAGGATGCTGCAACCTAT<br>TACTGTCAGCAAAGTAATGAGGATCCGTAC<br>ACGTTCGGAGGGGGGACCAAGCTGGAAATA<br>AAA |
|---|---|
| Peptide<br>sequence<br>(SEQ ID NO: 4) | DIVLTQSPASLAVSLGQRATISCKASQSVD<br>YDGDSYMNWYQQKPGQPPKLLIYAASNLES<br>GIPARFSGSGSGTDFTLNIHPVEEEDAATY<br>YCQQSNEDPYTFGGGTKLEIK |

The sequences encoding the CDRs (complementarity determining regions) have been determined from the sequences of the variable regions of the heavy (VH-CDR) and light (VL-CDR) chains of the CF12 antibody above. The corresponding peptide sequences have been deduced and are presented respectively in table 2 below.

TABLE 2

CF12 monoclonal antibody

| VH-CDR1 (SEQ ID NO: 5) | GFTFSSSY |
|---|---|
| VH-CDR2 (SEQ ID NO: 6) | IYAGTGGT |
| VH-CDR3 (SEQ ID NO: 7) | ARHGSYFDY |
| VL-CDR1 (SEQ ID NO: 8) | QSVDYDGDSY |
| VL-CDR2 | AAS |
| VL-CDR3 (SEQ ID NO: 9) | QQSNEDPYT |

A subject of the present invention is a follicle-stimulating hormone (FSH) ligand which potentiates the bioactivity of FSH, of luteinizing hormone (LH) and of chorionic gonadotropin (CG), characterized in that it comprises the paratope of an anti-FSH β-subunit antibody.

For the purposes of the present invention, the term "anti-FSH β-subunit antibody" is intended to mean any antibody obtained by immunization of an animal on the basis of primary injections of FSH followed by several boosters with injection of the FSH β-subunit. The injections can be given using FSH from various mammals, for example ovine, human, bovine, caprine or porcine, equine, canine, murine, etc., FSH and β-subunits of FSH of homologous or heterologous origin. Thus, the CF12 monoclonal antibody was obtained following an immunization using human FSH and human FSH β-subunit.

In particular, a subject of the present invention is thus a ligand according to the invention, characterized in that:

the heavy chain variable domain contains the following CDRs:

VH-CDR1, defined by the sequence GFTFSSSY (SEQ ID NO: 5);

VH-CDR2, defined by the sequence IYAGTGGT (SEQ ID NO: 6);

VH-CDR3, defined by the sequence ARHGSYFDY (SEQ ID NO: 7); and the light chain variable domain contains the following CDRs:

VL-CDR1, defined by the sequence QSVDYDGDSY (SEQ ID NO: 8);

VL-CDR2, defined by the sequence AAS;

VL-CDR3, defined by the sequence QQSNEDPYT (SEQ ID NO: 9).

For the purposes of the present invention, the term "CDR" is intended to mean the three hypervariable regions of the variable regions of the heavy and light chains of an antibody which constitute the elements of the paratope and make it possible to determine the complementarity of the antibody with the epitope of the antigen. These three hypervariable regions are framed by four constant regions which constitute the "framework" regions (FRs) and give the variable domain a stable configuration.

A ligand according to the present invention is for example:

the CF12 monoclonal antibody produced by the CNCM I-4803 hybridoma;

a VH or VL fragment of an antibody above used alone or as a mixture;

a Fab, Fab', F(ab')2, Fv, dsFv or scFv fragment or a nanobody of an antibody above. Preferably, it is a Fab fragment or an scFv fragment;

a bivalent, trivalent or tetravalent form (diabodies, triabodies, tetrabodies) of two, three or four scFv fragments, respectively;

a recombinant antibody comprising the paratope of an antibody above and the constant regions of which have been modified so as to minimize the immunogenicity with respect to the animal or the human being for which it is intended. For example, it is a chimeric (humanized, ovinized, caprinized, bovinized, porcinized, etc.) or entirely humanized, ovinized, caprinized, bovinized, porcinized antibody.

By way of nonlimiting example, the nucleotide sequences of scFvs derived from the CF12 antibody have been determined, and the corresponding peptide sequences deduced, and are presented respectively in table 3 below.

TABLE 3

CF12 scFv

| Nucleotide<br>sequence<br>(SEQ ID NO: 10) | CAGGTGCAGCTGCAGCAGTCGGGTGGCGC<br>AGAGCTGGTGAAACCGGGTGCGAGCGTTA<br>AACTGAGCTGCAAAACTAGCGGCTTTACC<br>TTTAGCTCGTCATATATTTCGTGGCTGAA<br>GCAGAAACCGGGCCAGTCACTGGAATGGA<br>TTGCGTGGATCTACGCAGGCACGGGTGGC<br>ACCTCATATAATCAGAAATTCACCGGTAA<br>AGCGCAACTGACGGTCGATACCAGCAGCA<br>GCACGGCGTACATGCAGTTCAGCTCGCTG<br>ACCACTGAAGATAGCGCAATCTACTATTG<br>TGCACGCCATGGTTCGTACTTCGACTATT<br>GGGGCCAGGGCACCACCCTGACCGTTTCA<br>AGCGGTGGTGGTGGTAGCGGTGGTGGTGG<br>TTCAGGTGGCGGCGGCTCAGATATTCAGA<br>TGACCCAGACCCCTGCGAGCCTGGCAGTG<br>TCACTGGGCCAACGCGCAACCATCTCGTG<br>TAAAGCCTCGCAGAGCGTGGATTATGACG |
|---|---|

TABLE 3-continued

| CF12 scFv | |
|---|---|
| | GCGATAGCTACATGAACTGGTATCAGCAA<br>AAGCCTGGTCAACCGCCGAAGCTGCTGAT<br>TTACGCCGCCAGCAACCTGGAATCGGGCA<br>TCCCGGCCCGTTTTAGCGGCTCAGGCTCG<br>GGTACTGACTTCACGCTGAACATTCACCC<br>GGTAGAAGAAGAAGACGCGGCCACGTATT<br>ACTGCCAGCAAAGCAATGAAGACCCGTAC<br>ACTTTTGGCGGCGGCACGAAACTCGAGAT<br>CAAACACCATCACCATCACCATTAACTCG<br>AGATCAAGTAA |
| Peptide sequence (SEQ ID NO 11) | QVQLQQSGGAELVKPGASVKLSCKTSGFT<br>FSSSYISWLKQKPGQSLEWIAWIYAGIGG<br>ISYNQKFIGKAQLTVDTSSSTAYMQFSSL<br>ITEDSAIYYCARHGSYFDYWGQGTTLTVS<br>SGGGGSGGGGSGGGGSDIQMTQTPASLAV<br>SLGQRATISCKASQSVDYDGDSYMNWYQQ<br>KPGQPPKLLIYAASNLESGIPARFSGSGS<br>GTDFTLNIHPVEEEDAATYYCQQSNEDPY<br>TFGGGTKLEIKHHHHHH |

A subject of the present invention is also a nucleotide sequence encoding a ligand according to the invention.

A subject of the present invention is also a recombinant vector, in particular an expression vector, comprising a nucleotide sequence according to the invention.

A subject of the present invention is also a host cell comprising a nucleotide sequence according to the invention or a recombinant vector according to the invention. For example, it is the CNCM I-4803 hybridoma or a cell transformed with a nucleotide sequence or a recombinant vector according to the invention.

A subject of the present invention is also a method for producing a ligand according to the invention, characterized in that it comprises culturing host cells according to the invention in an appropriate medium, and recovering said ligand from said culture.

The inventors have demonstrated that the CF12 antibody potentiates little, although significantly, porcine, ovine and bovine FSH, contrary to human FSH that it strongly potentiates. In addition, the inventors have demonstrated that the scFv derived from the CF12 antibody has the same binding and potentiating properties as the antibody from which it is derived.

A subject of the present invention is also a ligand according to the invention for use as a medicament, in particular for potentiating the bioactivity of FSH, of LH and of chorionic gonadotropin (CG) for inducing ovulation in a female mammal and for reducing hormone-dependent infertility or hypofertility problems in a male or female mammal.

A subject of the present invention is also a complex formed from a ligand and from a gonadotropin, or from an active peptide thereof, capable of binding to said ligand and the activity of which is potentiated by said ligand. For example, it is the complex of a ligand with LH, with the chorionic gonadotropin (CG) hormone or with FSH which have been extracted from biological tissues or fluids or which are recombinant, or an active peptide thereof capable of binding to said ligand and the activity of which is potentiated by said ligand.

A subject of the present invention is also a ligand or complex according to the invention for use as a medicament, in particular for potentiating the bioactivity of FSH, of LH and of chorionic gonadotropin (CG) for inducing ovulation or even polyovulation in a female mammal or for reducing hormone-dependent infertility or hypofertility problems in a male or female mammal. Said medicament also makes it possible to increase the level of circulating endogenous progesterone secreted by one or more corpora lutea in a female mammal, thus promoting early embryonic development and reducing the risk of abortion.

A subject of the present invention is also a method for meat production, wherein said method comprises the administration of ligand and/or of complex of the invention to a non-human animal female mammal.

A subject of the present invention is also a ligand and/or complex of the invention for use in the treatment of hormone-dependent infertility or hypofertility in a mammal. In the case of a female mammal suffering from infertility or hypofertility, the administration of the ligand or complex of the invention will make it possible to stimulate a natural, medically assisted or artificial procreation. It should be noted that the administration of the ligand or complex of the invention to a healthy female mammal will also make it possible to trigger ovulation in the context of natural or artificial procreation.

For the purposes of the present invention, the term "hormone-dependent infertility/hypofertility" is intended to mean infertility/hypofertility due to hormonal insufficiency, for example low circulating concentrations of FSH and LH or an absence of these hormones resulting, for example, from an external cause (for example pesticides) or an internal cause (for example, pituitary or hypothalamic insufficiency or a problem of gonad receptiveness to LH and/or FSH due to an abnormality of LH, FSH or CG receptors or gonadotropins, for example a receptor mutation or polymorphism).

The ligands and complexes of the invention can be used in humans or animals, in particular members of the ovine, bovine, caprine, equine, porcine, murine, canine, camel, etc. families.

The ligands, the hormones or the complexes according to the invention can be administered either separately, or sequentially, or jointly, by injection, for example intramuscular, intravenous, intraperitoneal, subcutaneous, transcutaneous, intradermal, intraorbital, intraocular or ophthalmic injection, or via the transocular route, without modifying their potentiating effect.

A subject of the present invention is also a pharmaceutical composition comprising a ligand or a complex of the invention and a pharmaceutically acceptable carrier. Said pharmaceutical composition can also comprise an FSH and/or an LH and/or a chorionic gonadotropin (CG) hormone.

Other advantages may further emerge to those skilled in the art on reading the examples below, illustrated by the appended figures, given by way of illustration.

BRIEF DESCRIPTION OF THE FIGURES

FIG. 7A represents in vitro cell response of a patient to stimulation with Gonal-F or with Fostimon. FIGS. 7B and 7C represent the in vitro potentiating effect of the CF12 monoclonal antibody on the bioactivity of the human FSHs (hFSH) Gonal-F® (B) and Fostimon® (C) on human granulosa cells.

FIG. 9 represents the in vivo potentiating effect of the CF12 monoclonal antibody on the bioactivity of the human FSHs (hFSH) Gonal-F®, Puregon® and Fostimon® (A) and of ovine FSH (oFSH) (B) in the female rat.

FIG. 16 represents the conformational epitope of the CF12 ligand, on the hFSH, hCG, hLH, oLH, pLH, oFSH and pFSH hormones and the human FSH receptor.

DETAILED DESCRIPTION AND EXAMPLES

Figure 1:
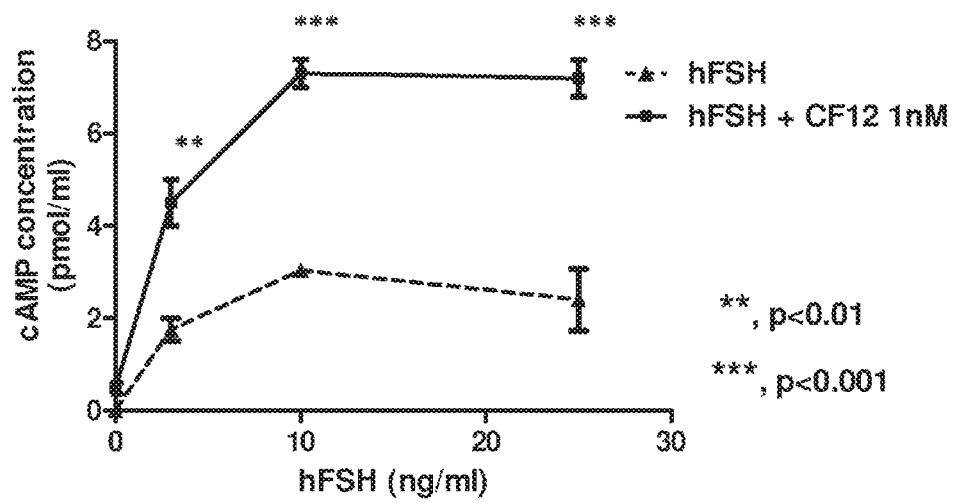
FIG. 1 illustrates the in vitro potentiating effect of the CF12 monoclonal antibody on the bioactivity of human FSH (hFSH), on bovine granulosa cells.

Example 1: Obtaining of the Ligands of the Invention, and Characterization Thereof 1/Mouse Immunization Strategy The injections were all carried out intraperitoneally on mice (Balb/C). Five mice were used.

Mouse Immunization Strategy for the CF12 Antibody

The immunization was carried out with several injections of recombinant human FSH (rhFSH). A first injection (D0) was carried out with 50 μg of rhFSH with complete Freund's adjuvant. Several booster injections were then carried out according to the following sequence:

D21 and D35: booster injection of 50 μg of rhFSH with incomplete Freund's adjuvant;

D55, D56 and D57: injection of 30 μg of rhFSH beta-subunit without adjuvant;

D58: fusion.

2/Isotyping

The isotyping of the CF12 antibody was carried out with the FastElysa isotyping kit sold by RD Biotech (reference RDB 3255) according to the manufacturers recommendations.

The CF12 antibody is an immunoglobin of IgM glass and of Kappa isotype. The optical density (OD) values obtained were 0.639 and 0.6 respectively.

3/Sequencing

The nucleotide sequences of the variable part of the heavy (VH) and light (VL) chains of the CF12 antibody secreted by the CNCM I-4803 hybridoma were determined from their messenger RNA (mRNA) according to the protocol below.

The RNAs were extracted from the cells using the Nucleospin® RNA kit (Macherey Nagel, Germany) according to the manufacturer's recommendations. The purified RNA concentrations were estimated by measuring the absorbance (A) at 260 nm and their quality was estimated by the A260 nm/280 nm ratio and visually after electrophoretic migration on an agarose gel.

The complementary DNAs of the mRNAs were then synthesized using an oligo-dT$_{18}$ as primer by reverse transcription reaction with the M-MLV enzyme (Ref. M1701, Promega, USA) according to the manufacturers recommendations.

The synthesis of the second DNA strand was carried out by a polymerase chain reaction (PCR) according to the following protocol: the following are added to 4 μl of the reverse transcription reaction in a final volume of 50 μl; the reaction buffer (1× final concentration), 200 μM of each dNTP, 300 nM of forward and reverse primers, 1.25 U of GoTaq polymerase (Ref M3175, Promega, USA).

For the amplification of the variable part of the light chains, 5 different primer pairs were used (MKRev2 to 8+MKC5For) and 2 pairs for those of the heavy chains (VHRev1 or VHRev2+MμCFor).

TABLE 4

Nucleotide sequences of the primers used for sequencing the heavy (VH) and light (VL) chains of the CF12 antibody.

| Name | 5'-3' Sequence | SEQ ID NO |
|---|---|---|
| Heavy chain (VH) | | |
| VHRev1 | CGGGATCCTCTAGAGGTCCAA CTGCAGGAGTCAGG | SEQ ID NO: 12 |
| VHRev2 | AGATCTAGAAAGCTTAGGTCA AGCTGCAGCAGTCAGG | SEQ ID NO: 13 |
| MμCFor | GGGGAAGACATTTGGGAAGG | SEQ ID NO: 14 |

TABLE 4-continued

Nucleotide sequences of the primers used for sequencing the heavy (VH) and light (VL) chains of the CF12 antibody.
CF12 antibody

| Name | 5'-3' Sequence | SEQ ID NO |
|---|---|---|
| Light chain (VL) | | |
| MKRev2 | GATATTGTGATGACGCAGGCT | SEQ ID NO: 15 |
| MKRev3 | GATATTGTGATAACCCAG | SEQ ID NO: 16 |
| MKRev4 | GACATTGTGCTGACCCAATCT | SEQ ID NO: 17 |
| MKRev5 | GACATTGTGATGACCCAGTCT | SEQ ID NO: 18 |
| MKRev8 | GACATCCAGCTGACTCAGTCT | SEQ ID NO: 19 |
| MKC5For | GGATACAGTTGGTGCAGCATC | SEQ ID NO: 20 |

TABLE 5

Nucleotide sequences of the primers used for sequencing the 5' part of the heavy (VH) and light (VL) chains of the CF12 antibody.
CF12 antibody

| Name | 5'-3' Sequence | SEQ ID NO |
|---|---|---|
| Heavy chain (VH) | | |
| CF12VH_Fw | CAGKAACTGCAGGTGTCCWCT | SEQ ID NO: 21 |
| CF12VH_Rev | CTGGAGGATGTGTCTACAGTCAG | SEQ ID NO: 22 |
| Light chain (VL) | | |
| CF12VL_Fw | CTGCTATGGGTGCTGCTGCTC | SEQ ID NO: 23 |
| CF12VL_Rev | AGATTGGATGCAGCATAGATGAG | SEQ ID NO: 24 |

The PCR program used is composed of an initial denaturation for 2 min at 95° C. followed by 30 cycles of denaturation for 30 sec at 95° C., hybridization for 30 sec at 47° C. and amplification for 1 min at 72° C. and, finally, a final amplification for 5 min at 72° C. The PCR products obtained were desalted with the QIAquick®Gel extraction kit (Ref 28704, Qiagen GmbH, Germany), then ligated with the pGEMT easy vector plasmid (Ref A1360, Promega, USA) so as to be transformed in bacteria. The plasmid DNA extracted from various bacterial clones was sent for sequencing analysis (Macrogen Europe, the Netherlands).

The 5'-terminal nucleotide sequences of the VH and VL of the CF12 antibody were subsequently determined through the design of specific primers anchored in the leader sequences of the cDNAs (Fw primer). These primers were designed following the identification of homology by alignment between the VL and VH sequences previously obtained and the database of the IMGT/V-QUEST software (Brochet et al., Nucl. Acids Res., 36: W503-508, 2008; Giudicelli et al., Cold Spring Harb Protoc., 2011(6): 695-715, 2011) [3, 4] and the extraction of the leader sequences of interest from IMGT/GENE-DB (Giudicelli et al., Nucl. Acids Res., 33: D256-261, 2005) [5]. The reverse (Rev) primers were designed in the previously determined respective VH and VL sequences of each of the antibodies. The protocol used to obtain the 5' part is the same as that described in the previous paragraph.

The consensus nucleotide sequences were deduced from the alignment of the sequences using the MultAlin software (Corpet, Nucl. Acids Res., 16(22): 10881-10890, 1988) [6]. The transcription into polypeptide sequences and the annotation of the CDRs were carried out using the IMGT/V-QUEST software. The results are presented in tables 6 and 7.

TABLE 6

Nucleotide and peptide sequences of the heavy (VH) and light (VL) variable parts of the CF12 antibody.
CF12 antibody

| | Heavy chain (VH) |
|---|---|
| Nucleotide sequence SEQ ID NO: 1 | CAGGGTCAGATGCAGCAGTCTGGAGCTGAG CTGGTGAAGCCTGGGGCTTCAGTGAAGCTG TCCTGCAAGACTTCTGGCTTCACCTTCAGC AGTAGCTATATAAGTTGGTTGAAGCAAAAG CCTGGACAGAGTCTTGAGTGGATTGCATGG ATTTATGCTGGAACTGGTGGTACTAGCTAT AATCAGAAGTTCACAGGCAAGGCCCAACTG ACTGTAGACACATCCTCCAGCACAGCCTAC ATGCAATTCAGCAGCCTGACAACTGAGGAC TCTGCCATCTATTACTGTGCAAGACACGGG TCCTACTTTGACTACTGGGGCCAAGGCACC ACTCTCACAGTCTCCTCA |
| Peptide sequence SEQ ID NO: 2 | QGQMQQSGAELVKPGASVKLSCKTSGFTFS SSYISWLKQKPGQSLEWIAWIYAGTGGTSY NQKFTGKAQLTVDTSSSTAYMQFSSLTTED SAIYYCARHGSYFDYWGQGTTLTVSS |
| | Light chain (VL) |
| Nucleotide sequence SEQ ID NO: 3 | GACATTGTGCTGACCCAATCTCCAGCTTCT TTGGCTGTGTCTCTAGGGCAGAGGGCCACC ATCTCCTGCAAGGCCAGCCAAAGTGTTGAT TATGATGGTGATAGTTATATGAACTGGTAC CAACAGAAACCAGGACAGCCACCCAAACTC CTCATCTATGCTGCATCCAATCTAGAATCT GGGATCCCAGCCAGGTTTAGTGGCAGTGGG TCTGGGACAGACTTCACCCTCAACATCCAT CCTGTGGAGGAGGAGGATGCTGCAACCTAT TACTGTCAGCAAAGTAATGAGGATCCGTAC ACGTTCGGAGGGGGGACCAAGCTGGAAATA AAA |
| Peptide sequence SEQ ID NO: 4 | DIVLTQSPASLAVSLGQRATISCKASQSVD YDGDSYMNWYQQKPGQPPKLLIYAASNLES GIPARFSGSGSGTDFTLNIHPVEEEDAATY YCQQSNEDPYTFGGGTKLEIK |

TABLE 7

CDRs of the heavy (VH) and light (VL) variable parts of the CF12 antibody

| VH-CDR1 (SEQ ID NO: 5) | GFTFSSSY |
|---|---|
| VH-CDR2 (SEQ ID NO: 6) | IYAGTGGT |
| VH-CDR3 (SEQ ID NO: 7) | ARHGSYFDY |
| VL-CDR1 (SEQ ID NO: 8) | QSVDYDGDSY |
| VL-CDR2 | AAS |
| VL-CDR3 (SEQ ID NO: 9) | QQSNEDPYT |

4/Construction, Production and Characterization of scFvs
a/Construction of the scFv Antibody Fragments The synthetic genes of the single-chain variable fragments (scFv) derived from the CF12 antibody were synthesized by ATG:Biosynthetics GmbH (Germany).

Each sequence was designed from the fusion of the heavy and light variable parts (SEQ ID NO: 1/SEQ ID NO: 3) linked by a sequence encoding the peptide (Gly$_4$Ser)$_3$ ensuring the functionality of the protein, and ending with a sequence encoding the His$_6$ peptide (HIS-tag peptide) that will allow purification of the scFvs. In order to enable their insertion into the expression plasmid, the sequences were flanked by the PstI and SalI restriction enzyme sites. An additional sequence was added between the 3' end of the VL and the SalI site allowing elimination of the Hiss peptide if desired. The codons were optimized for expression in *E. coli*. A diagrammatic representation of the construction of the scFvs synthetic genes is given in detail below:

| VH | Linker | VL | | |
|---|---|---|---|---|
| LQ...................... | (G$_4$S)$_3$ | ...........................LEIKH$_6$ | LEIK | VD |
| PstI | | .. XhoI | XhoI | SalI |

The antibody fragments were inserted between the PstI and XhoI enzymatic sites of the pSW1 expression plasmid (ATG:Biosynthetics GmbH, Germany) according to E. S. Ward et al. (Ward et al., Nature, 341: 544-546, 1989) [7] which contains, under the control of a LacZ inducible promoter, a PelB signal sequence which, fused in reading frame with the gene of the recombinant antibody fragment, allows trafficking of the synthesized protein to the bacterial periplasm. In the periplasm, this signal sequence is eliminated by a peptidase.

After verification, by sequencing, of the quality of the constructs, the pSW1-CA5, pSW1-CH10 and pSW1-CF12 plasmids were used to transform, by heat shock, HB2151 bacteria (T53040, Interchim, France) made competent (Li et al., Afr. J. Biotechnol., 9(50): 8549-8554, 2010) [8].

TABLE 8

Nucleotide and peptide
sequences of the CF12 scFv
CF12 scFv

| Nucleotide sequence SEQ ID NO: 10 | CAGGTGCAGCTGCAGCAGTCGGGTGGCGCAGA<br>GCTGGTGAAACCGGGTGCGAGCGTTAAACTGA<br>GCTGCAAAACTAGCGGCTTTACCTTTAGCTCG<br>TCATATATTTCGTGGCTGAAGCAGAAACCGGG<br>CCAGTCACTGGAATGGATTGCGTGGATCTACG<br>CAGGCACGGGTGGCACCTCATATAATCAGAAA<br>TTCACCGGTAAAGCGCAACTGACGGTCGATAC<br>CAGCAGCAGCACGGCGTACATGCAGTTCAGCT<br>CGCTGACCACTGAAGATAGCGCAATCTACTAT<br>TGTGCACGCCATGGTTCGTACTTCGACTATTG<br>GGGCCAGGGCACCACCCTGACCGTTTCAAGCG<br>GTGGTGGTGGTAGCGGTGGTGGTGGTTCAGGT<br>GGCGGCGGCTCAGATATTCAGATGACCCAGAC<br>CCCTGCGAGCCTGGCAGTGTCACTGGGCCAAC<br>GCGCAACCATCTCGTGTAAAGCCTCGCAGAGC<br>GTGGATTATGACGGCGATAGCTACATGAACTG<br>GTATCAGCAAAAGCCTGGTCAACCGCCGAAGC<br>TGCTGATTTACGCCGCCAGCAACCTGGAATCG<br>GGCATCCCGGCCCGTTTTAGCGGCTCAGGCTC<br>GGGTACTGACTTCACGCTGAACATTCACCCGG<br>TAGAAGAAGAAGACGCGGCCACGTATTACTGC<br>CAGCAAAGCAATGAAGACCCGTACACTTTTGG<br>CGGCGGCACGAAACTCGAGATCAAACACCATC<br>ACCATCACCATTAACTCGAGATCAAGTAA |
|---|---|

TABLE 8-continued

Nucleotide and peptide
sequences of the CF12 scFv
CF12 scFv

| Peptide sequence SEQ ID NO: 11 | QVQLQQSGGAELVKPGASVKLSCKTSGFTFSS<br>SYISWLKQKPGQSLEWIAWIYAGTGGTSYNQK<br>FTGKAQLTVDTSSSTAYMQFSSLTTEDSAIYY<br>CARHGSYFDYWGQGTTLTVSSGGGGSGGGGSG<br>GGGSDIQMTQTPASLAVSLGQRATISCKASQS<br>VDYDGDSYMNWYQQKPGQPPKLLIYAASNLES<br>GIPARFSGSGSGTDFTLNIHPVEEEDAATYYC<br>QQSNEDPYTFGGGTKLEIKHHHHHH |
|---|---| b/Production of the Recombinant Antibody Fragments
Bacterial Culture

A preculture was prepared in 5 ml of 2×YT medium containing 50 µg/ml of ampicillin overnight at 37° C. The following day, 500 µl of this preculture were inoculated into 500 ml of the same medium and grown at 37° C. at 150 RPM until an OD$_{600nm}$ of 1.4 was obtained. The synthesis of the scFv was induced adding 0.1 mM of IPTG for 16 h at 16° C. at 150 RPM.

Extraction

The culture medium was centrifuged for 30 min at 4500 g at 4° C. The remainder of the preparation was carried out at 4° C. To extract the bacterial periplasm, the pellet was resuspended and incubated in 10 ml of TES (0.2 M Tris, pH 8, 0.5 M EDTA, 0.5 M sucrose) for 30 min to which were then added 15 ml of TES diluted to ¼, followed by further incubation for 30 min. The bacterial extract was centrifuged for 30 min at 10 000 g. The supernatant was dialyzed against PBS overnight. The dialyzed supernatent was immediately treated in order to purify the scFv or stored at −20° C. until use.

The production of the scFv in the periplasm was analyzed by Western blotting using an anti-His-Tag HRP antibody (Ref R93125 Life Technologies, France) according to the manufacturers recommendations for use.

Purification

The periplasm was centrifuged for 20 min at 5 000 g at 4° C. The supernatant was incubated with HIS-Select® Nickel Affinity Gel (Sigma-Aldrich, MO, USA) with stirring for 1 h at 4° C. The gel was washed with a 0.05 M sodium phosphate buffer containing 0.3 M NaCl, pH 8, then the same buffer with 20 mM of imidazole added thereto, until an OD$_{280nm}$ close to 0 was obtained. The scFv was then eluted with a 0.05 M sodium phosphate buffer containing 0.3 M NaCl and 250 mM imidazole, pH 8. The eluate was dialyzed against PBS overnight. It is stored at −20° C.

Quality Control

The purified scFv was analyzed by electrophoresis on a 15% polyacrylamide gel after staining with Coomassie blue and by exclusion chromatography on a Sephadex™ 75 10/300 GL column (Ref 17-5174-01 GE Healthcare, Germany).

5/Specificity

The specificity of the CF12 antibody and of the scFv thereof was studied by the ELISA technique. Each hormone evaluated was prepared at the concentration of 10 μg/ml in a 0.1 M sodium carbonate buffer, pH 9.6, and distributed in a proportion of 100 μl per well on an ELISA plate. The adsorption time was 18 hours at +4° C. After five washes, the wells were treated with 100 μl of PBS supplemented with 0.1% Tween and 1% BSA for 45 minutes at 37° C., then each antibody or scFv was distributed in a proportion of 100 μl/well and incubated for one hour at 37° C. On each hormone evaluated, the antibody and the scFv were distributed at various concentrations according to a range of 10 to 250 μg/ml for the antibodies and of 10 to 150 or 200 μg/ml for the scFv.

After five washes, a secondary antibody coupled to peroxidase (HRP) was distributed in a proportion of 100 μl/well and incubated for one hour at 37° C. Depending on the isotype of the monoclonal antibody studied, the secondary antibody was an anti-IgG1 HRP (Ref. 115-035-205, Jackson ImmunoResearch Laboratories Inc), an anti-IgG2a HRP (Ref. 115-035-206, Jackson Laboratories) or an anti-IgM HRP (Ref. 115-035-075, Jackson Laboratories). For the scFvs, an anti-His Tag HRP (Ref. R93125 Life Technologies, France) was used. After five washes, the enzymatic activity was revealed with TMB distributed in a proportion of 100 μl/well. The revealing time was from 5 to 30 min at ambient temperature depending on the rate of the reaction. After the reaction had been stopped with 1 M $H_2SO_4$ (50 μl/well), the strength of the colored reaction (optical density) was measured using a spectrophotometer for ELISA plates.

Specificity of the CF12 scFv

The CF12 scFv made it possible to obtain binding quantifiable by an ELISA method, based on the revealing of the binding of the antibody, prepared at increasing concentrations, to various hormones adsorbed (binding up to saturation, Bmax). The results are expressed in optical density units obtained after revealing.

Table 9 represents the optical density values obtained with the CF12 scFv incubated at the concentration of 200 μg/ml on porcine FSH (pFSH) and ovine FSH (oFSH) and on various human FSHs.

TABLE 9

|  | oFSH | pFSH | hFSH (Gonal F) | hFSH (Puregon) | hFSH (Fostimon) | hMG (Menopur) |
|---|---|---|---|---|---|---|
| CF12 scFv | 2.3 | 2.5 | 0.5 | 0.9 | 0.5 | 0.8 |

The CF12 scFv exhibits strong binding to the pFSH and oFSH adsorbed, and weaker binding to the hFSHs and the hMG (Menopur).

Table 10 represents the optical density values obtained with the CF12 scFv incubated at the concentration of 200 μg/ml on porcine LH (pLH), ovine LH (oLH), bovine LH (bLH), eCG and the hCGs Chorulon and Endo 5000.

TABLE 10

|  | oLH | pLH | bLH | eCG | Chorulon | Endo 5000 |
|---|---|---|---|---|---|---|
| CF12 scFv | 2 | 2.2 | 2.2 | 0.6 | 0.35 | 0.38 |

The binding of the CF12 scFv to the animal LHs is considerable, unlike the hCGs and the eCG adsorbed, for which the binding is weaker.

The binding of CF12 and that of the CF12 scFv thus appear to be extremely restricted by the conformation of the epitope, particularly for the human hormones. Given the notable biological effects obtained with CF12 and its scFV, in vitro and in vivo on the activity of the human FSHs and of the hCGs Chorulon and Endo 5000 (see results in examples 2 and 3), it is probable that the binding of the CF12 scFv, just like that of the whole antibody, is totally dependent on the conformation of the hormone. The hypothesis of an impairment of the binding of CF12 and of the CF12 scFv due to a modification of the conformation of the hormones adsorbed onto the plastic of the ELISA plate may explain these results and reinforce the hypothesis that CF12 and its scFv are specific for an extremely conformational epitope.

An estimation of the dissociation constant Kd of the scFv, with respect to the various FSH, LH and CG studied, was calculated on GraphPad Prism (GraphPad Software Inc., San Diego, Calif., USA, version 5) using the "One site—Specific binding" function in a saturation binding model ("saturation binding experiment model", GraphPad PRISM software). The various values obtained are indicated in tables 11 and 12.

TABLE 11

|  | oFSH | pFSH | hFSH Gonal-F | hFSH Puregon | hFSH Fostimon | hMG Menopur |
|---|---|---|---|---|---|---|
| Kd ($10^{-6}$M) | 3.779 | 2.628 | 4.874 | 25.22 | 2.634 | 14.01 |

TABLE 12

|  | oLH | pLH | bLH | eCG | hCG Chorulon | hCG Endo 5000 |
|---|---|---|---|---|---|---|
| Kd ($10^{-6}$M) | 5.813 | 4.729 | 5.033 | 6.116 | 5.074 | 6.238 |

The comparison of the dissociation constants Kd thus estimated indicates a stronger affinity of the scFv for the ovine, porcine and human FSHs (Gonal-F and Fostimon) with a Kd value ranging from 2.6 μM for pFSH and hFSH Fostimon to 3.77 μM for oFSH and 4.87 μM for hFSH Gonal-F.

The Kd values for the animal LHs, eCG and the hCGs Chorulon and Endo 5000 are relatively homogeneous and vary between 4.72 and 6.23 μM, attesting to a slightly weaker affinity of the CF12 scFv for these hormones compared with the FSHs above.

With respect to the hFSH Puregon and the hMG Menopur, the CF12 scFv exhibits an even weaker affinity with a Kd of about 10 or so μM: 14 and 25.22 μM respectively.

Example 2: In Vitro Measurement of the Potentiating Effect of the Ligands of the Invention on the Bioactivity of FSH The demonstration of the potentiating effect of the ligands of the invention on the bioactivity of FSH was carried out by comparing the biological response obtained with various cell types or lines stimulated either with FSH alone or with the FSH/monoclonal antibody (MAb) complex.

In each of the cases, comparison of the dose-response curves obtained made it possible to quantify the potentiating effect in vitro of the MAb on the biological activity of the complexed FSH. The statistical analysis of the results was carried out using the Prism software (GraphPad Software Inc., San Diego, Calif., USA, version 5).

1/on Primary Cultures of Bovine Granulosa Cells

The potentiating effect of the CF12 MAb on human FSH (hFSH) was first of all characterized on bovine granulosa cells endogenously expressing the bovine FSH receptor.

Hybridoma supernatents at the final concentration of 0.1 µg/ml of CF12 antibody were incubated with a range of human FSH ranging from 3 ng/ml to 25 ng/ml, for 30 mn at 37° C.

The bovine granulosa cells were taken by ovarian puncture on cow ovaries from follicles having a diameter ranging from 2 to 6 mm, according to the protocol described by Chopineau et al. (Mol. Cell Endocrinol., 92(2): 229-39, 1993) [8] and Wehbi et al. (Endocrinology, 151(6): 2788-2799, 2010) [9]. The bovine granulosa cells in suspension in a McCoy's 5A medium (Lonza, Belgium, reference BE12-688F), prepared at 80 000 cells per 0.5 ml, were stimulated for 3 hours at 37° C., with stirring, in the presence of 48 µg/ml of IBMX (Sigma Aldrich, France, reference 15879), with a range of FSH of from 3 ng/ml to 25 ng/ml, alone or pre-complexed with a monoclonal antibody according to the protocol above. The biological response measured was cAMP secretion.

After centrifugation, the cAMP produced was assayed in the culture supernatent using an ELISA kit (Biomedical Technologies Inc., MA, USA, BT-730).

The results are presented in FIG. 1.

The results show a 2.5-fold amplification for CF12 on the activity of the human FSH. The statistical analysis by two-way analysis of variance (two-way ANOVA, GraphPad PRISM software) shows a significant effect ranging from $p<0.01$ () to $p<0.001$ (*) for CF12. The CF12 antibody has a significant effect for all of the hFSH concentrations tested.

2/On HEK293 Cell Lines Stably Transfected with the Human FSH Receptor

The potentiating effect of the MAbs on the FSH of various species was measured on HEK 293 cells stably expressing the human FSH receptor. This system made it possible to measure the cAMP production following activation of the FSH receptor after a stimulation with FSH alone or with the FSH/MAb complex for one hour at 37° C.

For this, 60 000 cells were distributed into wells of 96-well plates (Becton Dickinson, N.J., USA, reference 353072) and cultured for 24 h at 37° C., 5% $CO_2$ in a humid atmosphere, in 100 µl of MEM medium (Ozyme, France, reference BE12-611F) containing 10% SVF (Lonza, Belgium, reference DE14-801F), 1% penicillin/streptomycin (Sigma Aldrich, France, reference P-4333) and 400 µg/ml of G418 (Sigma Aldrich, France, reference A1720). After 2 h of weaning in MEM medium, the cells were stimulated for 1 h at 37° C. The culture supernatent was recovered and assayed using an ELISA kit (Biomedical Technologies Inc., MA, USA, BT-730). The results express the amount of cAMP secreted at the end point. They were analyzed using the Prism software (GraphPad Software Inc., San Diego, Calif., USA, version 5).

Figure 2:
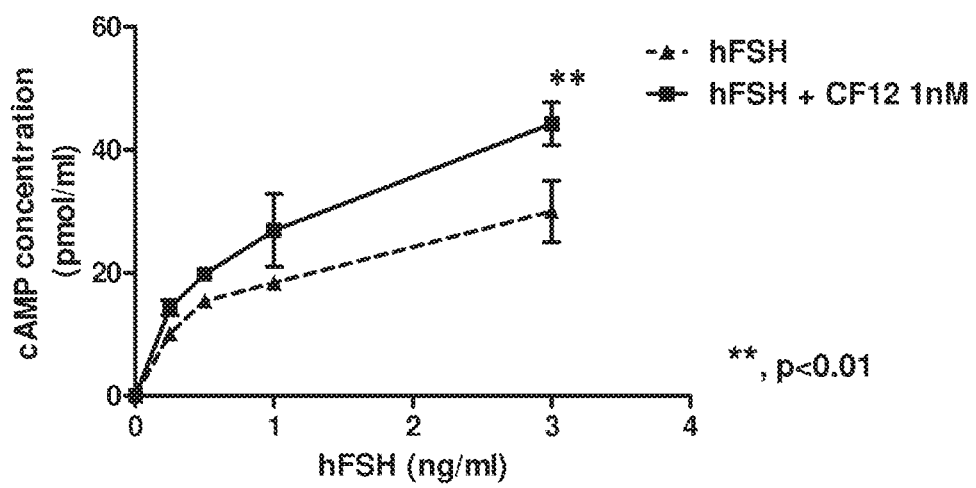
FIG. 2 represents the in vitro potentiating effect of the CF12 monoclonal antibody on the bioactivity of human FSH (hFSH) on an HEK 293 cell line stably transfected with the human FSH receptor.

FIG. 2 represents the potentiating effect of the CF12 monoclonal antibody on the bioactivity of human FSH in vitro on HEK 293 cells stably transfected with the human FSH receptor. For this, the cells were stimulated either with a range of from 0.3 ng/ml to 3 ng/ml for the human FSH (Gonal-F, Serono Laboratory), or with the same FSH range points previously incubated, for 30 minutes at 37° C., with the monoclonal antibody (final concentration 0.1 µg/ml) before the stimulation of the cells. A two-way analysis of variance (two-way ANOVA, GraphPad PRISM software) made it possible to compare the dose-response curves obtained with the FSH alone or with the FSH/monoclonal antibody complex. The results obtained with the recombinant human FSH (Gonal-F, Serono Laboratory) show that the CF12 antibody has a hormonal activity-potentiating effect of 140% at 0.5 ng/ml and 160% for the concentrations 1 and 3 ng/ml respectively. This effect is significant for the point 3 ng/ml of human FSH ($p<0.01$) by means of a paired t-test (Wilcoxon test).

3/On HEK293 Cell Line Stably Transfected with the Human FSH Receptor and with the Glosensor® System The potentiating effect of the MAbs on the FSHs of various species was measured in real time on HEK 293 cells stably expressing the human FSH receptor and the GloSensor™ vector (Promega, France). This cell system made it possible to monitor the cAMP production following stimulation of the FSH receptor with the agonist (FSH alone or FSH/monoclonal antibody complex) in real time. Following the binding of the cAMP on the GloSensor™ protein, the GloSensor™ substrate (Promega, France, reference E1291) was hydrolyzed and resulted in an emission of luminescence measured by means of a PolarStar Optima reader (BMG Labtech, Germany) and expressed in RLU (Relative Luminescence Units). This stable line was developed by the Biology and BioInformatics of Signaling Systems team at the INRA [French National Institute for Agronomic Research] center, Val de Loire, 37380 Nouzilly, France) and was kindly made available for these assays.

For this, the HEK 293 cells were cultured in a proportion of 80 000 cells per well of a transparent-bottom, white 96-well microplate (Dominique Dutscher, France, reference 655903) and cultured in 100 µl of MEM medium (Ozyme, France, reference BE12-611F) supplemented with 10% SVF (Lonza, Belgium, reference DE14-801F), 1% penicillin/streptomycin (Sigma Aldrich, France, reference P-4333), 200 µg/ml of hygromycin B (Life Technologies™, France, reference 10687010) and 400 µg/ml of G418 (Sigma Aldrich, France, reference A1720) overnight. After 2 h of weaning in 100 µl of MEM medium supplemented with 1% BSA (PAA, France, reference K45012) and containing 4% of GloSensor™ substrate for 2 h at ambient temperature in the dark, the plate of cells was placed in the PolarStar Optima reader and a first reading was carried out for 5 minutes in order to measure the basal level of luminescence. The plate was then removed from the reader and 11 µl of ligand (FSH alone or FSH/monoclonal antibody complex) were added thereto so as to obtain the concentrations indicated. The luminescence emitted was then measured for approximately 1 h 30.

The results obtained were analyzed using the Prism software (GraphPad Prism Software Inc., San Diego, Calif., USA, version 5). The non-linear function "log (agonist) versus response" was used to plot the response as a function of the FSH concentration. This made it possible to characterize and compare the EC50 for the FSH alone and the FSH complexed with the monoclonal antibody. For each example, the significant effect of the FSH/potentiating antibody complex was measured by two-way analysis of variance (two-way ANOVA, GraphPad PRISM software) by comparing the two curves in their entirety.

CF12 Monoclonal Antibody

The potentiating effect of the CF12 monoclonal antibody was characterized on the bioactivity of human, ovine and porcine FSH.

Figure 3:
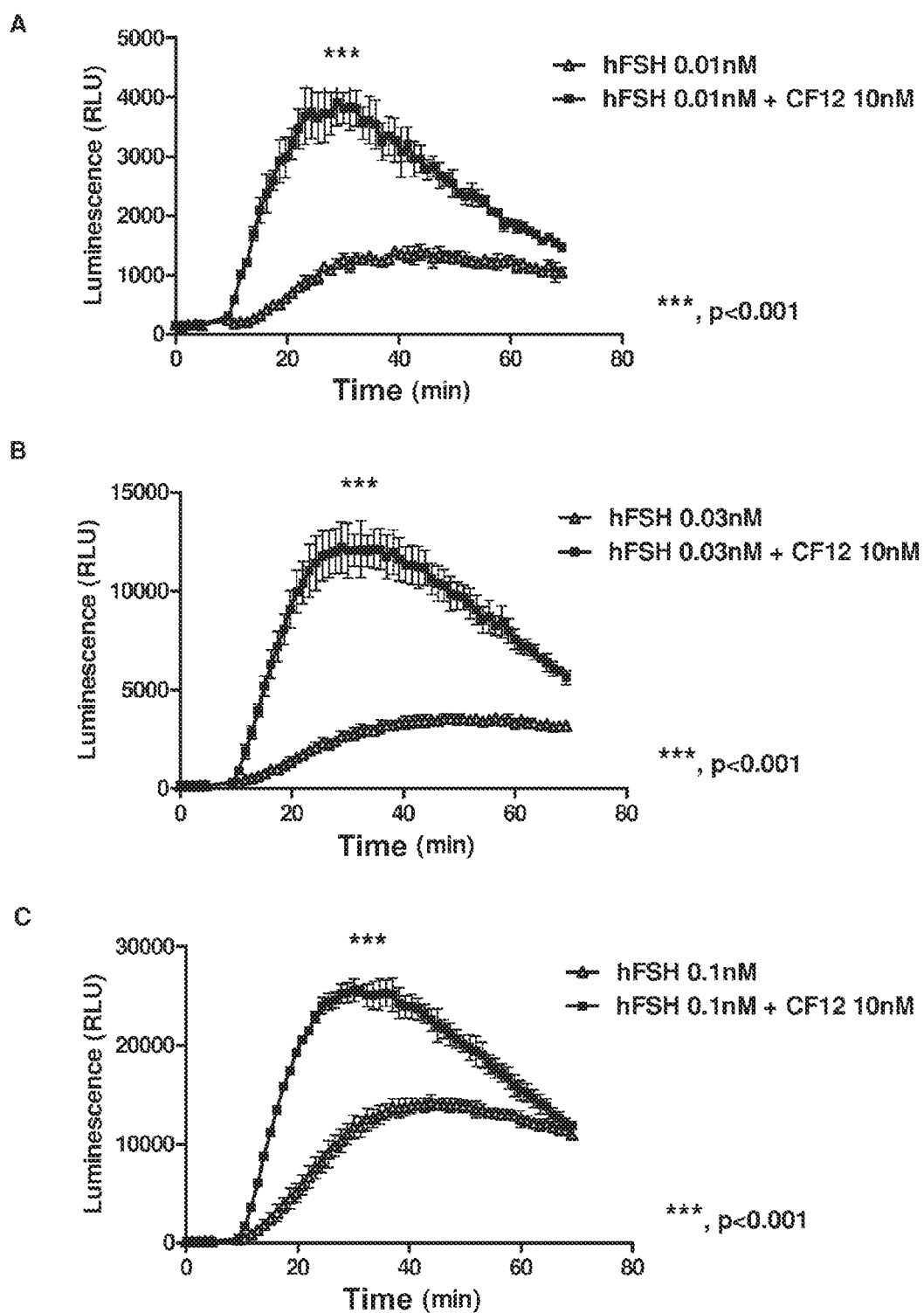
FIG. 3 represents the in vitro potentiating effect of the CF12 monoclonal antibody on the bioactivity of human FSH (hFSH) on an HEK 293 cell line stably transfected with the human FSH receptor and the Glosensor® vector.

FIG. 3 illustrates the notable potentiating effect of CF12 on the bioactivity of human FSH (Gonal-F, Serono Laboratory). This notable effect is perfectly quantifiable at the low concentrations of 0.01 nM and 0.03 nM of hFSH for which the cell system is not at saturation (curves A and B). An increase in the luminescence signal of 280% and 341% respectively, which are highly significant ($p<0.001$), is observed. For the higher concentrations (0.1-0.3 and 1 nM), the increase in the cell response is 181%, 147% and 120% respectively, probably due to a gradual saturation of the luminescent signal up to 46 000 RLU (curves C, D and E). For curves C, D and E, the increase remains very significant ($p<0.001$). The EC50 value measured by GraphPad Prism is $4.25\times10^{-10}$ M for hFSH and $9.38\times10^{-11}$ M for the hFSH/CF12 complex, reflecting an increase in the bioactivity of the hormone of 0.7 Log EC50 units (from $10^{-9.37}$ to $10^{-10.03}$ respectively) when it is complexed with the potentiating antibody CF12 (curve F).

Figure 4:
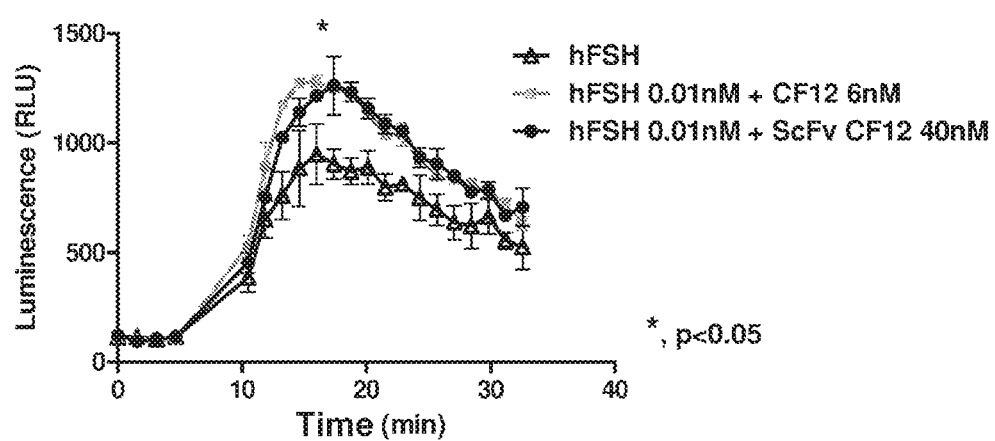
FIG. 4 represents the in vitro potentiating effect of the CF12 monoclonal antibody and of the CF12 scFv on the bioactivity of human FSH (hFSH) on an HEK 293 cell line stably transfected with the human FSH receptor and the Glosensor® vector.

The potentiating effect of the CF12 scFv (40 nM) was also measured on the activity of human FSH (Gonal-F, Serono Laboratory) prepared at the concentration of 0.01 nM (FIG. 4). The effect of the whole CF12 antibody (6 nM) was measured in parallel for comparison. The curves obtained with the hFSH/CF12 scFv or hFSH/CF12 antibody complex superimpose with one another perfectly, indicating an identical effect of the monovalent antibody fragment.

Figure 5:
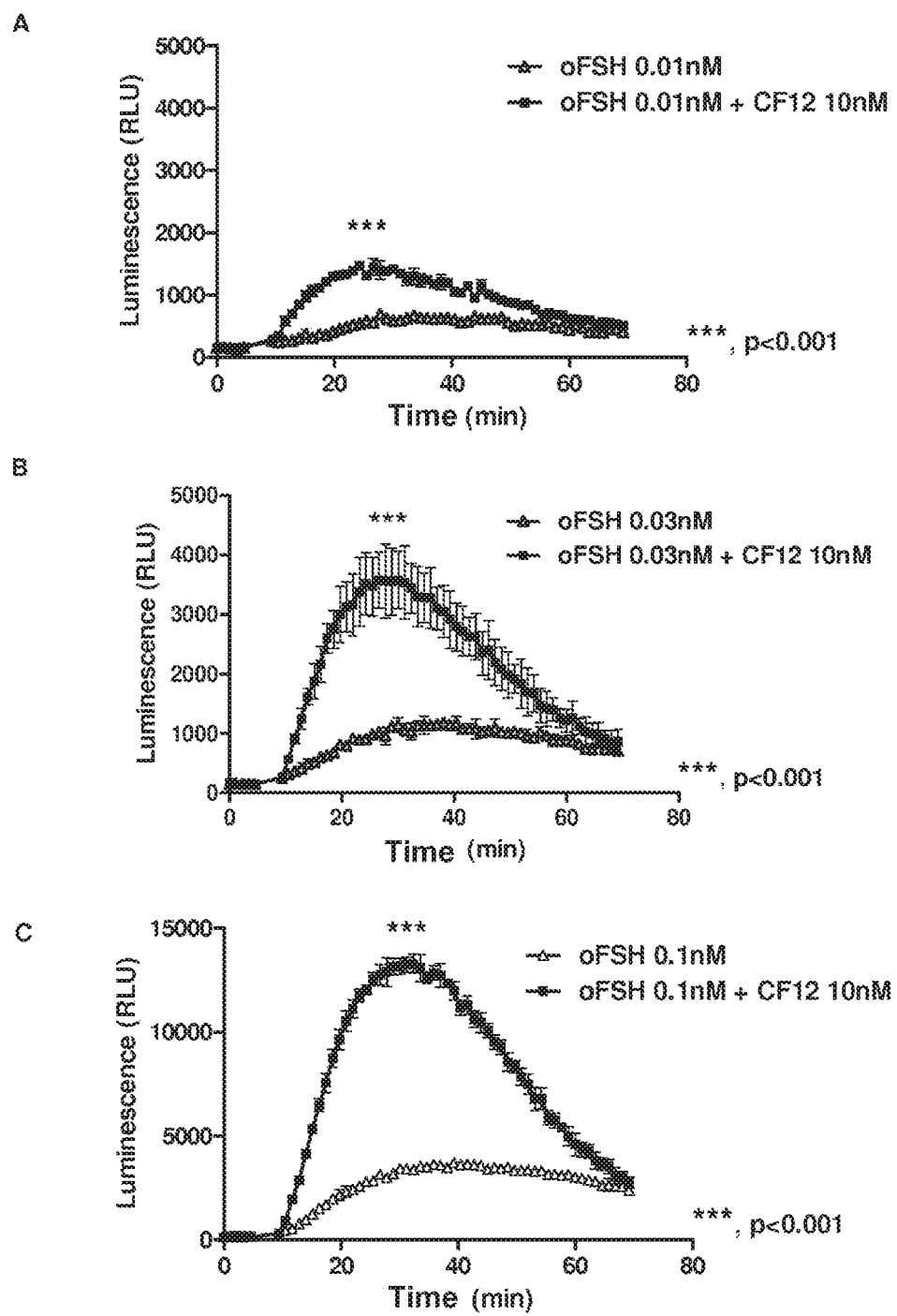
FIG. 5 represents the in vitro potentiating effect of the CF12 monoclonal antibody on the bioactivity of ovine FSH (oFSH) on an HEK 293 cell line stably transfected with the human FSH receptor and the Glosensor® vector.

The potentiating effect exerted by CF12 is also very significant on ovine FSH as illustrated in FIG. 5, wherein an increase in the cell response of 240%, 300% and 350% is observed during a stimulation with the CF12/oFSH complex for the hormone concentrations 0.01 nM-0.03 nM and 0.1 nM (curves A, B, C). CF12 was prepared at 10 nM. In the same way as for hFSH, for the higher concentrations 0.3 nM and 1 nM (curves D and E), the increase in the cell response is 200% and 130% respectively due to a gradual saturation of the luminescent signal up to 40 000 RLU. The EC50 value measured by GraphPad Prism is $2.29\times10^{-9}$ M for oFSH and $1.98\times10^{-10}$ M for the oFSH/CF12 complex, reflecting an increase in the bioactivity of the hormone of 1.06 Log EC50 (from 8.64 to 9.7 respectively) when it is complexed with the potentiating antibody CF12 (curve F). The potentiating effects observed on the cell response are in all cases highly significant ($p<0.001$).

Figure 6:
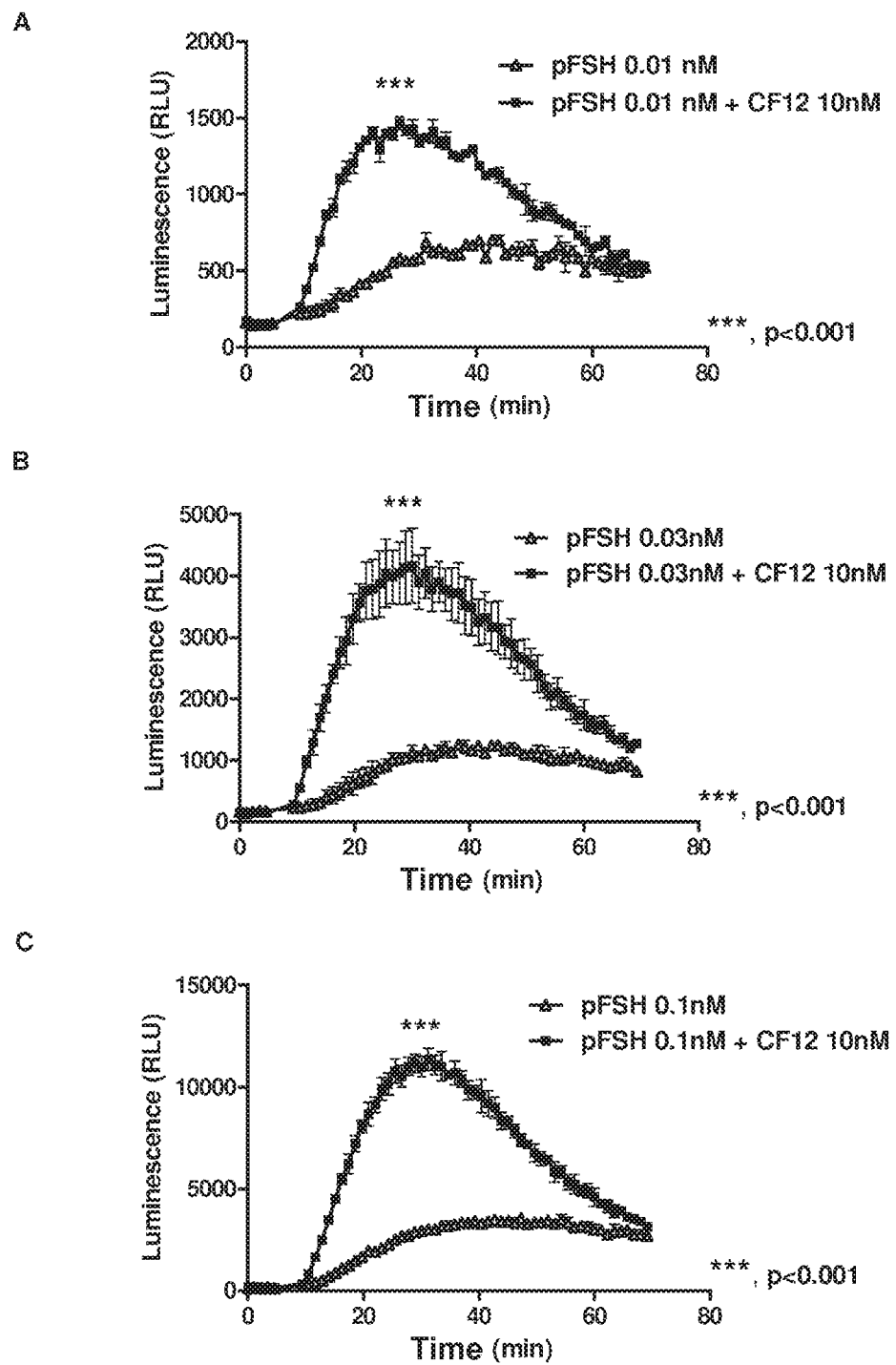
FIG. 6 represents the in vitro potentiating effect of the CF12 monoclonal antibody on the bioactivity of porcine FSH (pFSH) on an HEK 293 cell line stably transfected with the human FSH receptor and the Glosensor® vector.

The curves of FIG. 6 illustrate the potentiating effect of CF12 (10 nM) on porcine FSH prepared at the concentrations of 0.01-0.03-0.1-0.3 and 1 nM. This effect is perfectly quantifiable at the lowest pFSH concentrations 0.01 nM-0.03 nM and 0.1 nM for which the cell system is not at saturation (curves A, B, C). A very significant and considerable increase in the luminescence signal of 220%, 350% and 330% respectively is thus observed. For the higher concentrations (0.3 and 1 nM), the increase in the cell response is less, respectively 175% and 114%, due to a gradual saturation of the luminescent signal up to the limit of 40 000 RLU (curves D and E). The EC50 value measured by GraphPad Prism is $1.92\times10^{-9}$ M for pFSH and $3.69\times10^{-10}$ M for the pFSH/CF12 complex, reflecting an increase in the bioactivity of the hormone of 0.717 Log EC50 (from $10^{-8.715}$ to $10^{-9.432}$ respectively) when it is complexed with the potentiating antibody CF12 (curve F).

4/On Primary Cultures of Human Granulosa Cells

The human granulosa cells were recovered and cultured as described in Reverchon et al (Reverchon et al., Human Reprod., 27(6): 1790-1800, 2012) [11].

These cells were recovered from follicular fluids harvested after oocyte puncture in women treated for in vitro fertilization (IVF) in the context of assisted reproductive technology (ART). These cells were isolated by centrifugation on a 40% Percoll gradient, resuspended in a complete McCoy's 5A medium (Lonza, Belgium, reference BE12-688F) and then seeded into 24-well plates (Becton Dickinson, N.J., USA, reference 353047), in a proportion of 30,000 cells per well in a final volume of 500 µl, and cultured for 48 hours. They were then stimulated either with human FSH alone or with the human FSH/MAb complex for 48 hours.

The human FSHs used were mainly Gonal-F, a recombinant hormone sold by the pharmaceutical laboratory Serono (Serono, Europe, Limited) and Fostimon, an FSH extracted from urine from menopausal women, sold by the pharmaceutical laboratory Genevrier (France). After stimulation, the supernatants were recovered and centrifuged. The cAMP produced was assayed in each culture supernatant using an ELISA kit (Biomedical Technologies Inc., MA, USA, BT-730).

The cells from 23 patients were prepared separately and cultured separately according to the method described above. Each cell culture from a patient was divided into two batches: one was stimulated with a range of FSH of from $10^{-11}$ M to $10^{-8}$ M, the other was stimulated with the CF12 monoclonal antibody/hFSH complex at the various concentrations of the range. The antibody was prepared at the final concentration of 0.1 nM or at 4 nM. For each patient, the dose-response curves obtained under the two conditions were compared in order to evaluate the potentiating effect of the antibody on the bioactivity of the human hormone used.

The cell cultures from the 23 patients showed very different responses to the stimulation with hFSH and/or with the hFSH/antibody complex. Only the cells from 12 patients out of the 23 in total responded to a stimulation with FSH alone, regardless of the hFSH used, and to a stimulation with the FSH/antibody complex (FIG. 7, curves A, B, C). These results are shown in FIG. 7. Curve A represents the cell response of a patient to a stimulation with Gonal-F and with Fostimon; the EC50 values measured were $7.10^{-11}$ and $1.10^{-9}$ respectively. Curves B and C illustrate two cases representative of patients whose granulosa cells responded both to a stimulation with hFSH alone (Gonal-F for curve B and Fostimon for curve C) and to a stimulation with the CF12/hFSH complex. In the case of curve B, the EC50 value of the dose-response curve obtained with the complex is greater than that obtained with the hormone alone ($7.52\times10^{-10}$ M compared with $2.42\times10^{-9}$ M). In the case of curve C, the EC50 values are not different ($2.28\times10^{-9}$ M compared with $3.61\times10^{-9}$ M).

Figure 8:
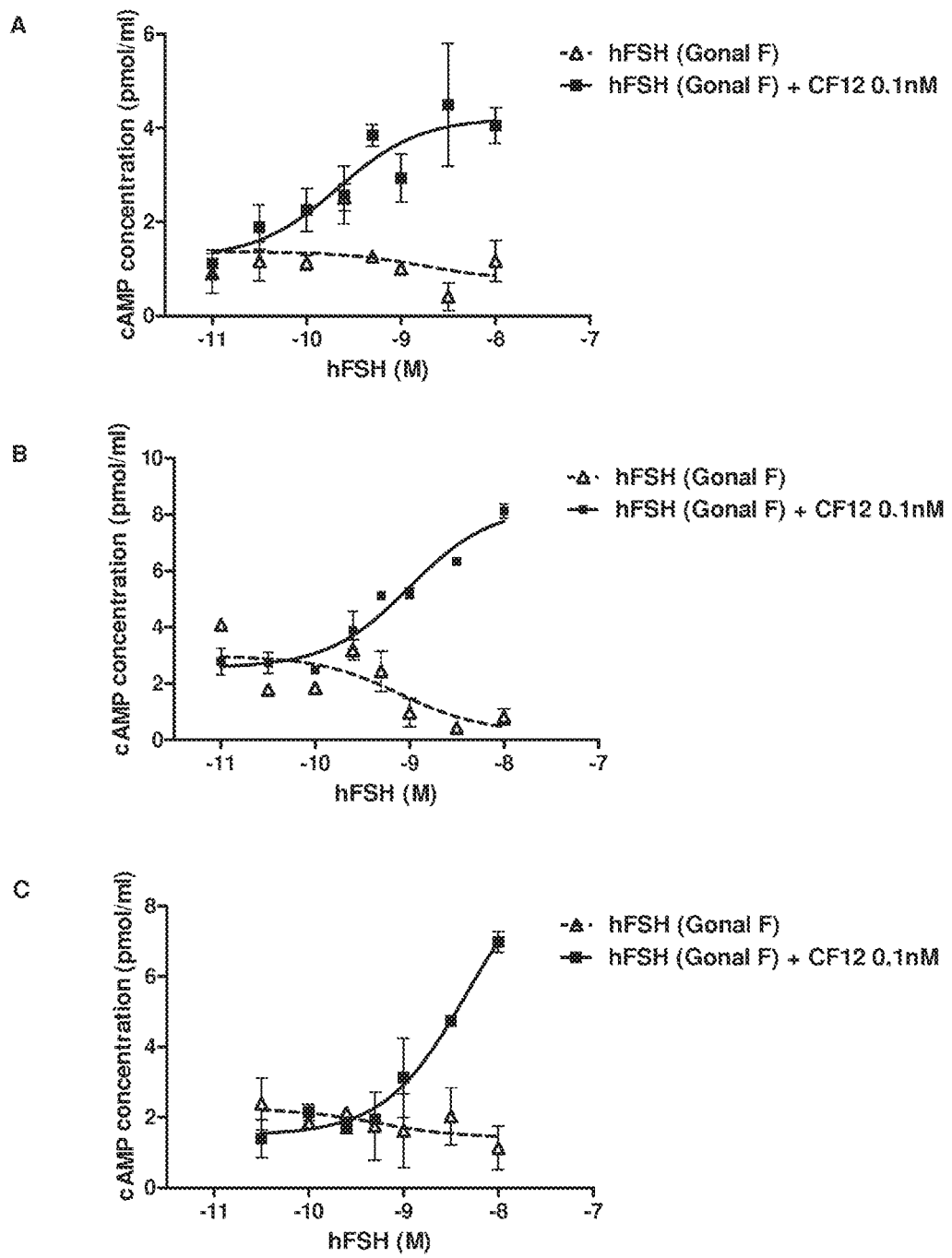
FIG. 8 represents the in vitro potentiating effect of the CF12 monoclonal antibody on the bioactivity of the human FSH (hFSH) Gonal-F® on human granulosa cells.
Figure 12:
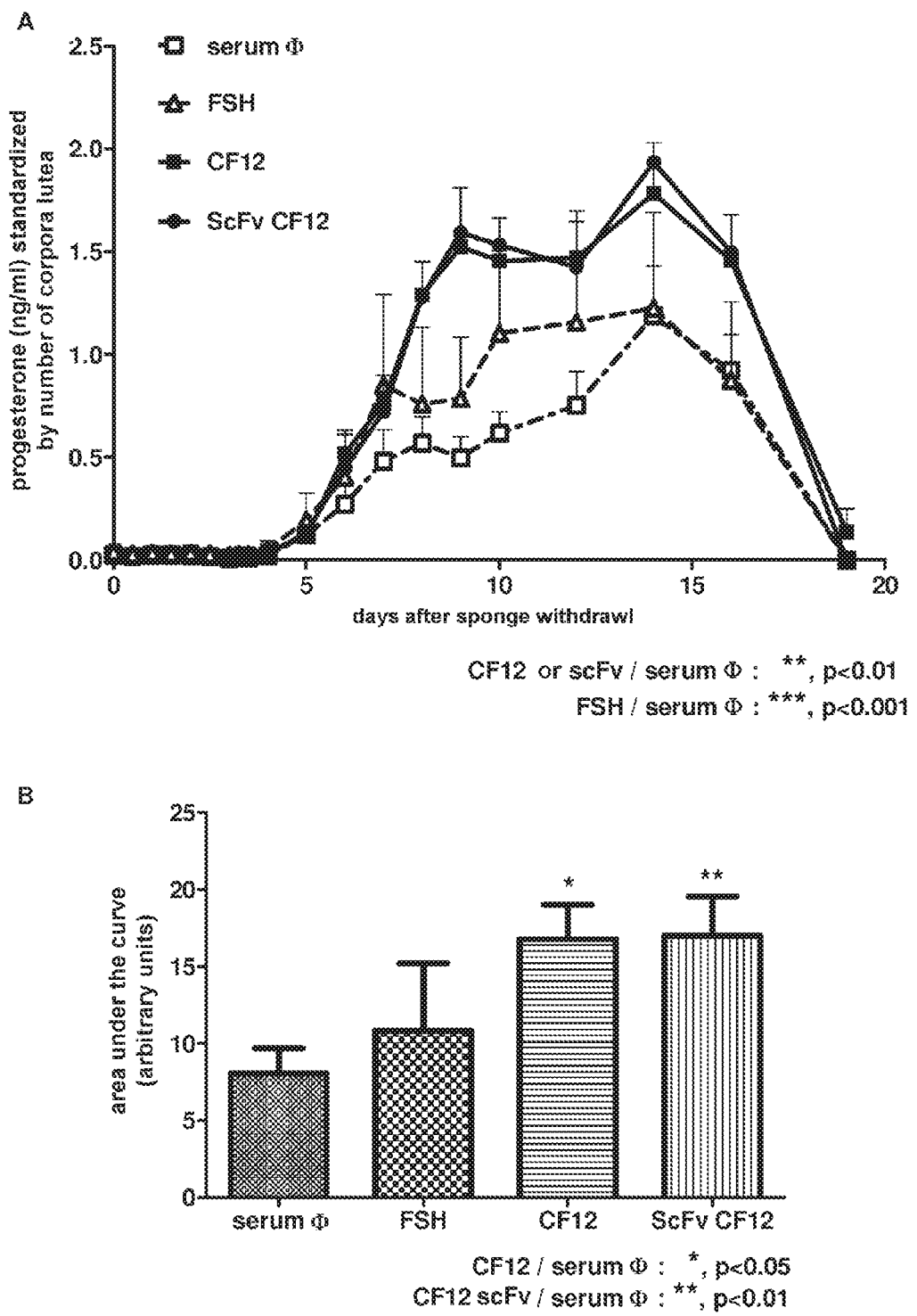
FIG. 12 represents the in vivo potentiating effect of the CF12 monoclonal antibody on the bioactivity of the endogenous gonadotropins in ewes during the period of the sexual season.

Out of the 11 remaining patients, the cells from four of them responded neither to a stimulation with FSH nor to a stimulation with the FSH/CF12 complex. Conversely, and surprisingly, the cells from the other 7 patients responded only to a stimulation with the FSH/potentiating antibody complex whereas no increase in cAMP secretion was observed after stimulation with hFSH alone in the same concentration range. These notable results are illustrated by FIG. 8, curves A to F, each curve representing the response of the granulosa cells of a different patient. In each of the cases, the CF12 antibody was used at 0.1 nM. Two patients gave the same dose-response curve illustrated by curve D. These results demonstrate very clearly that, in these patients, only the hFSH/CF12 antibody complex is capable of inducing a functional stimulation of the hFSHR receptor, unlike FSH alone which brings about no activation of the hFSHR receptor. The maximum cAMP secretion level obtained under stimulation with the hFSH/CF12 antibody complex lies between 6 a 15 pmol/ml equivalent to the maximum secretion level obtained with cell cultures having normally responded to hFSH (FIG. 12). The EC50 values measured by Graph Pad Prism for each of the dose-response curves are shown in table 13:

TABLE 13

| patient | A | B | C | D* | E | F |
|---|---|---|---|---|---|---|
| EC50 (M) | $2.15 \cdot 10^{-10}$ | $1.11 \cdot 10^{-9}$ | $4.27 \cdot 10^{-10}$ | $1.71 \cdot 10^{-10}$ | $8.91 \cdot 10^{-11}$ | ND |

*the EC50 value obtained for patient G was identical to that of patient D.

The hFSH/CF12 antibody complex thus behaves as a novel ligand, as a novel agonist capable of activating the hFSHR in patients naturally refractory to conventional stimulation with recombinant or extracted hFSH. The use of an hFSH/potentiating antibody mixture can thus provide a new alternative in hormonal treatments for inducing ovulation (mono ovulation or poly ovulation) in patients who do not respond to the conventional hormonal treatments used in human reproductive biology.

Example 3: In Vivo Measurement of the Potentiating Effect of the Ligands of the Invention on the Bioactivity of FSH and LH/CG in the Rat Model After having been characterized in vitro, the potentiating effect of the monoclonal antibody was characterized in vivo, in the female rat for its effect on the bioactivity of FSH and in the male rat for its meffect on the bioactivity of LH/CG, that they also recognize.

In order to measure the FSH bioactivity, the protocol used was that of the biological assay described by Steelman and Pohley (Steelman S L, Pohley F M. Endocrinology, 53:604-616. 1953) [12]. In order to measure the LH bioactivity, the protocol used was that of the assay described by Scobey et al. (Scobey et al., Reprod. Biol. Endocr. 3±2005

The effect of the antibodies on the FSH activity was evaluated using human FSHs. The effect of the antibodies on the LH activity was evaluated on two preparations of hCG (human chorionic gonadotropin).

The statistical analysis was carried out with the Graph Pad Prism software (GraphPad Software Inc., San Diego, Calif., USA, version 5). Since the results related to experiments carried out on batches of five animals, a non-parametric, one-way analysis of variance (Kruskal Wallis test), followed by Dunns correction, was applied or a non-parametric t-test (Mann-Whitney test). For the results relating to larger numbers (n>30) resulting from the compilation of several bioassays, a parametric test (unpaired Student's t test) followed by a Bonferroni correction was applied.

1/Potentiating Effect of the Antibodies on the Bioactivity of FSH in the Female Rat The potentiating effect of the CF12 antibody and of the scFv thereof was studied on various preparations of human FSH used in human reproduction in the context of assisted reproductive technology treatments: Gonal-F and Puregon (recombinant FSHs from the Merck Serono and Merck Schering-Plough laboratories respectively), and Fostimon and Menopur (extracted FSHs sold by the laboratories Genevrier and Merck Schering-Plough respectively).

As described in the protocol of Steelman and Pohley, 21-day-old immature female rats received, for three consecutive days, two injections, in the morning and the evening, of 100 µl of a mixture of hCG and FSH comprising a constant amount of hCG (3.5 IU) supplemented with a variable amount of FSH ranging from 0.5 to 1.5 IU for the human FSH (Gonal F, Puregon, Fostimon, Menopur). Injections were carried out subcutaneously into the nape of the neck. Each experiment comprised a minimum of four batches: one batch treated with physiological saline (serum 0), one batch treated with the antibody or the scFv alone, one batch treated with the hCG+FSH mixture, and one batch treated with the hCG/FSH mixture supplemented with 2 µg of purified scFv or antibody.

In the case of a treatment with the hormone/antibody or scFv complex, before the injection, the FSH+antibody mixture was preincubated for 20 minutes at 37° C. or at ambient temperature, without distinction, and then added to the hCG. The hCG can without distinction be mixed with the FSH during the incubation of the complex.

On the fourth day, the female rats were weighed, and their ovaries were taken, dissected and then weighed. The results are expressed in milligram of ovary/100 grams of body weight. The increase in the weight of the ovaries is proportional to the amount of bioactive FSH injected. This makes it possible to quantify and compare the bioactivity of the same amount of hormone injected alone or as a complex with an antibody.

Comparison of the bioactivity of the FSH injected alone or complexed with the antibody or with the scFv makes it possible to measure the differential of the response and to thus quantify the potentiating effect of the antibody or of the scFv thereof.

Potentiating Effect of the CF12 Antibody and of the scFv Thereof

The in vivo effect of the CF12 antibody, produced against human FSH, was evaluated on the bioactivity of various preparations of human FSH and on the bioactivity of ovine FSH.

FIG. 9A shows the notable potentiating effect exerted by the CF12 antibody on three different preparations of human FSH. The results are those of representative bioassays comprising batches of 5 females. The statistical analysis between batches was carried out using a non-parametric t-test (Mann-Whitney test). A considerable and significant potentiating effect was recorded on the activity of the hFSH Gonal-F with an increase of 210% in the mean weight of the ovaries (74 compared with 155 mg/100 g of body weight, p<0.001). Likewise, on Puregon, an increase of 190% was obtained (141 compared with 224 mg, p<0.05) and also on Fostimon with which an increase of 160% in the mean weight of the ovaries was recorded (85 compared with 161 mg, p<0.05).

These experiments were repeated between 5 and 7 times and the results were compiled (n=40 and 47 female rats for the batches hCG+hFSH Gonal-F and hCG+hFSH Gonal-F+CF12). A parametric test (unpaired Student's t test) followed by a Bonferroni correction were applied. As illustrated in table 14, it reveals a highly significant increase of 170% between the mean weight of the ovaries in the females treated conventionally with the hCG+hFSH (Gonal-F) mixture and that measured in the females treated with the hFSH Gonal-F/CF12 complex: the mean weight increasing from 79.51±2.178 mg of ovary/100 g of bodyweight to 134.8±4.985 mg of ovary/100 g of body weight in the females (***, p<0.001).

TABLE 14

| batch | Mean ± sem | numbers | statistics |
|---|---|---|---|
| Physiological saline | 29.68 ± 5.88 | 10 | NS |
| CF12 2 µg | 34.3 ± 7.9 | 12 | |
| hCG + hFSH | 79.51 ± 2.178 | 40 | *** |
| hCG + hFSH + CA5 | 134.8 ± 4.985 | 47 | p < 0.0001 |

The same approach was carried out to evaluate and quantify the potentiting effect of the CF12 antibody on FSH of ovine origin.

FIG. 9B illustrates a representative example of bioassay obtained (batches of 5 females) by treating the female rats with 0.5 µg of ovine FSH+hCG or with hCG+0.5 µg of ovine FSH pre-complexed with CF12. An increase of 170% in the mean weight of the ovaries was obtained in the females treated with the oFSH/CF12 complex+hCG compared with those having received a treatment without CF12: the mean weight of the ovaries going from 107 mg to 183 mg/100 g of body weight (**, p<0.01).

The repetition of this study on larger numbers (n=10) very significantly confirmed the potentiating effect of CF12 on the bioactivity of oFSH (table 15), the mean weight increasing from 115.5±7.45 mg in the case of the conventional treatment to 166.4±9.54 mg in those treated with the oFSH/CF12 complex+hCG (***, p<0.001).

TABLE 15

| batch | Mean ± sem | numbers | statistics |
|---|---|---|---|
| hCG + oFSH 0.5 µg | 115.5 ± 7.45 | 10 | *** |
| hCG + oFSH + CF12 | 166.4 ± 9.54 | 10 | p < 0.001 |

The CF12 scFv developed from the sequence of the variable regions $V_H$ and $V_L$ of the antibody was evaluated in the same way on the bioactivity of human FSH. Beforehand, several doses of scFv were evaluated from 0.06 µg per injection (corresponding to an amount equimolar with the whole antibody of $2.5×10^{-9}$ mol) to 2 µg per injection corresponding to the same injected amount of the whole antibody. The comparison of various doses of scFv in the bioassay demonstrated that an optimal potentiating effect is obtained by injecting 2 µg of scFv per injection, that is to say $8×10^{-8}$ mol.

Figure 10:
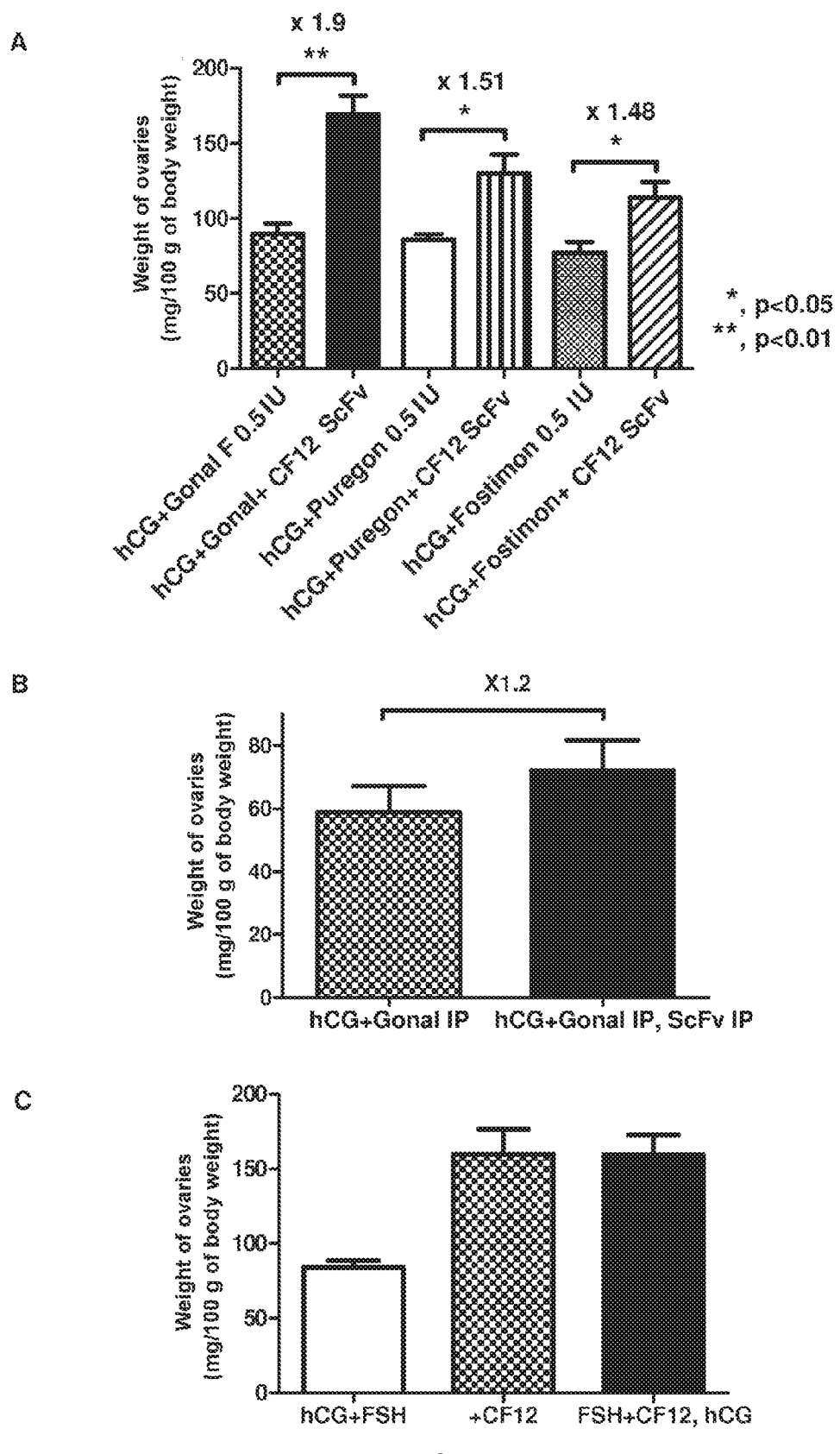
FIG. 10 represents the in vivo potentiating effect of the CF12 scFv on the bioactivity of the human FSHs (hFSH) Gonal-F® (A and B), Puregon® and Fostimon® (A) and of the CF12 monoclonal antibody on the bioactivity of the human FSH (hFSH) Gonal-F according to various administration methods (C) in the female rat.

The results obtained on the various preparations of human FSHs are shown in FIG. 10A. They show that the effects recorded with the scFv are very close to those measured with the whole antibody on the three human FSH preparations. The mean weight of the ovaries was systematically higher in the female rats treated with the hFSH/scFv/CF12 complex+hCG compared with those treated conventionally with hFSH+hCG. Thus, an increase of 190% was recorded on the hFSH Gonal-F (with a mean weight of 170 mg in the batch+CF12 scFv compared with 89 mg in the batch without CF12 scFv, p<0.01), an increase of 151% on the hFSH Puregon (mean weight of 130 mg in the batch+CF12 scFv compared with 86 mg in the batch without scFv, p<0.05) and an increase of 148% on the hFSH Fostimon (mean weight of 114 mg in the batch+CF12 scFv compared with 77 mg in the batch without scFv, P<0.05). The analysis was carried out using a non-parametric t-test (Mann-Whitney test). It should be noted that the size of the increase in the ovarian response is equivalent to that obtained with the whole CF12 antibody (same multiplying factor). This significant and major result indicates that one and the same potentiating effect of the circulating gonadotropins can be obtained in vivo, whether by means of an scFv or of a whole antibody, resulting in the tangible amplification of a physiological response in an organ.

Various methods of injection of the hormone/antibody or scFv mixtures were evaluated and compared with the conventional protocol (subcutaneous injection) also in the case of CF12. Thus, a bioassay for the purpose of comparing an intraperitoneal injection of the hormonal mixture with an intraperitoneal injection of the hormonal mixture followed by a second, delayed, injection of the CF12 scFv 15 minutes later was carried out. The results are presented in FIG. 10B, and indicate an increase in the weight of the ovaries of 122% in the females injected intraperitoneally in two steps: 1) with the hCG+hFSH mixture then 2) with scFv by delayed injection 15 minutes later: 58.8 mg of ovary per 100 g of body weight in the hCG+hFSH Gonal-F batch compared with 72 mg of ovary per 100 g of body weight in the batch hCG+hFSH Gonal-F followed by scFv. The difference is not significant between the two batches due to the small numbers, but the results indicate a trend toward potentiation of the FSH by injecting the hormone and the scFv in two steps and at two different injection points. It is thus possible to envision, for subsequent applications, injecting the hormone to be potentiated and then the antibody or the scFv independently in terms of time and different injection points.

Another injection mode was evaluated in the animals treated with the hormone/antibody complex: one having a single subcutaneous injection of hCG+FSH+CF12 and the other having a first subcutaneous injection of FSH+CF12 and then 15 minutes later an injection of hCG, also subcutaneously. The results shown in FIG. 19C show that the potentiating effect observed in the two cases is not different: 160 mg compared with 159 mg of ovaries/100 g of body weight in the females treated with the CF12 antibody for a mean weight of 83 mg of ovaries for the batch treated without antibody.

Potentiating Effect of the Antibodies on the Bioactivity of LH/CG in the Rat

Because of the very high cost of ovine LH, these biological assays were carried out with hCG, which is readily available, in a very pure and inexpensive form. The effect of the antibodies was studied on two preparations of extracted hCG (human chorionic gonadotropin), one used in human reproduction in the context of assisted reproductive technology treatments: ENDO 5000 (Schering-Plough laboratory) and the other used in veterinary medicine: Chorulon (MSD laboratory).

According to the protocol of Scobey et al. [13], the bioactivity of LH or of hCG was quantified with respect to the increase in weight of the seminal vesicles, the development of which is androgen-dependent. The weight varies proportionally to the activity of the hCG and thus makes it possible to quantify and compare the biological activity of the hormone injected alone or complexed with the antibody studied. The protocol was carried out with 25-day-old young rats which were injected subcutaneously, once a day for four days, with 100 µl of 1.5 IU of hCG or of a mixture of 1.5 IU hCG+2 µl of antibody preincubated for 20 min at 37° C. On the fifth day, the rats were weighed and then sacrificed. Their seminal vesicles (SVs) were removed, dissected and weighed. The weight of the seminal vesicles is expressed in mg/100 g of body weight in order to be able to compare and combine the results obtained with various batches. In each experiment, each of the conditions was tested on a batch of five rats. The same experiment was repeated several times.

FIGS. 11A, B and C show the results obtained with the rats treated with the CF12 antibody in a complex with the hCG Chorulon and the hCG Endo 5000. FIG. 11A shows the representative result of a bioassay carried out on 6 batches of 5 rats. A very significant potentiating effect (p<0.0001, Krustal and Wallis test) was obtained with the hCG Chorulon/CF12 complex with an increase of 220% in the weight of the seminal vesicles compared with the batch treated with hCG alone. A significant effect was also obtained on the batch treated with the hCG Endo 5000/CA5 complex with an increase in the weight of 189% (p<0.0001). It is observed that the batch treated with the CF12 antibody alone shows no change in the weight of the seminal vesicles compared with the control animals treated with physiological saline. CF12 not complexed to the hormone thus has no specific effect on the target organ.

Figure 11:
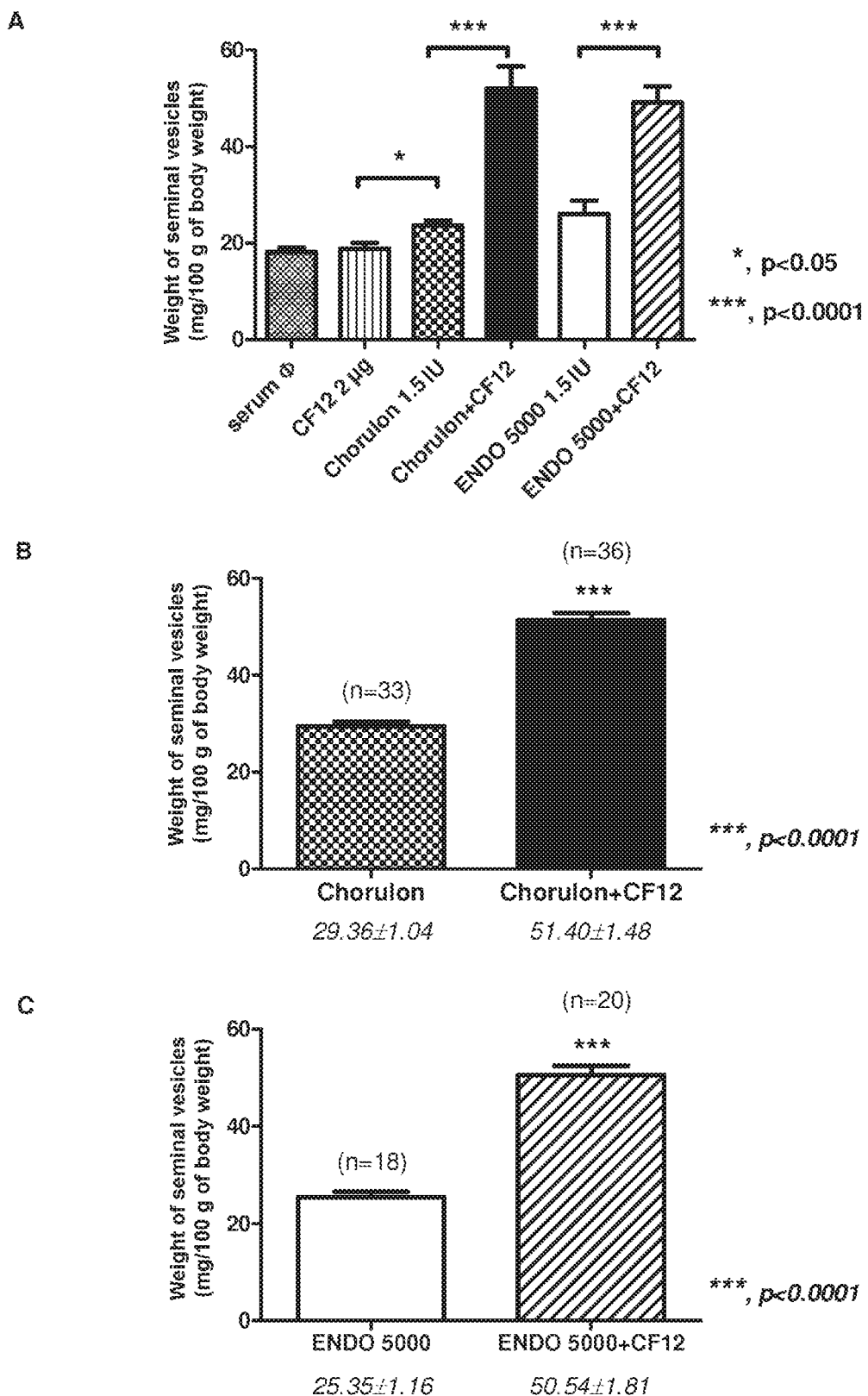
FIG. 11 represents the in vivo potentiating effect of the CF12 monoclonal antibody on the bioactivity of the human chorionic gonadotropins (hCG) Chorulon® and Endo 5000® in the male rat.

The compilation of the results resulting from the various bioassays carried out with CF12 is represented on the histograms B and C of FIG. 11. A highly significant potentiating effect (p<0.0001, unpaired t-Test) of the hormone/CF12 complex was measured with hCG Chorulon and hCG Endo 5000:

on numbers of 33 and 36 animals respectively, the mean weight of the SVs was 29.36 mg/100 g in the rats treated with hCG Chorulon compared with 51.40 mg/100 g in the rats treated with the complex (increase of 175%) (FIG. 11B)

on numbers of 18 and 20 animals respectively, the mean weight of the SVs was 25.35 mg/100 g in the rats treated with hCG Endo 5000 and 50.54 mg/100 g in the rats treated with the complex (increase of 208%) (FIG. 11C).

Example 4: In Vivo Measurement of the Potentiating Effect of the Ligands of the Invention on the Bioactivity of Endogenous Gonadotropins in Ewes After having demonstrated and characterized the potentiating effect in vivo, of the CF12 monoclonal antibody, in a rodent (small animal), the objective was to study the effect of each antibody on the activity of FSH in productive livestock, which are larger: ewes.

For this, a study was carried out on pubescent, Ile de France, ewes, all of the same age, with the aim of evaluating the potentiating effect of the antibodies on the treated ewes' own hormones (endogenous hormones). The study of the specificity showed strong binding of the CF12 antibody for ovine FSH and more variable binding for ovine LH. For this purpose, a treatment comprising only injection of an antibody alone was developed in order to evaluate the efficacy thereof.

In the protocols set up in ewes, the antibody was thus injected alone and not preincubated with the exogenous FSH, as was done in the studies in the female rat. Furthermore, each antibody was injected into ewes free of any prior stimulation of the ovary: the animals received no hormonal treatment for stimulating ovulation with a gonadotropin prior to the injection of the antibody.

The potentiating effect of the anti-FSH CF12 antibody was evaluated during protocols carried out right in the middle of the sexual season (January) or at the end of the sexual season (end of March). The protocols were all carried out on ewes in which the ovulatory cycle was presynchronized by implanting a vaginal sponge impregnated with a progestogen (45 mg of fluorogestone acetate (FGA)—MSD) for 14 days. The potentiating effect was analyzed by comparing the ovulatory response (number of ovulations) and the establishing of one or more functional corpora *lutea* of good quality (size of the progesterone secretion) in control ewes (physiological saline batch), ewes stimulated with a porcine FSH treatment (FSH batch) and ewes stimulated with an antibody alone (antibody batch).

In each protocol, a plasma LH assay was carried out by the ELISA method in order to detect and date the preovulatory peak of LH. To evaluate the ovulatory response, an endoscopic observation of the ovaries was carried out by laparoscopy, under anesthesia, eight days after withdrawal of the vaginal sponge, in order to count the number of corpora lutea and to observe their appearance.

To evaluate the functionality and the quality of the corpus luteum or corpora lutea, a quantitative progesterone ELISA assay was carried out using daily blood samples from the $1^{st}$ to the $21^{st}$ day after withdrawal of the sponge.

All the statistical analyses were performed with the GraphPad Prism Version 5.0 software (GraphPad, San Diego, Calif., USA).

CF12 Antibody and the scFv Thereof

The potentiating effect of CF12 (IgM) and of the scFv thereof was studied and compared using the measurement parameters of ovulation and of functional quality of the corpus luteum established. The doses injected were 2 times 1 mg.

The protocol carried out in the sexual season comprised four batches:

the CF12 antibody batch (n=7) received an intramuscular injection of 1 mg of antibody 24 h before withdrawal of the sponge and a second injection of 1 mg at the time the sponge was withdrawn;

the CF12 scFv batch (n=5) received an intramuscular injection of 1 mg of scFv 24 h before withdrawal of the sponge and a second injection of 1 mg at the time the sponge was withdrawn;

the "control" batch (n=9) received an injection of physiological saline, intramuscularly, 24 h before the withdrawal of the sponge and at the time of the withdrawal;

the "FSH" batch (n=11) received an intramuscular injection of 100 µg of porcine FSH (pFSH) 24 h before the withdrawal of the sponge and of 90 µg 12 h before the withdrawal of the sponge.

Endoscopies of the ovaries were carried out 8 days after withdrawal of the sponge.

Daily blood samples from the 1st to the $21^{st}$ day after withdrawal of the sponge were taken in order to assay the plasma progesterone by ELISA assay.

The analysis of the ovulatory response gave the results presented in table 16 below. The statistical analysis was carried out by means of a Fisher's exact test.

TABLE 16

|  | Serum φ batch | FSH batch | CF12 alone batch | CF12 scFv alone batch |
|---|---|---|---|---|
| Number of ewes per batch | 9 | 11 | 7 | 5 |
| Number of ewes having ovulated per batch | 4/9 (44%) | 4/11 (36%) | 7/7 (100%)*** | 5/5 (100%)*** |
| Number of corpora lutea per total ewes | 0.67 ± 0.3 | 0.9 ± 0.5 | 1.7 ± 0.4 | 2.2 ± 0.4* |
| Number of corpora lutea per ewe having ovulated | 1.5 ± 0.3 | 3 ± 1.4 | 1.7 ± 0.4 | 2.2 ± 0.4 |
| Time of the LH peak (hours after withdrawal) | 64 ± 13 | 56 ± 5 | 52 ± 3.2 | 51.6 ± 4 |

*p < 0.05;
***p < 0.0001

Compared with the control and FSH batches, the results obtained in the CF12 and CF12 scFv batches show a very significant effect of the antibody or of the scFv thereof injected alone on the ovulatory response. Indeed, 100% of the females (7/7 for CF12 and 5/5 for the CF12 scFv) having received two injections of 1 mg of antibody or scFv ovulated, compared with 44% and 36% respectively for the serum CD batch and the FSH batch (p<0.0001, Fisher's exact test). The number of corpora lutea obtained per female on the total numbers of the batch is significantly higher in the CF12 scFv batch (p<0.05, Kruskall Wallis test) compared with the FSH and serum φ batches: 2.2 corpora lutea compared with 0.9 (FSH) and 0.67 (serum φ) respectively. There is no significant difference between the CF12 scFv and CF12 batches.

The mean moment of appearance of the LH peak is not significantly different between the three batches. Despite everything, a tendency toward less variability in the arrival of the LH peak (and thus in the moment of ovulation) is observed in the CF12 and CF12 scFv batches compared with the FSH batch and especially serum CD batch. In this hypothesis, this would indicate a better ovulation synchronization in the ewes having received the antibody or the scFv thereof.

The progesterone secretion profile during the luteal phase following the ovulation, in the various batches, is shown in FIG. 12A. For each individual, the progesterone concentration values (ng/ml) were standardized with respect to the number of corpora lutea. Each curve of the figure represents the mean of the progesterone values measured at each sampling point in the females of each batch. The secretion curves obtained with the CF12 and CF12 scFv batches are very clearly above the FSH and serum φ batches. The results obtained indicate mean progesterone values of 1.46-1.4-1.1 and 0.6 ng/ml respectively for the CF12 scFv, CF12, FSH and serum φ batches at D10 after withdrawal of the sponge and of 1.93-1.78-1.22 and 1 ng/ml at D15.

The comparison of the four curves was carried out by means of a paired non-parametric t test (Wilcoxon test). The curves of the CF12 and CF12 scFv batches are significantly different than the curve of the serum φ batch (p<0.01). Likewise, the curve of the FSH batch is significantly different than that of the control batch (p<0.001). The difference between the curves of the ewes treated with CF12 and CF12 scFv and the curve of the ewes treated with FSH is not significant and thus represents a trend.

An analysis of the area under the curve (AUC) was carried out with the GraphPad Prism software version 5.0 in order to quantify the differences between progesterone secretion curves. The results are shown in FIG. 12B and indicate that the AUC of the CF12 scFv curve (16.98 units) is significantly higher by a factor of 1.55 than the AUC of the serum φ curve (8 units) (p<0.01, non-parametric Mann-Whitney t-test). Likewise, the AUCs of the CF12 (16.78 units) and serum φ (8 units) curves are significantly different (p<0.05, Mann-Whitney non-parametric t-test). On the other hand, there is no significant difference between AUC of the FSH curve (10.82 units) and AUC of the serum φ curve, indicating that the treatment with CF12 or with the CF12 scFv is more effective than the treatment with FSH, in the context of this experiment.

In conclusion, all of the results indicate that the monovalent fragment of CF12 has the same potentiating effects as the bivalent CF12 antibody. No significant difference was ever observed between the responses of the two batches of ewes involved. The treatment with either of the two molecules in the form of two intramuscular injections of 1 mg each gave, very significantly, better results than a conventional treatment with FSH:
  in terms of effectiveness on ovulation induction (100% of the ewes ovulated and 1.3 and 0.8 additional corpora lutea are obtained per ewe over the total numbers);
  in terms of quality of the corpora lutea established with higher progesterone secretion throughout the luteal phase.

All of the results indicate that the CF12 potentiating antibody, injected in vivo in ewes, is capable of complexing the animal's endogenous gonadotropic hormones and of potentiating the biological activity of the animal's own hormones.

The potentiating effect of the CF12 antibody in ewes is capable of inducing a stronger stimulation of the ovary than the conventional FSH hormonal treatment: ovulation induction is 100% in the sexual season and in all cases a considerable increase in circulating progesterone concentration is maintained throughout the luteal phase. This additional effect is major for reducing progestogen-dependent embryonic development failure rates and the risks of abortion.

It was shown that the monovalent scFv fragment of CF12 induces the same potentiating effects as the whole antibody, both on the induction of ovulation and on the quality of the corpus luteum and the increase in progesterone secretion in ewes. Furthermore, it was noted that the injection of the CF12 scFv in our protocol did not induce anti-CF12 scFv antibody secretion in the ewes treated. The perspective of a use of a monovalent fragment thus reduces the risks of humoral immune response that may be induced in certain ewes.

Example 5: In Vivo Measurement of the Potentiating Effect of the CF12 Ligand of the Invention on the Bioactivity of FSH in Female Monkeys After having demonstrated and characterized the potentiating effect of the CF12 monoclonal antibody in vivo in rats, female rats and ewes, its potentiating effect was studied in a species close to humans: the Cynomolgus monkey (*Macaca fascicularis*). For this, a study was carried out on pubescent female monkeys at least 36 months old, with the aim of evaluating the potentiating effect of the antibody on human FSH (hFSH).

In the protocols established, the antibody was injected either as a complex with the hFSH (the antibody having been preincubated with exogenous FSH), or injected alone, 20 minutes after an injection of hFSH.

On the first day of menstruation, the female monkeys received an injection of 1.5 mg of sustained-release GnRH preparation (Decapeptyl® L.P. 3 mg—IPSEN Pharma) intramuscularly. Fifteen days after the injection of GnRH, the female monkeys were treated according to various protocols. A single female monkey was treated per protocol.

Thirty-six hours after the final injection of hFSH, 1000 IU of hCG (chorionic gonadotropin Endo 5000—MSD) were injected into the animals. The oocytes were removed by puncture by laparotomy 36 hours after the injection of hCG, and observed under a microscope in order to evaluate their degree of maturity.

The potentiating effect was analyzed by comparing the follicular growth induced (surface area of the follicles and size of estradiol secretion) and the establishment of corpora lutea of good quality (size of progesterone secretion). For this, transabdominal ovarian ultrasounds were performed every 48 hours in order to count the follicles and to measure their surface area (expressed in mm$^2$). Blood samples taken every 48 hours from the first day of treatment up to 30 days after the follicular punctures made it possible to perform quantitative estradiol (expressed in pg/ml) and progesterone (expressed in ng/ml) ELISA assays.

All the statistical analyses were performed with the GraphPad Prism Version 5.0 software (Graph Pad, San Diego, Calif., USA).

1/Effect of the CF12 Ligand Administered Alone after Injection of 25 IU of hFSH

The potentiating effect of CF12 was first evaluated on hFSH. For this, three protocols, denoted 1 to 3, were carried out:

1—animal treated with a single injection of 25 IU of hFSH: an injection of 25 IU of human FSH (Gonal-F® pre-filled pen—Merck Serono) subcutaneously, on the first day of treatment ("hFSH 25 IU X1");

2—animal treated with CF12+hFSH: an injection of CF12 antibody (400 µg) 20 minutes after an injection of 25 IU of human FSH (Gonal-F® pre-filled pen—Merck Serono) for 20 minutes, was carried out subcutaneously, on the first and fifth day of treatment ("hFSH 25 IU+CF12 X2");

3—animal treated with 25 IU of hFSH for 8 days: a daily injection of 25 IU of human FSH (Gonal-F® pre-filled pen—Merck Serono) subcutaneously, for 8 days ("hFSH 25 IU X8").

Figure 13:
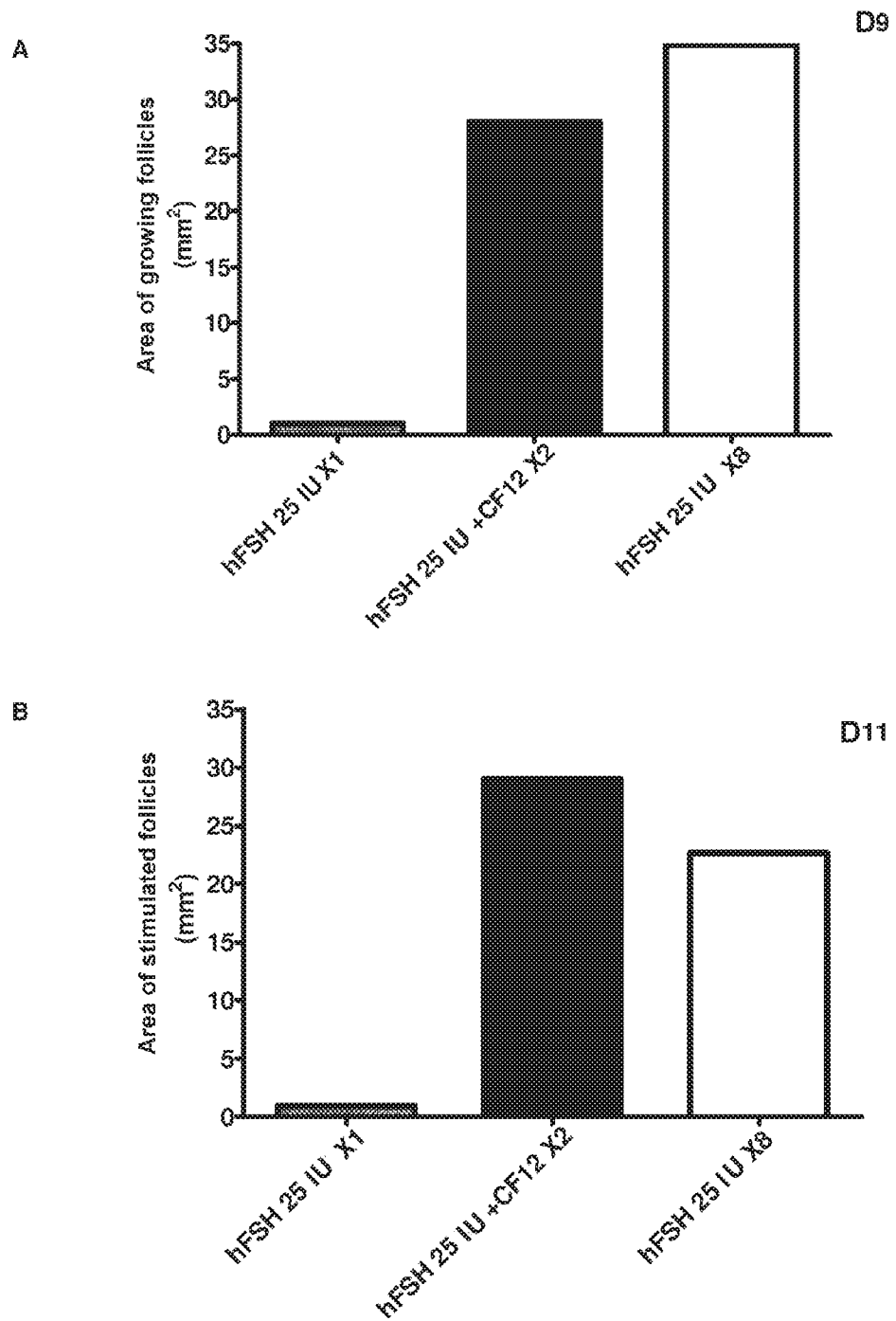
FIG. 13 represents the in vivo potentiating effect of the CF12 monoclonal antibody injected alone after 25 IU of hFSH, on follicular stimulation in female monkeys.

The effect of the three treatments was monitored by measuring the induced follicular growth (surface area of the follicles) by echography. The results obtained nine days (D9) after the beginning of the treatment are shown in FIG. 13A. They show that, on the $9^{th}$ day after the beginning of the FSH treatment, the female monkey treated with a single injection of 25 IU of hFSH exhibited no stimulated follicle (area under the curve zero). Conversely, the female monkey treated twice with the CF12 400 µg+hFSH 25 IU mixture, on the $1^{st}$ and $5^1$h day of treatment, exhibited a total surface area of stimulated follicles of 28 mm². In the female monkey having received 8 injections of hFSH, the total area of the stimulated follicles was 35 mm².

The results obtained eleven days (D11) after the beginning of the treatment are shown in FIG. 13B. They show that the female monkey treated two times with CF12+hFSH then exhibited a total area of follicles of 29 mm² with 6 stimulated follicles. In comparison, the area of the follicles measured in the female monkey having received 8 injections of hFSH was 22.6 mm² with 11 stimulated follicles. Two injections of CF12 400 µg+hFSH 25 IU thus induced a better follicular growth than 8 injections of 25 IU of hFSH: 4.83 mm²/follicule compared with 2.05 mm²/follicule respectively. The effect of the complex on follicular growth was constant up to D11 contrary to the treatment comprising 8 injections of FSH for which a decrease in the area of the stimulated follicles is noted. This result demonstrates a potentiating effect of CF12 in vivo in female monkeys on circulating FSH, regardless of whether it is endogenous or exogenous. Indeed, since the half-life of FSH is less than 1 hour, the effects observed when CF12 is injected with 25 IU of hFSH on the $1^{st}$ and $5^{th}$ day of treatment cannot be attributed solely to an effect on the FSH co-injected, but also reflects an effect on the endogenous FSH of the female monkey.

2/Effect of the CF12 Ligand Administered Alone after Injection of 37.5 IU of hFSH The potentiating effect of CF12 injected alone after a delay after the injection of 37.5 IU of hFSH was then studied. For this, four protocols, denoted from 1 to 4, were set up 15 days after the injection of GnRH. One female monkey was treated per protocol:

1—animal treated with 37.5 IU of hFSH for 12 days: a daily injection of 37.5 IU of human FSH (Gonal-F® pre-filled pen—Merck Serono) subcutaneously, for 12 days ("hFSH 37.5 IU X12");

2—animal treated with 37.5 IU of hFSH every day, and 400 µg of CF12 every 2 days: a daily injection of 37.5 IU of human FSH (Gonal-F® pre-filled pen—Merck Serono) subcutaneously, the 12 days, and an injection of the CF12 antibody at a dose of 400 µg, every 2 days, 20 minutes after the injection of hFSH ("hFSH 37.5 IU X12+400 µg CF12 X6");

3—animal treated with 37.5 IU of FSH every day, and 70 µg of CF12 every 2 days: a daily injection of 37.5 IU of human FSH (Gonal-F® pre-filled pen—Merck Serono) subcutaneously, the 12 days, and an injection of the CF12 antibody at a dose of 70 µg, every 2 days, 20 minutes after the injection of hFSH ("hFSH 37.5 IU X12+70 µg CF12 X6");

4—animal treated with 75 IU of FSH for 8 days: a daily injection of 75 IU of human FSH (Gonal-F® pre-filled pen—Merck Serono) subcutaneously, for 8 days ("hFSH 75 IU X8").

Figure 14:
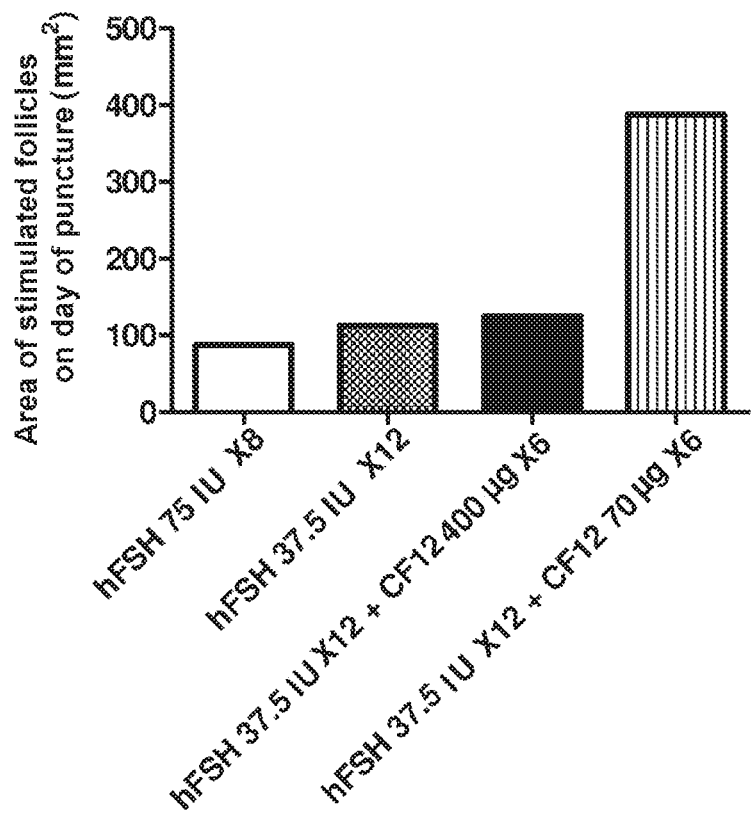
FIG. 14 represents the in vivo potentiating effect of the CF12 monoclonal antibody injected alone after 37.5 IU of hFSH, on follicular stimulation in female monkeys.

The effect of the four treatments was monitored by measuring the induced follicular growth (surface area of the follicles in mm²) by echography. FIG. 14 represents the surface areas of the stimulated follicles obtained after each treatment, on the day of the follicular puncture (D15). The strength of the follicular stimulation varies according to the treatment. It was at the maximum and very considerable in the female monkey having received the "hFSH 37.5 IU X12+70 µg CF12 X6" treatment, for which a surface area of 387.5 mm² was measured. It is 3.5 times greater than the surface area measured in the control female monkey "hFSH 37.5 IU X12" which was 112.3 mm² and 3.2 times greater than the surface area of 124.2 mm² obtained in the female monkey treated with "hFSH 37.5 IU X12+400 µg CF12 X6". The smallest area of the follicles (87.2 mm²) was obtained in the female monkey treated for 8 days with hFSH 75 IU.

The total number of follicles obtained on the day of the puncture is seven with "hFSH 37.5 IU X12+400 µg CF12 X6" and "hFSH 75 IU X8", and 10 with "hFSH 37.5 IU X12" and "37.5 IU X12+70 µg CF12 X6" (table 17).

TABLE 17

Variation in the number of stimulated follicles and in their size following the various treatments

| | Follicles <5 mm | Follicles between 5 and 7 mm | Follicles ≥7 mm | Diameter of the largest follicle (mm) |
|---|---|---|---|---|
| hFSH 37.5 IU X12 | 10 | 2 | 0 | 5.61 |
| hFSH 37.5 IU X12 + 400 µg CF12 X6 | 4 | 3 | 0 | 6.82 |
| hFSH 37.5 IU X12 + 70 µg CF12 X6 | 2 | 3 | 5 | 9.15 |
| hFSH 75 IU X8 | 4 | 3 | 0 | 6.14 |

It should be emphasized that the size of the largest follicle varies considerably between treatments. Thus, the "37.5 IU X12+70 µg CF12 X6" treatment induced the formation of 5 follicles greater than 7 mm in diameter (the largest of which has a diameter of 9.15 mm), whereas all the other treatments induced only follicles of less than 7 mm.

The number of oocytes taken by puncture was 11 oocytes with "hFSH 37.5 IU X12+400 μg CF12 X6" and "hFSH 75 IU X8", and 8 oocytes with hFSH 37.5 IU X12. The female monkey treated with hFSH 37.5 IU X12+70 μg CF12 X6 exhibited young corpora lutea on the ovaries, thereby indicating that it ovulated spontaneously before the day of the puncture.

These results demonstrate a very considerable potentiating effect of CF12 administered at the dose of 70 μg, resulting both in a follicular growth much greater than that induced by FSH alone and in a highly stimulated and advanced ovulatory response. The difference in response observed between the "hFSH 37.5 IU X12+400 μg CF12 X6" and "hFSH 37.5 IU X12+70 μg CF12 X6" treatments also indicates that the potentiating effect exerted by CF12 is dose-dependent, the 70 μg dose inducing the strongest stimulation of the ovaries.

The effect of the four treatments was also analyzed and compared by measuring the secretion of estradiol and progesterone every 48 hours from the first day of treatment up to 30 days after the follicular punctures.

Figure 15:
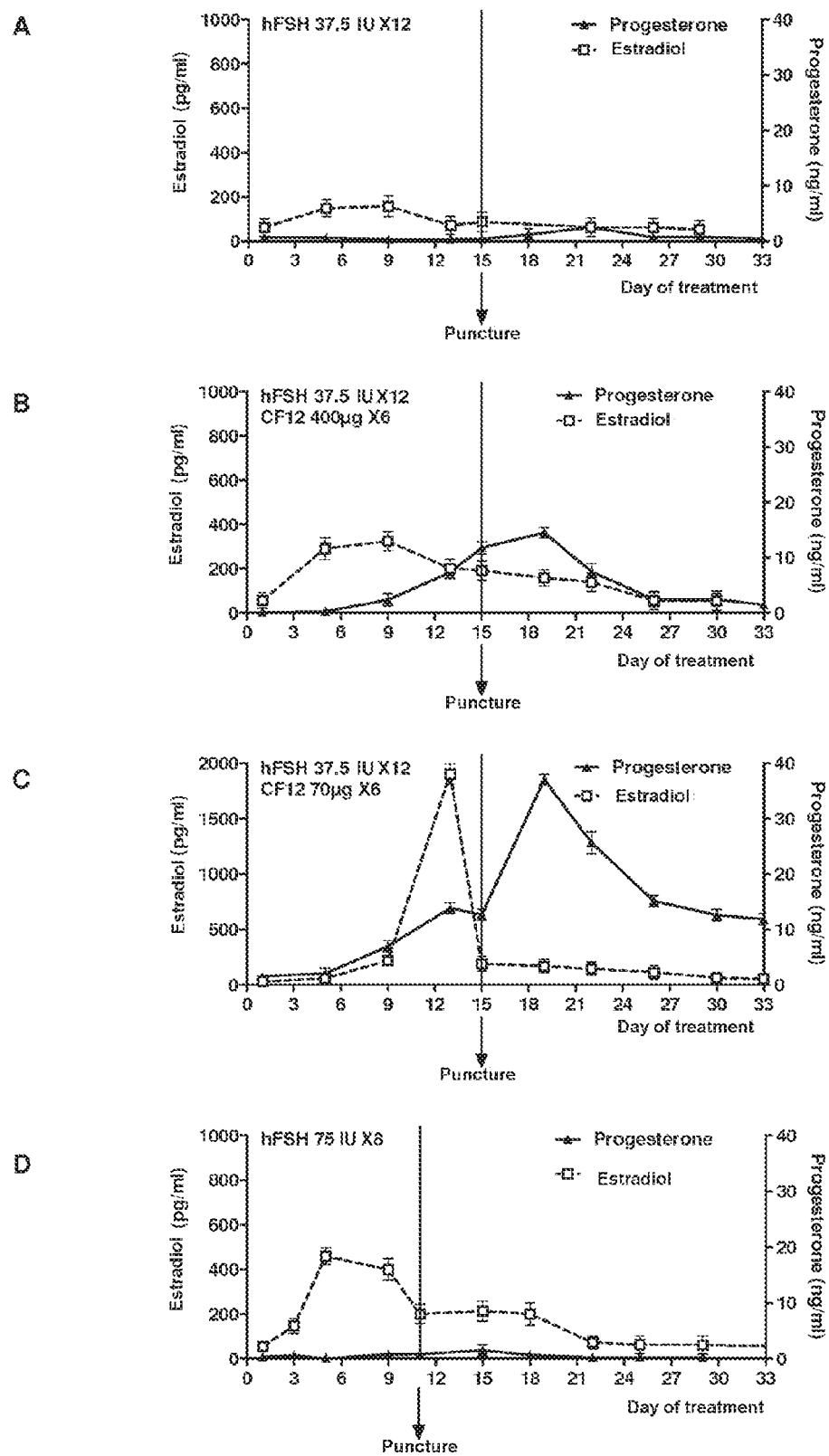
FIG. 15 represents the in vivo potentiating effect of the CF12 monoclonal antibody injected alone after 37.5 IU of hFSH, on the secretion of estradiol and progesterone in female monkeys.

The results are shown in FIG. 15, each treatment being presented by a graph (A-B-C-D) showing the estradiol and progesterone secretion profiles obtained for each female monkey throughout the cycle.

The female monkeys treated with 37.5 IU of hFSH alone (FIG. 15A) or in combination with a treatment of CF12 at 400 μg (FIG. 15B) and 70 μg (FIG. 15C) present estradiol secretion profiles which will be significantly different from one another (**$p<0.0001$, Two-way ANOVA). At D9, the concentration is respectively 157 pg/ml, 323 pg/ml and 220 pg/ml indicating a better estrogenic response with the treatments combining CF12. At D13, two days before the follicle puncture, the estradiol concentration is respectively 70 pg/ml (FIG. 15A), 200 pg/ml (FIG. 15B) and 1950 pg/ml (FIG. 15C). In comparison, it is 395 ng/ml in the female monkey treated with hFSH 75 IU X8 (FIG. 15D**), two days before the follicular puncture. These results demonstrate a very considerable potentiating effect of CF12 on the estrogen response, resulting in an increase of the estradiol peak by a factor of 3 with the 400 μg dose of CF12 and by a factor of 28 with the 70 μg dose of CF12 relative to the control treatment with FSH alone. The considerable estradiol peak observed at D13 in the case of "hFSH 37.5 IU X12+70 μg CF12 X6" may explain the induction of an early ovulation that occurred before the follicular puncture.

The progesterone secretion profiles, reflecting the establishment of corpora lutea of good quality, were measured. The comparison of FIGS. 15A, 15B and 15C show very clearly the dose-dependent increase in the progesterone level in the female monkeys treated with CF12 and FSH compared with the female monkey treated with FSH alone. Thus, at D19, four days after the follicular puncture, the progesterone concentration is 2.4 ng/ml with FSH alone (FIG. 15A), 14.5 ng/ml (X6) with CF12 400 μg (FIG. 15B) and reaches 37 ng/ml (X15) with CF12 70 μg (FIG. 15C). By comparison, the progesterone level measured 4 days after the follicular puncture in the female monkey treated with FSH alone at 75 IU X8 is 1.5 ng/ml (FIG. 15D) and is not statistically different than the 37.5 IU X12 treatment. Conversely, the treatments with CF12 400 μg and 70 μg induce progesterone levels that are statistically different than the treatments with FSH alone (**** $p<0.0001$, Two-way ANOVA).

These results demonstrate very clearly a potentiating effect of CF12 on progesterone blood levels, reflecting a better quality of corpora lutea in the female monkeys having received the antibody. The important role of progesterone in the preparation of the endometrium, implantation and early development of the embryo make it an important asset in animal species and for application in women.

Given the very short half-life of FSH (less than one hour), all of the results (with 25 or 37.5 IU of hFSH) confirm that the CF12 antibody is capable of exerting a potentiating effect in vivo on circulating FSH, whether it is endogenous or exogenous. The very considerable effects observed in the female monkey treated with 70 μg of antibody are in fact associated with a "long duration" action of the antibody on the endogenous hormone of the female monkey.

By virtue of these results, we also demonstrate that the CF12 antibody could open the way to the establishment of a new treatment for induction of ovulation clinically in human beings, particularly in ART treatments, whether for inducing mono ovulation in the context of artificial insemination or poly ovulation in the context of in vitro fertilization (IVF) by defining a suitable dosage.

Example 6: Prediction of the Epitope Recognized by the CF12 Ligand of the Invention and Prediction of its Paratope The epitope of the CF12 antibody was determined on the gonadotropic hormones of various species using a protein-docking algorithm based on protein structure modeling using a Voronoï diagram and optimization by various score function evolutionary learning methods making it possible to differentiate native and non-native conformations (Bernauer et al., Bioinformatics 2007, 5:555) [14], (Bernauer et al., Bioinformatics 2008, 24:652) [15], (Bourquard et al., PLoS One 2011, 6:e18541) [16] and (Bourquard et al., Sci. Reports 2015, 5:10760) [17].

Each antibody was docked with human FSH (hFSH), human LH (hLH), human CG (hCG), ovine FSH (oFSH) and ovine LH (oLH), porcine FSH (pFSH) and porcine LH (pLH). The crystallographic structures of hFSH and of hCG are available in the Protein Data Bank (PDB): 4 MQW and 1 QFW respectively. The structure of human FSH complexed with the extracellular domain of the human FSH receptor was used (Fan and Hendrickson, Nature 2005, 433:269) [18]. For the other hormones (hLH, oFSH, oLH, pFSH and pLH), homology models were produced and then used for the docking.

Since the 3D structure of the CF12 antibody is not available, the study was carried out using the sequences of the monovalent VH and VL fragments of CF12. For this, variable part homology models were produced. The VH and VL models were produced separately, from different structures, and their relative orientation was determined from the structure having served as a support for the VH modeling. The structures used for the homology models are available in the Protein Data Bank (PDB): 1PLV for the VH of CF12 and 3TT1 for the VL of CF12.

The docking results are shown in FIG. 16. It appears that the CF12 ligand docks similarly on the seven target hormones. The epitope is defined by several regions located discontinuously on the alpha- and beta-subunits of the gonadotropins studied. The epitope also involves the sequence His7-Cys8-Ser9-Asn10 of the ectodomain of the human FSH receptor. The epitope of the CF12 ligand is thus very conformational: it consists both of several regions of the alpha- and beta-subunits of the hormone and of a sequence of the receptor. All of these discontinuous regions are spatially close in the native conformation of the hormone and of its activated receptor.

The various residues of the hormone and of the receptor that are involved in the interface with the CF12 ligand are surrounded by rectangles in FIG. 16. The two residues denoted by a shaded area on the alpha-subunit of hFSH are involved in the main interaction and thus have a major role in the antibody/antigen recognition: these are the glutamic acid in position 9 (Glu9) and the phenylalanine in position 33 (Phe33) of the alpha-subunit of hFSH. These two residues are identical and recognized in the sequence of the other target hormones. Among the other residues of the alpha-subunit, that are involved in the interface, a region The two VH and VL chains are involved in the recognition of the hormone, via their three CDRs and some residues of their frameworks.

For the main interaction, the Glu9 residue of the alpha-subunit of hFSH is recognized respectively by the Tyr102 and Asp104 residues of CDR3 of the VH chain and by the Leu50 residue of the VL chain. The Phe33 residue of the alpha-subunit is recognized by the Ser31 and Tyr33 residues of CDR1 of the VH chain and by the Tyr52 residue of CDR2 of the VH chain.

TABLE 18

Epitope and Paratope of the CF12 ligand.

| | | Paratope of the CF12 antibody |
|---|---|---|
| Epitope regions on human FSH | | |
| αFSH | Gln5 Asp6 Cys7 Pro8 <u>Glu9</u> | VH: <u>CDR3</u> |
| | Cys10 Thr11 Leu12 Gln13 | VL: CDR1-CDR2-CDR3-FR |
| | Met29 - - - <u>Phe33</u> - Arg35 | VH: CDR1-<u>CDR2</u> |
| | | VL: FR |
| | Glu56 | VH: CDR2 |
| | Ala81 | VL: FR |
| βFSH | Asn1 Ser2 - - - Thr6 | VH: CDR2-CDR3-FR |
| | Asn7 Ile8 Thr9 | VL: CDR1-CDR3 |
| | Ala29 Gly30 Tyr31 - Tyr33 | VH: CDR1-CDR3 |
| | | VL: CDR1 |
| | Gly100 Pro101 Ser102 - - | VH: CDR1-CDR2-FR |
| | - - - Glu108 Met109 | |
| Epitope regions on the human FSH receptor | | |
| | His7 Cys8 Ser9 Asn10 | VH: CDR1-FR | comprising nine residues including Glu9 is noted. It is the Gln5-Asp6-Cys7-Pro8-Glu9-Cys10-Thr11-Leu12-Gln13 motif.

The presence of the arginine residue in position 35 (Arg35) and the glutamic acid residue in position 56 (Glu56), which are spatially close in the native hormone, is also noted in the epitope. These two residues fix the C-terminal end of the beta-subunit, thus securing the "seat belt" around the alpha-subunit. These two residues are constantly present and recognized in all the target hormones. They play an important role in the stability and the bioactivity of the hormone. By virtue of this mechanism, the binding of the antibody to these residues would thus make it possible to increase the stability of the FSH dimer.

The CF12 ligand also recognizes residues 100 to 102 and 108-109 of the C-terminal end of the beta-subunit which constitutes the seat belt. Since the role of this seat belt is to stabilize the association of the alpha/beta dimer of the hormone, the binding of the CF12 ligand to these two residues is also thought to contribute to making safe the closure of the seat belt, thus allowing better stability of the dimer, which is essential to the bioactivity of the hormone.

Another characteristic of the epitope of the CF12 ligand is the involvement of residues 7 to 10 (His7-Cys8-Ser9-Asn10) of the N-terminal region of the human FSH receptor in the interface recognized by CF12. The binding of the CF12 ligand is also thought to contribute, via this mechanism, to promoting the interaction of the hormone on its receptor and leading to the establishment of a "potentiating" effect.

Table 18 gives the various regions of the paratope of the CF12 ligand. The numbering used is that of the sequences SEQ ID NO:2 and SEQ ID NO:4.

Table 18: Various regions constituting the epitope of the CF12 ligand and those constituting its paratope. The residues involved in the main interaction are indicated by underline.

The interaction on the Arg35 and Glu56 residues of the alpha-subunit involves several residues of the VH chain. The Ser30 residue of CDR1 and the Tyr52, and Gly54-Thr55 residues of CDR2 interact with Arg35. The Tyr52 residue of CDR2 also interacts with Glu56 of the alpha-subunit.

The interaction on the C-terminal end of the beta-chain (seat belt) involves several residues of the VH chain: the Ser30 residue of CDR1, the Gly54 residue of CDR2 and the Asp73-Thr74-Ser75 residues of framework 3.

Only the VH chain is also involved in the recognition of the ectodomain of the FSH receptor, particularly its CDR1 with the glycine in position 26 (Gly26), and certain residues of framework 1 (Gln1-Gly2-Gln3, Lys23-Thr24-Ser25) and of framework 3 (Ser75).

In conclusion, the CF12 ligand is characterized in that it recognizes a highly conformational epitope involving the alpha-subunit of hFSH, the beta-subunit and particularly its C-terminal end forming the seat belt, and also the ectodomain of the FSH receptor. The VH chain is essentially involved in the interaction with the receptor and the VL chain in the interaction with the hormone. This epitope enables the CF12 ligand, on the one hand, to stabilize the hormone dimer association and, on the other hand, to stabilize the binding of the hormone to its receptor. These two mechanisms are complimentary for producing a better interaction of the hormone on its receptor and could constitute the bases of the potentiating effect of the CF12 ligand on the gonadotropins.

Example 7: Construction, Production and Characterization of Various Fragments of the Cf12 Ligand of the Invention Various fragments of the CF12 antibody were constructed in order to evaluate their capacity to potentiate the biological activity of ovine FSH and human FSH. A fragment comprising the light variable chain alone, called "CF12 VL", a fragment comprising the heavy variable chain alone, called "CF12 VH" and a "reverse CF12 scFv" constructed in a reverse VL-VH order compared with the VH-VL sequence of the CF12 scFv (SEQ ID NO: 10 and SEQ ID NO: 11) of reference described in example 1, paragraph 4 of the present invention were produced.

1/Antibody Fragment Construction and Production

The synthetic genes encoding the CF12 VL and reverse CF12 scFv fragments derived from the CF12 antibody were synthesized by ATG:Biosynthetics GmbH (Germany). The reverse CF12 scFv consists of the CF12 VL of the CF12 scFv-linker-CF12VH of the CF12 scFv fusion. Each synthetic gene is designed by the fusion of the sequence of the pSW1 plasmid [7], included between the HindIII site and the end of the sequence encoding the PelB protein and the sequence of the protein of interest to be synthesized (SEQ ID NO: 27 and SEQ ID NO: 31), flanked by the XhoI restriction site. The sequences are inserted between the HindIII and XhoI sites of the pSW1 plasmid. The codons were optimized for expression in *E. coli*.

The pSW1CF12 VH expression plasmid was obtained by insertion, into the pSW1 plasmid [7] at the PstI-XhoI sites, of the fragment resulting from the digestion by these enzymes of the pSW1 reverse CF12 scFv plasmid.

After verification by sequencing of the quality of the constructs, the pSW1-CF12 VL, pSW1-CF12 VH and pSW1 reverse CF12 scFv plasmids were used to transform, by heat shock, HB2151 bacteria (T53040, Interchim, France) made competent [8].

TABLE 19

Nucleotide and peptide sequences of the CF12 VL CF12 VL

| | |
|---|---|
| Nucleotide sequence SEQ ID NO: 27 | GATATTCAGATGACCCAGACCCCTGCGAGCCT GGCAGTGTCACTGGGCCAACGCGCAACCATCT CGTGTAAAGCCTCGCAGAGCGTGGATTATGAC GGCGATAGCTACATGAACTGGTATCAGCAAAA GCCTGGTCAACCGCCGAAGCTGCTGATTTACG CCGCCAGCAACCTGGAATCGGGCATCCCGGCC CGTTTTAGCGGCTCAGGCTCGGGTACTGACTT CACGCTGAACATTCACCCGGTAGAAGAAGAAG ACGCGGCCACGTATTACTGCCAGCAAAGCAAT GAAGACCCGTACACTTTTGGCGGCGGCACGAA ACTTGAGATCAAACACCATCACCATCACCATT AA |
| Peptide sequence SEQ ID NO: 28 | DIQMTQTPASLAVSLGQRATISCKASQSVDYD GDSYMNWYQQKPGQPPKLLIYAASNLESGIPA RFSGSGSGTDFTLNIHPVEEEDAATYYCQQSN EDPYTFGGGTKLEIKHHHHHH* |

TABLE 20

Nucleotide and peptide sequences of the CF12 VH CF12 VH

| | |
|---|---|
| Nucleotide sequence | CAGGTGCAGCTGCAGCAGTCGGGTGGCGCAGA GCTGGTGAAACCGGGTGCGAGCGTTAAACTGA GCTGCAAAACTAGCGGCTTTACCTTTAGCTCG TCATATATTTCGTGGCTGAAGCAGAAACCGGG CCAGTCACTGGAATGGATTGCGTGGATCTACG CAGGCACGGGTGGCACCTCATATAATCAGAAA TTCACCGGTAAAGCGCAACTGACGGTCGATAC CAGCAGCAGCACGGCGTACATGCAGTTCAGCT CGCTGACCACTGAAGATAGCGCAATCTACTAT TGTGCACGCCATGGTTCGTACTTCGACTATTG GGGCCAGGGCACCACCCTGACCGTTTCAAGCC ACCATCACCATCACCATTAA |
| Peptide sequence SEQ ID NO: 30 | QVQLQQSGGAELVKPGASVKLSCKTSGFTFSS SYISWLKQKPGQSLEWIAWIYAGTGGTSYNQK FTGKAQLTVDTSSSTAYMQFSSLTTEDSAIYY CARHGSYFDYWGQGTTLTVSSHHHHHH* |

TABLE 21

Nucleotide and peptide sequences of reverse CF12 scFv reverse CF12 scFv

| | |
|---|---|
| Nucleotide sequence SEQ ID NO: 31 | GATATTCAGATGACCCAGACCCCTGCGAGCCTGG CAGTGTCACTGGGCCAACGCGCAACCATCTCGTG TAAAGCCTCGCAGAGCGTGGATTATGACGGCGAT AGCTACATGAACTGGTATCAGCAAAAGCCTGGTC AACCGCCGAAGCTGCTGATTTACGCCGCCAGCAA CCTGGAATCGGGCATCCCGGCCCGTTTTAGCGGC TCAGGCTCGGGTACTGACTTCACGCTGAACATTC ACCCGGTAGAAGAAGAAGACGCGGCCACGTATTA CTGCCAGCAAAGCAATGAAGACCCGTACACTTTT GGCGGCGGCACGAAACTTGAGATCAAAGGTGGTG GTGGTAGCGGTGGTGGTGGTTCAGGTGGCGGCGG CTCACAGGTGCAGCTGCAGCAGTCGGGTGGCGCA GAGCTGGTGAAACCGGGTGCGAGCGTTAAACTGA GCTGCAAAACTAGCGGCTTTACCTTTAGCTCGTC ATATATTTCGTGGCTGAAGCAGAAACCGGGCCAG TCACTGGAATGGATTGCGTGGATCTACGCAGGCA CGGGTGGCACCTCATATAATCAGAAATTCACCGG TAAAGCGCAACTGACGGTCGATACCAGCAGCAGC ACGGCGTACATGCAGTTCAGCTCGCTGACCACTG AAGATAGCGCAATCTACTATTGTGCACGCCATGG TTCGTACTTCGACTATTGGGGCCAGGGCACCACC CTGACCGTTTCAAGCCACCATCACCATCACCATT AA |
| Peptide sequence SEQ ID NO: 32 | DIQMTQTPASLAVSLGQRATISCKASQSVDYDGD SYMNWYQQKPGQPPKLLIYAASNLESGIPARFSG SGSGTDFTLNIHPVEEEDAATYYCQQSNEDPYTF GGGTKLEIKGGGGSGGGGSGGGGSQVQLQQSGGA ELVKPGASVKLSCKTSGFTFSSSYISWLKQKPGQ SLEWIAWIYAGTGGTSYNQKFTGKAQLTVDTSSS TAYMQFSSLTTEDSAIYYCARHGSYFDYWGQGTT LTVSSHHHHHH* |

The fragment production was carried out according to the method previously described in example 1 of the present invention.

2/In Vitro Measurement of the Effect of the CF12 VL, CF12 VH and Reverse CF12 scFv Fragments on the Bioactivity of FSH The in vitro effect of the "CF12 VL", "CF12 VH" and "reverse CF12 scFv" fragments on the bioactivity of human FSH was studied with the HEK293 cell line stably transfected with the human FSH receptor and the Glosensor® system according to the protocol previously described in example 2 of the present invention. The "CF12 VL" and "CF12 VH" fragments alone or as a mixture were tested at 40 nM each. The reverse CF12 scFv was tested at the concentration of 80 nM, just like the reference CF12 scFv. The human FSH was tested at 0.1 nM.

Figure 17:
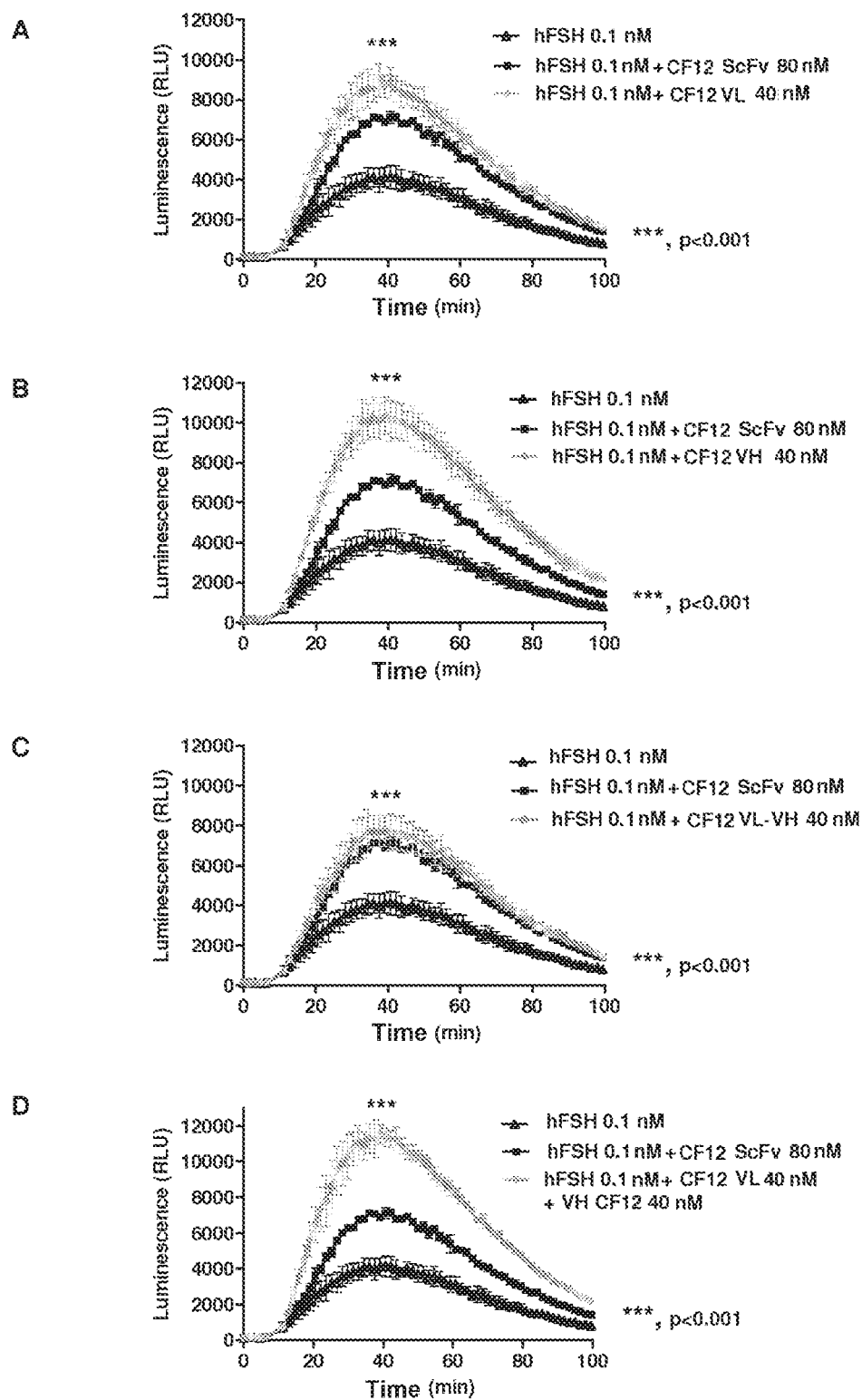
FIG. 17 represents the in vitro potentiating effect of various fragments of the CF12 monoclonal antibody on the bioactivity of hFSH.

FIG. 17 shows the cAMP production kinetics curves expressed in relative luminescence units as a function of time (in minutes) obtained in the presence of 0.1 nM of human FSH (hFSH) alone or complexed with the various CF12 fragments. Four conditions were compared with hFSH alone: the hFSH+CF12 VL complex (FIG. 17A), the hFSH+CF12 VH complex (FIG. 17B), the hFSH+reverse CF12 scFv complex (FIG. 17C) and the complex of hFSH with an equimolar mixture of 40 nM of CF12 VL and of 40 nM of CF12 VH (FIG. 17D). The levels of luminescent response are compared at 40 min of stimulation.

It is observed that the "CF12 VL" fragment at the concentration of 40 nM complexed with 0.1 nM hFSH exerts a very significant potentiating effect ($p<0.001$), which increases the cell response by 218% in a manner comparable to the CF12 scFv (180% increase) compared with the stimulation with hFSH alone (FIG. 17A). The "CF12 VH" fragment at the concentration of 40 nM complexed with 0.1 nM hFSH exerts a very significant potentiating effect ($p<0.001$), which increases the cell response by 250% in a manner greater than the CF12 scFv (180% increase) compared with the stimulation with hFSH alone (FIG. 17B).

The reverse CF12 scFv (FIG. 17C) potentiates the action of FSH in a manner identical to the reference CF12 scFv, both giving an increase in the luminescent signal of 180% compared with the response to FSH; this effect is significant ($p<0.001$).

Finally, the mixture of the two CF12 VH+CF12 VL fragments (FIG. 17D) complexed with hFSH induces a significant increase ($p<0.001$) in the cell response of 278%, which is greater than the reference CF12 scFv (180% increase).

All of these results indicate that the isolated VL or VH fragments are capable of exerting a potentiating effect on the bioactivity of FSH. In so doing, they validate the prediction of the interaction model, described in example 6 of the present invention, showing the involvement of the two variable chains in the interaction on the FSH/receptor complex. The mixture of the two VL and VH fragments exerts the greatest potentiating effect in this assay.

3/In Vivo Measurement of the Potentiating Effect of the CF12 VL, CF12 VH and Reverse CF12 scFv Fragments on the Bioactivity of FSH in the Female Rat After having been characterized in vitro, the potentiating effect of the various CF12 fragments on the bioactivity of hFSH was studied in vivo, in the female rat.

In order to measure the FSH bioactivity, the protocol used was that of the biological assay of Steelman and Pohley (Steelman S L, Pohley F M. Endocrinology, 53:604-616. 1953) [12] as described in example 3 of the present invention. Each batch comprised five female rats.

Figure 18:
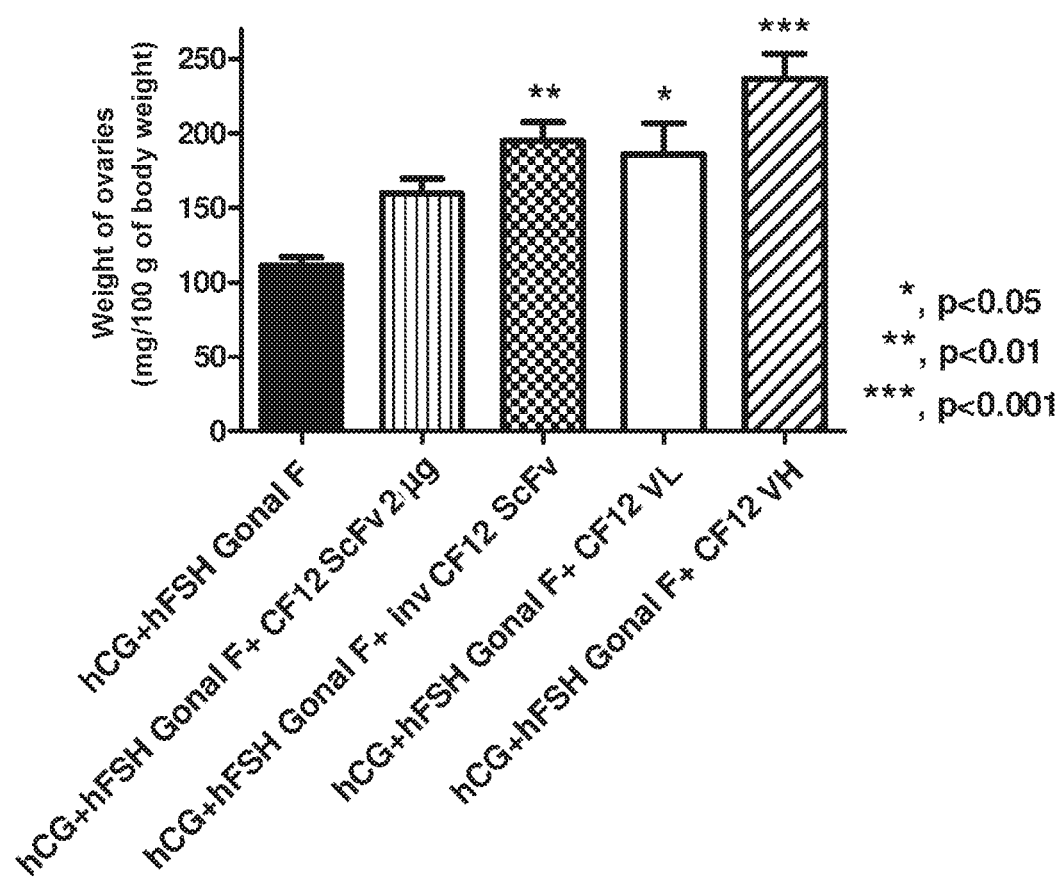
FIG. 18 represents the in vivo potentiating effect, in the female rat, of various fragments of the CF12 monoclonal antibody on the bioactivity of hFSH.

The results are shown in FIG. 18. The batch treated with hFSH complexed with the reverse CF12 scFv gave a mean weight of the ovaries of 195±15 mg/100 g of body weight, slightly greater than that of the batch treated with the reference hFSH/CF12 scFv complex with (160±5 mg), that is to say an increase of 175% compared with the batch having received the hormonal treatment alone ($p<0.01$). The batches treated with the CF12 VL and CF12 VH fragments complexed with hFSH had a mean weight of the ovaries of 186±24 mg and 237±15 mg respectively, that is to say an increase of 167% and 213% compared with the batch having received the hormonal treatment alone ($p<0.05$ and $p<0.001$).

These results demonstrate that the order of construction of the scFv (VL-VH versus VH-VL) complexed with hFSH does not affect the potentiating properties of the scFv on the bioactivity of FSH. The results also demonstrate very significantly that the variable chains of CF12, particularly the VL fragment, are capable of potentiating, in vivo and in vitro, the bioactivity of the hormone. This reflects the respective involvement of the two chains in this effect, as predicted by the interaction model described in example 7 of the present invention.

The invention claimed is:

1. A follicle-stimulating hormone (FSH) ligand which potentiates the bioactivity of FSH, of luteinizing hormone (LH), and of chorionic gonadotropin (CG),
wherein said ligand is an antibody or a fragment thereof, and
the heavy chain variable domain of the antibody or the fragment contains the following CDRs:

```
VH-CDR1, defined by the sequence
                            (SEQ ID NO: 5)
GFTFSSSY;

VH-CDR2, defined by the sequence
                            (SEQ ID NO: 6)
IYAGTGGT;

VH-CDR3, defined by the sequence
                            (SEQ ID NO: 7)
ARHGSYFDY;
``` and
the light chain variable domain of the antibody or the fragment contains the following CDRs:

```
VL-CDR1, defined by the sequence
                            (SEQ ID NO: 8)
QSVDYDGDSY;

VL-CDR2, defined by the sequence
AAS;

VL-CDR3, defined by the sequence
                            (SEQ ID NO: 9)
QQSNEDPYT.
```

2. The ligand of claim 1, wherein the ligand is the CF12 monoclonal antibody produced by the CNCM I-4803 hybridoma.

3. The ligand of claim 1, wherein the peptide sequence of the scFv is the sequence of SEQ ID NO: 11.

4. A ligand-gonadotropin complex chosen from:
(A) a complex of the ligand of claim 1 with FSH;
(B) a complex of a second antibody fragment with FSH;
(C) a complex of the ligand of claim 1 with LH or the chorionic gonadotropin (CG) hormone; or
(D) a complex of a second antibody fragment with LH or the chorionic gonadotropin (CG) hormone,
wherein the second antibody fragment contains a heavy chain variable domain comprising the following CDRs:

```
VH-CDR1, defined by the sequence       (SEQ ID NO: 5)
GFTFSSSY;

VH-CDR2, defined by the sequence       (SEQ ID NO: 6)
IYAGTGGT;
and

VH-CDR3, defined by the sequence       (SEQ ID NO: 7)
ARHGSYFDY;
``` or
the second antibody fragment contains a light chain variable domain comprising the following CDRs:

```
VL-CDR1; defined by the sequence       (SEQ ID NO: 8)
QSVDYDGDSY;

VL-CDR2, defined by the sequence
AAS;
and

VL-CDR3, defined by the sequence       (SEQ ID NO: 9)
OQSNEDRYT.
```

5. A method of treating infertility or hypofertility in a mammal in need thereof, the method comprising administering to the mammal an effective amount of the ligand-gonadotropin complex of claim 4 and optionally an FSH and/or an LH and/or a CG.

6. A method of stimulating procreation in a female mammal in need thereof, the method comprising administering to the female mammal an effective amount of the ligand-gonadotropin complex of claim 4 and optionally an FSH and/or an LH and/or a CG.

7. A pharmaceutical composition comprising a complex as claimed in claim 4 and a pharmaceutically acceptable carrier.

8. The pharmaceutical composition of claim 7 further comprising an FSH and/or an LH and/or a CG.

9. A method of inducing ovulation or polyovulation in a female mammal in need thereof, the method comprising administering to the female mammal an effective amount of the complex of claim 4 and optionally an FSH and/or an LH and/or a CG.

10. A method of increasing circulating endogenous progesterone level in a female mammal in need thereof, the method comprising administering to the female mammal an effective amount of the complex of claim 4 and optionally an FSH and/or an LH and/or a CG.

11. A method of inducing ovulation or polyovulation in a female mammal in need thereof, the method comprising administering to the female mammal an effective amount of the ligand of claim 1, or a second antibody fragment, and optionally an FSH and/or an LH and/or a CG, wherein the second antibody fragment contains a heavy chain variable domain comprising the following CDRs:

```
VH-CDR1, defined by the sequence      (SEQ ID NO: 5)
GFTFSSSY;

VH-CDR2, defined by the sequence      (SEQ ID NO: 6)
IYAGTGGT;
and

VH-CDR3, defined by the sequence      (SEQ ID NO: 7)
ARHGSYFDY.
```

12. A method of increasing circulating endogenous progesterone level in a female mammal in need thereof, the method comprising administering to the female mammal an effective amount of the ligand of claim 1, or a second antibody fragment, and optionally an FSH and/or an LH and/or a CG, wherein the second antibody fragment contains a heavy chain variable domain comprising the following CDRs:

```
VH-CDR1, defined by the sequence      (SEQ ID NO: 5)
GFTFSSSY;

VH-CDR2, defined by the sequence      (SEQ ID NO: 6)
IYAGTGGT;
and

VH-CDR3, defined by the sequence      (SEQ ID NO: 7)
ARHGSYFDY.
```

13. A pharmaceutical composition comprising the ligand of claim 1 and a pharmaceutically acceptable carrier.

14. The pharmaceutical composition as claimed in claim 13, wherein it also comprises an FSH and/or an LH and/or a CG.

15. A method of treating infertility hypofertility in a mammal in need thereof, the method comprising administering to the mammal an effective amount of the ligand of claim 1 or a second antibody fragment, and optionally an FSH and/or an LH and/or a CG, wherein the second antibody fragment contains a heavy chain variable domain comprising the following CDRs:

```
VH-CDR1, defined by the sequence      (SEQ ID NO: 5)
GFTFSSSY;

VH-CDR2, defined by the sequence      (SEQ ID NO: 6)
IYAGTGGT;
and

VH-CDR3, defined by the sequence      (SEQ ID NO: 7)
ARHGSYFDY.
```

16. A method of stimulating procreation in a female mammal in need thereof, the method comprising administering to the female mammal an effective amount of the ligand of claim 1 or a second antibody fragment, and optionally an FSH and/or an LH and/or a CG, wherein the second antibody fragment contains a heavy chain variable domain comprising the following CDRs:

```
VH-CDR1, defined by the sequence      (SEQ ID NO: 5)
GFTFSSSY;

VH-CDR2, defined by the sequence      (SEQ ID NO: 6)
IYAGTGGT;
and

VH-CDR3, defined by the sequence      (SEQ ID NO: 7)
ARHGSYFDY.
```

17. The ligand of claim 1, wherein the ligand is selected from the group consisting of: Fab, Fab', F(ab')2, Fv, dsFv, scFv, diabodies, triabodies, and tetrabodies.

18. A method for increasing circulating endogenous progesterone level in a female mammal in need thereof, comprising administering to the female mammal an effective amount of the ligand as claimed in claim 1.

19. The method of claim 18, further comprising administering an FSH and/or an LH and/or a CG.

20. A method for treating infertility or hypofertility in a mammal in need thereof, comprising administering to the mammal an effective amount of the ligand as claimed in claim 1.

21. The method of claim 20, further comprising administering an FSH and/or an LH and/or a CG.

22. A method for stimulating procreation in a female mammal in need thereof, comprising administering to the mammal an effective amount of the ligand as claimed in claim 1.

23. The method of claim 22, further comprising administering an FSH and/or an LH and/or a CG.

24. A method of inducing ovulation or polyovulation in a female mammal in need thereof, comprising administering to the female mammal an effective amount of the ligand as claimed in claim 1.

25. The method of claim 24 further comprising administering an FSH and/or an LH and/or a CG.

26. A follicle-stimulating hormone (FSH) ligand which potentiates the bioactivity of FSH, of luteinizing hormone (LH), and of chorionic gonadotropin (CG), wherein said ligand is an antibody or a fragment thereof, and the heavy chain variable domain of the antibody or the fragment contains the sequence of SEQ ID NO: 2 or 30; and the light chain variable domain of the antibody or the fragment contains the sequence SEQ ID NO:4 or 28.

27. A pharmaceutical composition comprising the ligand claimed in claim 26 and a pharmaceutically acceptable carrier,
and optionally an FSH and/or an LH and/or a CG.

28. A method for increasing circulating endogenous progesterone level in a female mammal in need thereof, comprising administering to the female mammal an effective amount of the ligand as claimed in claim 26 and optionally an FSH and/or an LH and/or a CG.

29. A method for treating infertility or hypofertility in a mammal in need thereof, comprising administering to the mammal an effective amount of the ligand as claimed in claim 26 and optionally an FSH and/or an LH and/or a CG.

30. A method for stimulating procreation in a female mammal in need thereof, comprising administering to the mammal an effective amount of the ligand as claimed in claim 26 and optionally an FSH and/or an LH and/or a CG.

31. A method of inducing ovulation or polyovulation in a female mammal in need thereof, comprising administering to the female mammal an effective amount of the ligand as claimed in claim 26 and optionally an FSH and/or an LH and/or a CG.

32. A follicle-stimulating hormone (FSH) ligand which potentiates the bioactivity of FSH, of luteinizing hormone (LH), and of chorionic gonadotropin (CG),
wherein said ligand is an antibody fragment, and
wherein the antibody fragment contains the following CDRs:

```
VH-CDR1, defined by the sequence      (SEQ ID NO: 5)
GFTFSSSY;

VH-CDR2, defined by the sequence      (SEQ ID NO: 6)
IYAGTGGT;
and

VH-CDR3, defined by the sequence      (SEQ ID NO: 7)
ARHGSYFDY.
```

33. The ligand of claim 32, wherein the antibody fragment is a domain $V_H$H or a heavy chain variable domain.

34. A method for treating infertility or hypofertility in a mammal in need thereof, comprising administering to the mammal an effective amount of the ligand as claimed in claim 32.

35. The method as claimed in claim 34, further comprising an FSH and/or an LH and/or a CG.

36. A method for stimulating procreation in a female mammal in need thereof, comprising administering to the female mammal an effective amount of the ligand as claimed in claim 32.

37. The method as claimed in claim 36, further comprising administering an FSH and/or an LH and/or a CG.

38. A pharmaceutical composition comprising a ligand as claimed in claim 32 and a pharmaceutically acceptable carrier.

39. The pharmaceutical composition as claimed in claim 38, wherein it also comprises an FSH and/or an LH and/or a CG.

40. A method for inducing ovulation or polyovulation in a female mammal in need thereof, comprising administering to the female mammal an effective amount of the ligand of claim 32.

41. The method as claimed in claim 40, further comprising administering to the female mammal an FSH and/or an LH and/or a CG.

42. A method for increasing circulating endogenous progesterone level in a female mammal in need thereof, comprising administering to the female mammal an effective amount of the ligand as claimed in claim 32.

43. The method as claimed in claim 42, further comprising administering to the female mammal an FSH and/or an LH and/or a CG.

44. A follicle-stimulating hormone (FSH) ligand which potentiates the bioactivity of FSH, of luteinizing hormone (LH), and of chorionic gonadotropin (CG),
wherein said ligand is an antibody fragment, and
the heavy chain variable domain of the antibody fragment contains the sequence of SEQ ID NO: 2 or 30; or
the light chain variable domain of the antibody fragment contains the sequence SEQ ID NO: 28.

45. A pharmaceutical composition comprising the ligand as claimed in claim 44 and a pharmaceutically acceptable carrier,
and optionally an FSH and/or an LH and/or a CG.

46. A method for increasing circulating endogenous progesterone level in a female mammal in need thereof, comprising administering to the female mammal an effective amount of the ligand as claimed in claim 44 and optionally an FSH and/or an LH and/or a CG.

47. A method for treating infertility or hypofertility in a mammal in need thereof, comprising administering to the mammal an effective amount of the ligand as claimed in claim 44 and optionally an FSH and/or an LH and/or a CG.

48. A method for stimulating procreation in a female mammal in need thereof, comprising administering to the mammal an effective amount of the ligand as claimed in claim 44 and optionally an FSH and/or an LH and/or a CG.

49. A method of inducing ovulation or polyovulation in a female mammal in need thereof, comprising administering to the female mammal an effective amount of the ligand as claimed in claim 44 and optionally an FSH and/or an LH and/or a CG.

* * * * *

SEQUENCE LISTING

<160> NUMBER OF SEQ ID NOS: 43

<210> SEQ ID NO 1
<211> LENGTH: 348
<212> TYPE: DNA
<213> ORGANISM: Artificial Sequence
<220> FEATURE:
<223> OTHER INFORMATION: VH CF12

<400> SEQUENCE: 1

```
cagggtcaga tgcagcagtc tggagctgag ctggtgaagc ctggggcttc agtgaagctg      60
tcctgcaaga cttctggctt caccttcagc agtagctata taagttggtt gaagcaaaag     120
cctggacaga gtcttgagtg gattgcatgg atttatgctg gaactggtgg tactagctat     180
aatcagaagt tcacaggcaa ggcccaactg actgtagaca tcctccag cacagcctac      240 atgcaattca gcagcctgac aactgaggac tctgccatct attactgtgc aagacacggg     300
tcctactttg actactgggg ccaaggcacc actctcacag tctcctca                  348
```

<210> SEQ ID NO 2
<211> LENGTH: 116
<212> TYPE: PRT
<213> ORGANISM: Artificial Sequence
<220> FEATURE:
<223> OTHER INFORMATION: VH CF12

<400> SEQUENCE: 2

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Gly Thr Ser Tyr Asn Gln Lys Phe
    50                  55                  60

Thr Gly Lys Ala Gln Leu Thr Val Asp Thr Ser Ser Ser Thr Ala Tyr
65                  70                  75                  80

Met Gln Phe Ser Ser Leu Thr Thr Glu Asp Ser Ala Ile Tyr Tyr Cys
                85                  90                  95

Ala Arg His Gly Ser Tyr Phe Asp Tyr Trp Gly Gln Gly Thr Thr Leu
            100                 105                 110

Thr Val Ser Ser
        115

<210> SEQ ID NO 3
<211> LENGTH: 333
<212> TYPE: DNA
<213> ORGANISM: Artificial Sequence
<220> FEATURE:
<223> OTHER INFORMATION: VL CF12

<400> SEQUENCE: 3
gacattgtgc tgacccaatc tccagcttct ttggctgtgt ctctagggca gagggccacc      60
atctcctgca aggccagcca agtgttgat tatgatggtg atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatccgtac     300
acgttcggag gggggaccaa gctggaaata aaa                                 333

<210> SEQ ID NO 4
<211> LENGTH: 111
<212> TYPE: PRT
<213> ORGANISM: Artificial Sequence
<220> FEATURE:
<223> OTHER INFORMATION: VL CF12

<400> SEQUENCE: 4

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

```
<210> SEQ ID NO 5
<211> LENGTH: 8
<212> TYPE: PRT
<213> ORGANISM: Artificial Sequence
<220> FEATURE:
<223> OTHER INFORMATION: VH-CDR1 CF12

<400> SEQUENCE: 5

Gly Phe Thr Phe Ser Ser Ser Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: VH-CDR2 CF12

<400> SEQUENCE: 6

Ile Tyr Ala Gly Thr Gly Gly Thr
1               5

<210> SEQ ID NO 7
<211> LENGTH: 9
<212> TYPE: PRT
<213> ORGANISM: Artificial Sequence
<220> FEATURE:
<223> OTHER INFORMATION: VH-CDR3 CF12

<400> SEQUENCE: 7

Ala Arg His Gly Ser Tyr Phe Asp Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: VL-CDR1 CF12

<400> SEQUENCE: 8

Gln Ser Val Asp Tyr Asp Gly Asp Ser Tyr
1               5                   10

<210> SEQ ID NO 9
<211> LENGTH: 9
<212> TYPE: PRT
<213> ORGANISM: Artificial Sequence
<220> FEATURE:
<223> OTHER INFORMATION: VL-CDR3 CF12

<400> SEQUENCE: 9

Gln Gln Ser Asn Glu Asp Pro Tyr Thr
1               5

<210> SEQ ID NO 10
<211> LENGTH: 765
<212> TYPE: DNA
<213> ORGANISM: Artificial Sequence
<220> FEATURE:
<223> OTHER INFORMATION: ScFv CF12

<400> SEQUENCE: 10
caggtgcagc tgcagcagtc gggtggcgca gagctggtga accgggtgc gagcgttaaa      60 ctgagctgca aaactagcgg ctttaccttt agctcgtcat atatttcgtg gctgaagcag     120
```

```
aaaccgggcc agtcactgga atggattgcg tggatctacg caggcacggg tggcacctca    180
tataatcaga aattcaccgg taaagcgcaa ctgacggtcg ataccagcag cagcacggcg    240
tacatgcagt tcagctcgct gaccactgaa gatagcgcaa tctactattg tgcacgccat    300
ggttcgtact tcgactattg gggccagggc accaccctga ccgtttcaag cggtggtggt    360
ggtagcggtg gtggtggttc aggtggcggc ggctcagata ttcagatgac ccagacccct    420
gcgagcctgg cagtgtcact gggccaacgc gcaaccatct cgtgtaaagc ctcgcagagc    480
gtggattatg acggcgatag ctacatgaac tggtatcagc aaaagcctgg tcaaccgccg    540
aagctgctga tttacgccgc cagcaacctg aatcgggca tcccggcccg ttttagcggc    600
tcaggctcgg gtactgactt cacgctgaac attcacccgg tagaagaaga agacgcggcc    660
acgtattact gccagcaaag caatgaagac ccgtacactt ttggcggcgg cacgaaactc    720
gagatcaaac accatcacca tcaccattaa ctcgagatca agtaa                   765
```

<210> SEQ ID NO 11
<211> LENGTH: 249
<212> TYPE: PRT
<213> ORGANISM: Artificial Sequence
<220> FEATURE:
<223> OTHER INFORMATION: ScFv CF12

<400> SEQUENCE: 11

```
Gln Val Gln Leu Gln Gln Ser Gly Gly Ala Glu Leu Val Lys Pro Gly
1               5                   10                  15

Ala Ser Val Lys Leu Ser Cys Lys Thr Ser Gly Phe Thr Phe Ser Ser
            20                  25                  30

Ser Tyr Ile Ser Trp Leu Lys Gln Lys Pro Gly Gln Ser Leu Glu Trp
        35                  40                  45

Ile Ala Trp Ile Tyr Ala Gly Thr Gly Gly Thr Ser Tyr Asn Gln Lys
    50                  55                  60

Phe Thr Gly Lys Ala Gln Leu Thr Val Asp Thr Ser Ser Ser Thr Ala
65                  70                  75                  80

Tyr Met Gln Phe Ser Ser Leu Thr Thr Glu Asp Ser Ala Ile Tyr Tyr
                85                  90                  95

Cys Ala Arg His Gly Ser Tyr Phe Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Asp Ile Gln Met Thr Gln Thr Pro Ala Ser Leu Ala
    130                 135                 140

Val Ser Leu Gly Gln Arg Ala Thr Ile Ser Cys Lys Ala Ser Gln Ser
145                 150                 155                 160

Val Asp Tyr Asp Gly Asp Ser Tyr Met Asn Trp Tyr Gln Gln Lys Pro
                165                 170                 175

Gly Gln Pro Pro Lys Leu Leu Ile Tyr Ala Ala Ser Asn Leu Glu Ser
            180                 185                 190

Gly Ile Pro Ala Arg Phe Ser Gly Ser Gly Ser Gly Thr Asp Phe Thr
        195                 200                 205

Leu Asn Ile His Pro Val Glu Glu Glu Asp Ala Ala Thr Tyr Tyr Cys
    210                 215                 220

Gln Gln Ser Asn Glu Asp Pro Tyr Thr Phe Gly Gly Gly Thr Lys Leu
225                 230                 235                 240

Glu Ile Lys His His His His His His
                245
```

<210> SEQ ID NO 12
<211> LENGTH: 35
<212> TYPE: DNA
<213> ORGANISM: Artificial Sequence
<220> FEATURE:
<223> OTHER INFORMATION: VHRev1

<400> SEQUENCE: 12
cgggatcctc tagaggtcca actgcaggag tcagg     35

<210> SEQ ID NO 13
<211> LENGTH: 37
<212> TYPE: DNA
<213> ORGANISM: Artificial Sequence
<220> FEATURE:
<223> OTHER INFORMATION: VHRev2

<400> SEQUENCE: 13
agatctagaa agcttaggtc aagctgcagc agtcagg     37

<210> SEQ ID NO 14
<211> LENGTH: 20
<212> TYPE: DNA
<213> ORGANISM: Artificial Sequence
<220> FEATURE:
<223> OTHER INFORMATION: MuCFor

<400> SEQUENCE: 14
ggggaagaca tttgggaagg     20

<210> SEQ ID NO 15
<211> LENGTH: 21
<212> TYPE: DNA
<213> ORGANISM: Artificial Sequence
<220> FEATURE:
<223> OTHER INFORMATION: MKRev2

<400> SEQUENCE: 15
gatattgtga tgacgcaggc t     21

<210> SEQ ID NO 16
<211> LENGTH: 18
<212> TYPE: DNA
<213> ORGANISM: Artificial Sequence
<220> FEATURE:
<223> OTHER INFORMATION: MKRev3

<400> SEQUENCE: 16
gatattgtga taacccag     18

<210> SEQ ID NO 17
<211> LENGTH: 21
<212> TYPE: DNA
<213> ORGANISM: Artificial Sequence
<220> FEATURE:
<223> OTHER INFORMATION: MKRev4

<400> SEQUENCE: 17
gacattgtgc tgacccaatc t     21

<210> SEQ ID NO 18
<211> LENGTH: 21
<212> TYPE: DNA
<213> ORGANISM: Artificial Sequence
<220> FEATURE:

```
<223> OTHER INFORMATION: MKRev5

<400> SEQUENCE: 18
gacattgtga tgacccagtc t                                               21

<210> SEQ ID NO 19
<211> LENGTH: 21
<212> TYPE: DNA
<213> ORGANISM: Artificial Sequence
<220> FEATURE:
<223> OTHER INFORMATION: MKRev8

<400> SEQUENCE: 19
gacatccagc tgactcagtc t                                               21

<210> SEQ ID NO 20
<211> LENGTH: 21
<212> TYPE: DNA
<213> ORGANISM: Artificial Sequence
<220> FEATURE:
<223> OTHER INFORMATION: MKC5For

<400> SEQUENCE: 20
ggatacagtt ggtgcagcat c                                               21

<210> SEQ ID NO 21
<211> LENGTH: 21
<212> TYPE: DNA
<213> ORGANISM: Artificial Sequence
<220> FEATURE:
<223> OTHER INFORMATION: CF12VH Fw

<400> SEQUENCE: 21
cagkaactgc aggtgtccwc t                                               21

<210> SEQ ID NO 22
<211> LENGTH: 23
<212> TYPE: DNA
<213> ORGANISM: Artificial Sequence
<220> FEATURE:
<223> OTHER INFORMATION: CF12VH Rev

<400> SEQUENCE: 22
ctggaggatg tgtctacagt cag                                             23

<210> SEQ ID NO 23
<211> LENGTH: 21
<212> TYPE: DNA
<213> ORGANISM: Artificial Sequence
<220> FEATURE:
<223> OTHER INFORMATION: CF12VL Fw

<400> SEQUENCE: 23
ctgctatggg tgctgctgct c                                               21

<210> SEQ ID NO 24
<211> LENGTH: 23
<212> TYPE: DNA
<213> ORGANISM: Artificial Sequence
<220> FEATURE:
<223> OTHER INFORMATION: CF12VL-Rev

<400> SEQUENCE: 24
agattggatg cagcatagat gag                                             23
```

```
<210> SEQ ID NO 25
<211> LENGTH: 14
<212> TYPE: PRT
<213> ORGANISM: Artificial Sequence
<220> FEATURE:
<223> OTHER INFORMATION: Lieur

<400> SEQUENCE: 25

Gly Gly Gly Gly Ser Gly Gly Gly Ser Gly Gly Gly Ser
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Fragment VL de scFv

<400> SEQUENCE: 26

Leu Glu Ile Lys His His His His His His Leu Glu Ile Lys Val Asp
1               5                   10                  15

<210> SEQ ID NO 27
<211> LENGTH: 354
<212> TYPE: DNA
<213> ORGANISM: Artificial Sequence
<220> FEATURE:
<223> OTHER INFORMATION: VL CF12

<400> SEQUENCE: 27
gatattcaga tgacccagac ccctgcgagc ctggcagtgt cactgggcca acgcgcaacc      60
atctcgtgta aagcctcgca gagcgtggat tatgacggcg atagctacat gaactggtat     120
cagcaaaagc ctggtcaacc gccgaagctg ctgatttacg ccgccagcaa cctggaatcg     180
ggcatcccgg cccgttttag cggctcaggc tcgggtactg acttcacgct gaacattcac     240
ccggtagaag aagaagacgc ggccacgtat tactgccagc aaagcaatga agacccgtac     300
acttttggcg gcggcacgaa acttgagatc aaacaccatc accatcacca ttaa           354

<210> SEQ ID NO 28
<211> LENGTH: 117
<212> TYPE: PRT
<213> ORGANISM: Artificial Sequence
<220> FEATURE:
<223> OTHER INFORMATION: VL CF12

<400> SEQUENCE: 28

Asp Ile Gln Met Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys His
            100                 105                 110

His His His His His
        115
```

<210> SEQ ID NO 29
<211> LENGTH: 372
<212> TYPE: DNA
<213> ORGANISM: Artificial Sequence
<220> FEATURE:
<223> OTHER INFORMATION: VH CF12

<400> SEQUENCE: 29

```
caggtgcagc tgcagcagtc gggtggcgca gagctggtga aaccgggtgc gagcgttaaa      60
ctgagctgca aaactagcgg ctttaccttt agctcgtcat atatttcgtg gctgaagcag     120
aaaccgggcc agtcactgga atggattgcg tggatctacg caggcacggg tggcacctca     180
tataatcaga aattcaccgg taaagcgcaa ctgacggtcg ataccagcag cagcacggcg     240
tacatgcagt tcagctcgct gaccactgaa gatagcgcaa tctactattg tgcacgccat     300
ggttcgtact cgactattg gggccagggc accaccctga ccgtttcaag ccaccatcac     360
catcaccatt aa                                                          372
```

<210> SEQ ID NO 30
<211> LENGTH: 123
<212> TYPE: PRT
<213> ORGANISM: Artificial Sequence
<220> FEATURE:
<223> OTHER INFORMATION: VH CF12

<400> SEQUENCE: 30

Gln Val Gln Leu Gln Gln Ser Gly Gly Ala Glu Leu Val Lys Pro Gly
1               5                   10                  15

Ala Ser Val Lys Leu Ser Cys Lys Thr Ser Gly Phe Thr Phe Ser Ser
            20                  25                  30

Ser Tyr Ile Ser Trp Leu Lys Gln Lys Pro Gly Gln Ser Leu Glu Trp
        35                  40                  45

Ile Ala Trp Ile Tyr Ala Gly Thr Gly Gly Thr Ser Tyr Asn Gln Lys
    50                  55                  60

Phe Thr Gly Lys Ala Gln Leu Thr Val Asp Thr Ser Ser Ser Thr Ala
65                  70                  75                  80

Tyr Met Gln Phe Ser Ser Leu Thr Thr Glu Asp Ser Ala Ile Tyr Tyr
                85                  90                  95

Cys Ala Arg His Gly Ser Tyr Phe Asp Tyr Trp Gly Gln Gly Thr Thr
            100                 105                 110

Leu Thr Val Ser Ser His His His His His
        115                 120

<210> SEQ ID NO 31
<211> LENGTH: 750
<212> TYPE: DNA
<213> ORGANISM: Artificial Sequence
<220> FEATURE:
<223> OTHER INFORMATION: ScFv CF12 inverse

<400> SEQUENCE: 31

```
gatattcaga tgacccagac ccctgcgagc ctggcagtgt cactgggcca acgcgcaacc      60
atctcgtgta aagcctcgca gagcgtggat tatgacggcg atagctacat gaactggtat     120
cagcaaaagc ctggtcaacc gccgaagctg ctgatttacg ccgccagcaa cctggaatcg     180
ggcatcccgg cccgttttag cggctcaggc tcgggtactg acttcacgct gaacattcac     240
ccggtagaag aagaagacgc ggccacgtat tactgccagc aaagcaatga agacccgtac     300
```

```
actttttggcg gcggcacgaa acttgagatc aaaggtggtg gtggtagcgg tggtggtggt    360
tcaggtggcg gcggctcaca ggtgcagctg cagcagtcgg gtggcgcaga gctggtgaaa    420
ccgggtgcga gcgttaaact gagctgcaaa actagcggct ttacctttag ctcgtcatat    480
atttcgtggc tgaagcagaa accgggccag tcactggaat ggattgcgtg gatctacgca    540
ggcacgggtg gcacctcata taatcagaaa ttcaccggta aagcgcaact gacggtcgat    600
accagcagca gcacggcgta catgcagttc agctcgctga ccactgaaga tagcgcaatc    660
tactattgtg cacgccatgg ttcgtacttc gactattggg gccagggcac caccctgacc    720
gtttcaagcc accatcacca tcaccattaa                                     750
```

<210> SEQ ID NO 32
<211> LENGTH: 249
<212> TYPE: PRT
<213> ORGANISM: Artificial Sequence
<220> FEATURE:
<223> OTHER INFORMATION: ScFv CF12 inverse

<400> SEQUENCE: 32

```
Asp Ile Gln Met Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Gly Ala Glu Leu Val Lys Pro Gly Ala Ser
    130                 135                 140

Val Lys Leu Ser Cys Lys Thr Ser Gly Phe Thr Phe Ser Ser Ser Tyr
145                 150                 155                 160

Ile Ser Trp Leu Lys Gln Lys Pro Gly Gln Ser Leu Glu Trp Ile Ala
                165                 170                 175

Trp Ile Tyr Ala Gly Thr Gly Gly Thr Ser Tyr Asn Gln Lys Phe Thr
            180                 185                 190

Gly Lys Ala Gln Leu Thr Val Asp Thr Ser Ser Ser Thr Ala Tyr Met
        195                 200                 205

Gln Phe Ser Ser Leu Thr Thr Glu Asp Ser Ala Ile Tyr Tyr Cys Ala
    210                 215                 220

Arg His Gly Ser Tyr Phe Asp Tyr Trp Gly Gln Gly Thr Thr Leu Thr
225                 230                 235                 240

Val Ser Ser His His His His His His
                245
```

<210> SEQ ID NO 33
<211> LENGTH: 92
<212> TYPE: PRT

```
<213> ORGANISM: Homo sapiens
<220> FEATURE:
<221> NAME/KEY: misc_feature
<223> OTHER INFORMATION: Sous-unite alpha hFSH, hCG et HLH
<220> FEATURE:
<221> NAME/KEY: misc_feature
<222> LOCATION: (17)..(17)
<223> OTHER INFORMATION: Xaa = Leu ou Phe

<400> SEQUENCE: 33

Ala Pro Asp Val Gln Asp Cys Pro Glu Cys Thr Leu Gln Glu Asn Pro
1               5                   10                  15

Xaa Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 34
<211> LENGTH: 96
<212> TYPE: PRT
<213> ORGANISM: Ovis aries
<220> FEATURE:
<221> NAME/KEY: misc_feature
<223> OTHER INFORMATION: Sous-unite alpha oLH et oFSH

<400> SEQUENCE: 34

Phe Pro Asp Gly Glu Phe Thr Met Gln Gly Cys Pro Glu Cys Lys Leu
1               5                   10                  15

Lys Glu Asn Lys Tyr Phe Ser Lys Pro Asp Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95

<210> SEQ ID NO 35
<211> LENGTH: 96
<212> TYPE: PRT
<213> ORGANISM: Sus scrofa
<220> FEATURE:
<221> NAME/KEY: misc_feature
<223> OTHER INFORMATION: sous-unite alpha pLH et pFSH

<400> SEQUENCE: 35

Phe Pro Asp Gly Glu Phe Thr Met Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
```

```
                    50                  55                  60
Val Ala Lys Ala Phe Thr Lys Ala Thr Val Met Gly Asn Ala Arg Val
 65                  70                  75                  80

Glu Asn His Thr Glu Cys His Cys Ser Thr Cys Tyr Tyr His Lys Ser
                     85                  90                  95

<210> SEQ ID NO 36
<211> LENGTH: 111
<212> TYPE: PRT
<213> ORGANISM: Homo sapiens
<220> FEATURE:
<221> NAME/KEY: misc_feature
<223> OTHER INFORMATION: sous-unite beta hFSH

<400> SEQUENCE: 36

Asn Ser Cys Glu Leu Thr Asn Ile Thr Ile Ala Ile Glu Lys Glu Glu
  1               5                  10                  15

Cys Arg Phe Cys Ile Ser Ile Asn Thr Thr Trp Cys Ala Gly Tyr Cys
                 20                  25                  30

Tyr Thr Arg Asp Leu Val Tyr Lys Asp Pro Ala Arg Pro Lys Ile Gln
             35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu Met Lys Glu
            100                 105                 110

<210> SEQ ID NO 37
<211> LENGTH: 132
<212> TYPE: PRT
<213> ORGANISM: Homo sapiens
<220> FEATURE:
<221> NAME/KEY: misc_feature
<223> OTHER INFORMATION: sous-unite beta hCG

<400> SEQUENCE: 37

Ser Lys Glu Pro Leu Arg Pro Arg Cys Arg Pro Ile Asn Ala Thr Leu
  1               5                  10                  15

Ala Val Glu Lys Glu Gly Cys Pro Val Cys Ile Thr Val Asn Thr Thr
                 20                  25                  30

Ile Cys Ala Gly Tyr Cys Pro Thr Met Thr Arg Val Leu Gln Gly Val
             35                  40                  45

Leu Pro Ala Leu Pro Gln Val Val Cys Asn Tyr Arg Asp Val Arg Phe
 50                  55                  60

Glu Ser Ile Arg Leu Pro Gly Cys Pro Arg Gly Val Asn Pro Val Val
 65                  70                  75                  80

Ser Tyr Ala Val Ala Leu Ser Cys Gln Cys Ala Leu Cys Arg Arg Ser
                 85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
            115                 120                 125

Pro Ser Pro Ser
130
```

-continued

```
<210> SEQ ID NO 38
<211> LENGTH: 123
<212> TYPE: PRT
<213> ORGANISM: Homo sapiens
<220> FEATURE:
<221> NAME/KEY: misc_feature
<223> OTHER INFORMATION: sous-unite beta hLH

<400> SEQUENCE: 38

Ser Arg Glu Pro Leu Arg Pro Arg Pro Trp Cys His Pro Ile Asn Ala
1               5                   10                  15

Ile Leu Ala Val Glu Lys Glu Gly Cys Pro Val Cys Ile Thr Val Asn
            20                  25                  30

Thr Thr Ile Cys Ala Gly Tyr Cys Pro Thr Met Met Arg Val Leu Gln
        35                  40                  45

Ala Val Leu Pro Pro Leu Pro Gln Val Val Cys Thr Tyr Arg Asp Val
    50                  55                  60

Arg Phe Glu Ser Ile Arg Leu Pro Gly Cys Pro Arg Gly Val Asp Pro
65                  70                  75                  80

Val Val Ser Phe Pro Val Ala Leu Ser Cys Arg Cys Gly Pro Cys Arg
                85                  90                  95

Arg Ser Thr Ser Asp Cys Gly Gly Pro Lys Asp His Pro Leu Thr Cys
            100                 105                 110

Asp His Pro Gln Leu Ser Gly Leu Leu Phe Leu
        115                 120

<210> SEQ ID NO 39
<211> LENGTH: 121
<212> TYPE: PRT
<213> ORGANISM: Ovis aries
<220> FEATURE:
<221> NAME/KEY: misc_feature
<223> OTHER INFORMATION: sous-unite beta oLH

<400> SEQUENCE: 39

Ser Arg Gly Pro Leu Arg Pro Leu Cys Gln Pro Ile Asn Ala Thr Leu
1               5                   10                  15

Ala Ala Glu Lys Glu Ala Cys Pro Val Cys Ile Thr Phe Thr Thr Ser
            20                  25                  30

Ile Cys Ala Gly Tyr Cys Leu Ser Met Lys Arg Val Leu Pro Val Ile
        35                  40                  45

Leu Pro Pro Met Pro Gln Arg Val Cys Thr Tyr His Glu Leu Arg Phe
    50                  55                  60

Ala Ser Val Arg Leu Pro Gly Cys Pro Pro Gly Val Asp Pro Met Val
65                  70                  75                  80

Ser Phe Pro Val Ala Leu Ser Cys His Cys Gly Pro Cys Arg Leu Ser
                85                  90                  95

Ser Thr Asp Cys Gly Gly Pro Arg Thr Gln Pro Leu Ala Cys Asp His
            100                 105                 110

Pro Pro Leu Pro Asp Ile Leu Phe Leu
        115                 120

<210> SEQ ID NO 40
<211> LENGTH: 121
<212> TYPE: PRT
<213> ORGANISM: Sus scrofa
<220> FEATURE:
<221> NAME/KEY: misc_feature
<223> OTHER INFORMATION: sous-unite beta pLH

<400> SEQUENCE: 40
```

```
Ser Arg Gly Pro Leu Arg Pro Leu Cys Arg Pro Ile Asn Ala Thr Leu
1               5                   10                  15

Ala Ala Glu Asn Glu Ala Cys Pro Val Cys Ile Thr Phe Thr Thr Ser
                20                  25                  30

Ile Cys Ala Gly Tyr Cys Pro Ser Met Val Arg Val Leu Pro Ala Ala
                35                  40                  45

Leu Pro Pro Val Pro Gln Pro Val Cys Thr Tyr Arg Glu Leu Ser Phe
50                      55                  60

Ala Ser Ile Arg Leu Pro Gly Cys Pro Pro Gly Val Asp Pro Thr Val
65                  70                  75                  80

Ser Phe Pro Val Ala Leu Ser Cys His Cys Gly Pro Cys Arg Leu Ser
                85                  90                  95

Ser Ser Asp Cys Gly Gly Pro Arg Ala Gln Pro Leu Ala Cys Asp Arg
                100                 105                 110

Pro Leu Leu Pro Gly Leu Leu Phe Leu
            115                 120
```

<210> SEQ ID NO 41
<211> LENGTH: 110
<212> TYPE: PRT
<213> ORGANISM: Ovis aries
<220> FEATURE:
<221> NAME/KEY: misc_feature
<223> OTHER INFORMATION: sous-unite beta oFSH

<400> SEQUENCE: 41

```
Ser Cys Glu Leu Thr Asn Ile Thr Ile Thr Val Glu Lys Glu Glu Cys
1               5                   10                  15

Ser Phe Cys Ile Ser Ile Asn Thr Thr Trp Cys Ala Gly Tyr Cys Tyr
                20                  25                  30

Thr Arg Asp Leu Val Tyr Lys Asp Pro Ala Arg Pro Asn Ile Gln Lys
                35                  40                  45

Ala Cys Thr Phe Lys Glu Leu Val Tyr Glu Thr Val Lys Val Pro Gly
50                      55                  60

Cys Ala His His Ala Asp Ser Leu Tyr Thr Tyr Pro Val Ala Thr Glu
65                  70                  75                  80

Cys His Cys Gly Lys Cys Asp Arg Asp Ser Thr Asp Cys Thr Val Arg
                85                  90                  95

Gly Leu Gly Pro Ser Tyr Cys Ser Phe Ser Asp Ile Arg Glu
                100                 105                 110
```

<210> SEQ ID NO 42
<211> LENGTH: 109
<212> TYPE: PRT
<213> ORGANISM: Sus scrofa
<220> FEATURE:
<221> NAME/KEY: misc_feature
<223> OTHER INFORMATION: sous-unite beta pFSH

<400> SEQUENCE: 42

```
Cys Glu Leu Thr Asn Ile Thr Ile Thr Val Glu Lys Glu Glu Cys Gly
1               5                   10                  15

Phe Cys Ile Ser Ile Asn Thr Thr Trp Cys Ala Gly Tyr Cys Tyr Thr
                20                  25                  30

Arg Asp Leu Val Tyr Lys Asp Pro Ala Arg Pro Asn Ile Gln Lys Thr
                35                  40                  45

Cys Thr Phe Lys Glu Leu Val Tyr Glu Thr Val Lys Val Pro Gly Cys
50                      55                  60
```

```
Ala His His Ala Asp Ser Leu Tyr Thr Tyr Pro Val Ala Thr Glu Cys
 65                  70                  75                  80

His Cys Gly Lys Cys Asp Ser Asp Ser Thr Asp Cys Thr Val Arg Gly
                 85                  90                  95

Leu Gly Pro Ser Tyr Cys Ser Phe Ser Glu Met Lys Glu
            100                 105

<210> SEQ ID NO 43
<211> LENGTH: 49
<212> TYPE: PRT
<213> ORGANISM: Homo sapiens
<220> FEATURE:
<221> NAME/KEY: misc_feature
<223> OTHER INFORMATION: Region N terminale du recepteur de la hFSH

<400> SEQUENCE: 43

Cys His His Arg Ile Cys His Cys Ser Asn Arg Val Phe Leu Cys Gln
 1               5                  10                  15

Glu Ser Lys Val Thr Glu Ile Pro Ser Asp Leu Pro Arg Asn Ala Ile
             20                  25                  30

Glu Leu Arg Phe Val Leu Thr Lys Leu Arg Val Ile Gln Lys Gly Ala
         35                  40                  45

Phe
```